US009051567B2

(12) United States Patent
Fitzgerald et al.

(10) Patent No.: US 9,051,567 B2
(45) Date of Patent: Jun. 9, 2015

(54) METHODS FOR INCREASING EFFICACY OF LIPID FORMULATED SIRNA

(75) Inventors: Kevin Fitzgerald, Brookline, MA (US); Maria Frank-Kamenetsky, Brookline, MA (US); Akin Akinc, Needham, MA (US); Martin A. Maier, Belmont, MA (US)

(73) Assignee: Tekmira Pharmaceuticals Corporation, Burnaby, British Columbia (CA)

( * ) Notice: Subject to any disclaimer, the term of this patent is extended or adjusted under 35 U.S.C. 154(b) by 69 days.

(21) Appl. No.: 13/378,346

(22) PCT Filed: Jun. 15, 2010

(86) PCT No.: PCT/US2010/038679
§ 371 (c)(1),
(2), (4) Date: Jun. 11, 2012

(87) PCT Pub. No.: WO2010/147992
PCT Pub. Date: Dec. 23, 2010

(65) Prior Publication Data
US 2012/0244207 A1 Sep. 27, 2012

Related U.S. Application Data

(60) Provisional application No. 61/187,242, filed on Jun. 15, 2009.

(51) Int. Cl.
*A61K 31/713* (2006.01)
*A61K 9/127* (2006.01)
*A61P 3/06* (2006.01)
*C12N 15/11* (2006.01)
*C12N 15/113* (2010.01)
*C12N 9/64* (2006.01)

(52) U.S. Cl.
CPC .......... *C12N 15/111* (2013.01); *C12N 15/1135* (2013.01); *C12N 15/1136* (2013.01); *C12N 15/1137* (2013.01); *C12N 15/1138* (2013.01); *C12N 2310/14* (2013.01); *C12N 2320/31* (2013.01); *C12N 2320/32* (2013.01); *C12Y 304/21061* (2013.01); *C12N 9/6454* (2013.01)

(58) Field of Classification Search
None
See application file for complete search history.

(56) References Cited

U.S. PATENT DOCUMENTS

| | | | |
|---|---|---|---|
| 6,054,299 A | 4/2000 | Conrad | |
| 6,271,359 B1 | 8/2001 | Norris et al. | |
| 7,427,605 B2 | 9/2008 | Davis et al. | |
| 7,605,251 B2 | 10/2009 | Tan et al. | |
| 7,650,525 B1 | 1/2010 | Chang et al. | |
| 7,718,629 B2 | 5/2010 | Bumcrot et al. | |
| 8,168,775 B2 | 5/2012 | Sah et al. | |
| 8,222,222 B2 | 7/2012 | Tan et al. | |
| 8,273,869 B2 | 9/2012 | Fitzgerald et al. | |
| 2003/0143732 A1 | 7/2003 | Fosnaugh et al. | |
| 2003/0170891 A1 | 9/2003 | McSwiggen | |
| 2003/0229037 A1 | 12/2003 | Massing et al. | |
| 2004/0009216 A1 | 1/2004 | Rodrigueza et al. | |
| 2004/0259247 A1 | 12/2004 | Tuschl et al. | |
| 2005/0170508 A1 | 8/2005 | Huang et al. | |
| 2006/0003322 A1 | 1/2006 | Bentwich et al. | |
| 2006/0008910 A1 | 1/2006 | MacLachlan et al. | |
| 2006/0083780 A1 | 4/2006 | Heyes et al. | |
| 2006/0134189 A1 | 6/2006 | MacLachlan et al. | |
| 2006/0240093 A1 | 10/2006 | MacLachlan et al. | |
| 2006/0263435 A1 | 11/2006 | Davis et al. | |
| 2007/0004664 A1 | 1/2007 | McSwiggen et al. | |
| 2007/0031844 A1 | 2/2007 | Khvorova et al. | |
| 2007/0135372 A1 | 6/2007 | MacLachlan et al. | |
| 2007/0173473 A1 | 7/2007 | McSwiggen et al. | |
| 2007/0275914 A1* | 11/2007 | Manoharan et al. | 514/44 |
| 2007/0281899 A1 | 12/2007 | Bumcrot et al. | |
| 2008/0113930 A1* | 5/2008 | Tan et al. | 514/44 |
| 2008/0188675 A1 | 8/2008 | Chen et al. | |
| 2008/0249040 A1 | 10/2008 | McSwiggen et al. | |
| 2008/0253960 A1 | 10/2008 | Zheng et al. | |
| 2008/0306015 A1 | 12/2008 | Khvorova et al. | |
| 2009/0023215 A1 | 1/2009 | Jessee et al. | |
| 2009/0023673 A1 | 1/2009 | Manoharan et al. | |
| 2009/0142352 A1 | 6/2009 | Jackson et al. | |
| 2009/0149403 A1 | 6/2009 | MacLachlan | |
| 2009/0232738 A1 | 9/2009 | Glimcher et al. | |
| 2009/0275638 A1 | 11/2009 | Fitzgerald et al. | |
| 2009/0291131 A1 | 11/2009 | MacLachlan et al. | |
| 2010/0010066 A1 | 1/2010 | Fitzgerald et al. | |
| 2010/0120893 A1 | 5/2010 | Sah et al. | |

(Continued)

FOREIGN PATENT DOCUMENTS

| | | |
|---|---|---|
| DE | 101 00 586 | 11/2002 |
| EP | 1 471 152 | 10/2004 |
| WO | WO 96/40964 | 12/1996 |
| WO | WO 99/32619 | 7/1999 |
| WO | WO 99/53050 | 10/1999 |
| WO | WO 99/61631 | 12/1999 |
| WO | WO 00/22113 | 4/2000 |
| WO | WO 00/22114 | 4/2000 |
| WO | WO 00/44895 | 8/2000 |
| WO | WO 03/070918 | 8/2003 |

(Continued)

OTHER PUBLICATIONS

Graham MK, Antisense inhibition of proprotein convertase subtilisin/kexin type 9 reduces serum LDL in hyperlidemic mice, 2007, JLipidRes, 48, 763-767.*

(Continued)

*Primary Examiner* — Brian Gulledge
*Assistant Examiner* — Celeste A Roney
(74) *Attorney, Agent, or Firm* — Viksnins Harris & Padys PLLP

(57) ABSTRACT

This invention relates to methods for increasing the efficiency of siRNA administrations via pre-administration of an agent that increases LDL receptor levels.

25 Claims, 9 Drawing Sheets

(56) References Cited

U.S. PATENT DOCUMENTS

| | | | |
|---|---|---|---|
| 2010/0130588 A1 | 5/2010 | Yaworksi et al. | |
| 2010/0144834 A1 | 6/2010 | Freier et al. | |
| 2010/0168206 A1 | 7/2010 | Gollob et al. | |
| 2010/0324120 A1* | 12/2010 | Chen et al. | 514/44 A |
| 2011/0015250 A1 | 1/2011 | Bumcrot et al. | |
| 2011/0015252 A1 | 1/2011 | Fitzgerald et al. | |
| 2011/0117125 A1 | 5/2011 | Hope et al. | |
| 2011/0256175 A1 | 10/2011 | Hope et al. | |
| 2012/0016009 A1 | 1/2012 | Fitzgerald et al. | |

FOREIGN PATENT DOCUMENTS

| | | |
|---|---|---|
| WO | WO 2004/065601 | 8/2004 |
| WO | WO 2004/080406 | 9/2004 |
| WO | WO 2004/090108 | 10/2004 |
| WO | WO 2005/014782 | 2/2005 |
| WO | WO 2005/120152 | 12/2005 |
| WO | WO 2007/012191 | 2/2007 |
| WO | WO 2007/056861 | 5/2007 |
| WO | WO 2007/115168 | 10/2007 |
| WO | WO 2007/134161 | 11/2007 |
| WO | WO 2008/011431 | 1/2008 |
| WO | WO 2008/042973 | 4/2008 |
| WO | WO 2008/109472 | 9/2008 |
| WO | WO 2009/086558 | 7/2009 |
| WO | WO 2009/111658 | 9/2009 |
| WO | WO 2009/127060 | 10/2009 |
| WO | WO 2009/134487 | 11/2009 |
| WO | WO 2010/054406 | 5/2010 |
| WO | WO 2010/088537 | 8/2010 |
| WO | WO 2010/129709 | 11/2010 |
| WO | WO 2010/144740 | 12/2010 |
| WO | WO 2010/147992 | 12/2010 |
| WO | WO 2010/148013 | 12/2010 |
| WO | WO 2011/028938 | 3/2011 |
| WO | WO 2011/038031 | 3/2011 |
| WO | WO 2012/058693 | 5/2012 |

OTHER PUBLICATIONS

Abifadel, M., et al., "Mutations in *PCSK9* case autosomal dominant hypercholesterolemia," Nature Genetics, vol. 34, pp. 154-156, 2003.
Agrawal, S., et al., "Antisense oligonucleotides: towards clinical trials." Trends in Biotechnology. Oct. 1996, vol. 14, pp. 376-387.
Akdim, F., et al., "Antisense apolipoprotein B therapy: where do we stand?," Curr. Opin. Lipidol., vol. 18, pp. 397-400, 2007.
Basak, A., "Inhibitors of Proprotein Convertases". Journal of Molecular Medicine, 2002, vol. 83, pp. 844-855.
Bass, B., "The short answer," Nature, May 24, 2001, pp. 428-429, vol. 411.
Benjannet, S., et al., "NARC-1/PCSK9 and Its Natural Mutants," The Journal of Biological Chemistry, vol. 279, No. 47, pp. 48865-18875, Nov. 2004.
Bergeron, F., et al., Subtilase-like pro-protein convertases: from molecular specificity to therapeutic applications, Journal of Molecular Endocrinology, vol. 24, pp. 1-22, 2000.
Betteridge, D.J., et al., "Treatment of familial hypercholesterolaemia. United Kingdom lipid clinics study of pravastatin and cholestyramine," BMJ, vol. 304 pp. 1335-1338, May 1992.
Cohen, J.C., et al., "Low LDL cholesterol in individuals of African descent resulting from frequent nonsense mutations in *PCSK9*," Nature Genetics, vol. 37, pp. 161-165, 2005.
Cohen, J.C., et al., "Molecular mechanisms of autosomal recessive hypercholesterolemia," Current Opinion in Lipidology, vol. 14, pp. 121-127, 2003.
Cohen, J.C., et al., "Sequence Variations in *PCSK9*, Low LDL, and Protection against Coronary Heart Disease," N. Engl. J. Med., vol. 354, pp. 1264-1272, 2006.
Couture, L.A., et al., "Anti-gene therapy: the use of ribozymes to inhibit gene function," TIG, vol. 12, No. 12, pp. 510-515, 1996.

Downward, J., "RNA interference," BMJ, vol. 328, pp. 1245-1248, May 2004.
Dubuc, G., et al., "Statins Upregulate *PCSK9*, the Gene Encoding the Proprotein Convertase Neural Apoptosis-Regulated Convertase-1 Implicated in Familial Hypercholesterolemia," Arteriosclerosis, Thrombosis, and Vascular Biology, vol. 24, pp. 1454-1459, 2004.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in Drosophila Melanogaster Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Examination Report for Australian Patent Application No. 2010241357, Aug. 8, 2012, 4 pages.
Examination Report for New Zealand Patent Application No. 572666, Jun. 1, 2010, pages.
Examination Report for New Zealand Patent Application No. 572666, Sep. 21, 2010, 2 pages.
Examination Report for New Zealand Patent Application No. 587616, Sep. 1, 2010, 2 pages.
Examination Report for New Zealand Patent Application No. 587616, Dec. 20, 2011, 2 Pages.
Extended European Search Report for European Patent Application No. 07762085.4, Sep. 25, 2009, 11 Pages.
Extended European Search Report for European Patent Application No. 09015323.0, Apr. 28, 2010, 7 Pages.
Extended European Search Report for European Patent Application No. 09739290.6, May 7, 2012, 11 Pages.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
First Office Action for Chinese Patent Application No. 200780024854.1, dated Jun. 27, 2011, 7 pages.
Fitzgerald, K., et al., "Abstract 583: RNAi Therapeutics for the Lowering of Cholesterol," Circulation, 2007, p. II_105, vol. 116, American Heart Association, Inc.
Frank-Kamenetsky Maria et al., "Therapeutic RNAi targeting PCSK9 acutely lowers plasma cholesterol in rodents and LDL cholesterol in nonhuman primates", Proceedings of the National Academy of Sciences, Aug. 19, 2008, pp. 11915-11920, vol. 105, No. 33.
Gassmann, M., et al., "Maintenance of an extrachromosomal plasmid vector in mouse embryonic stem cells," PNAS, vol. 92, pp. 1292-1296, Feb. 1995.
GenBank Accession No. NM_000371, "*Homo sapiens* transthyretin (TTR), mRNA," NCBI, 2012, pp. 1-4.
GenBank Accession No. NM_002072.2, "*Homo sapiens* guanine nucleotide binding protein (G protein), q polypeptide (GNAZ), mRNA," NCBI, 2010, pp. 1-4.
GenBank Accession No. NM_004523, "*Homo sapiens* kinesin family member 11 (KIF11), mRNA," NCBI, 2012, pp. 1-6.
GenBank Accession No. NM_012681.1, "*Rattus norvegicus* transthyretin (Ttr), mRNA," NCBI, 2010, pp. 1-3.
GenBank Accession No. NM_013697.2, "*Mus musculus* traqnsthyretin (Ttr), mRNA," NCBI, 2007, pp. 1-3.
GenBank Accession No. NM_031036, "*Rattus norvegicus* guanine nucleotide binding protein (G protein), q polypeptide (Gnaq), mRNA," NCBI, 2012, pp. 1-3.
GenBank Accession No. NM_153565, "*Mus musculus* proprotein convertase subtilisin/kexin type 9 (PCSK9), mRNA," NCBI, 2012, pp. 1-5.
GenBank Accession No. NM_174936, "*Homo sapiens* proprotein convertse subtilisin/kexin type 9 (PCSK9), mRNA," NCBI, 2012, pp. 1-6.

(56) References Cited

OTHER PUBLICATIONS

GenBank Accession No. NM_199253, "*Rattus norvegicus* proprotein convertase subtilisin/kexin type 9(PCSK9), mRNA," NCBI, 2012, pp. 1-4.
Gensberg et al., "Subtilin-Related Serine Proteases in the Mammalian Constitutive Secretory Pathway," Seminars in Cell and Developmental Biology, 1998, vol. 9, pp. 11-17.
Graham, M.J., et al., Antisense inhibition of proprotein convertase subtilisin/kexin type 9 reduces serum LDL in hyperlipidemic mice, Journal of Lipid Research, vol. 48 pp. 767-769, 2007.
Harborth, J., et al., "Sequence, Chemical, and Structural Variation of Small Interfering RNAs and Short Hairpin RNAs and the Effect on Mammalian Gene Silencing," Antisense and Nucleic Acid Drug Development, 2003, vol. 13, pp. 83-105.
Hayes, M.E., et al., "Genospheres: self-assembling nucleic acid-lipid nanoparticles suitable for targeted gene delivery," Gene Therapy, vol. 13, pp. 646-651, 2006.
Heyes, J., et al., "Cationic lipid saturation influences intracellular delivery of encapsulated nucleic acids," Journal of Controlled Release, vol. 107, pp. 276-287, 2005.
Horton et al., "Molecular biology of PCSK9: its role in LDL metabolism", Trends in Biochemical Sciences, Feb. 6, 2007, pp. 71-77, vol. 32, No. 2.
Hungarian Intellectual Property Office, Search Report and Written Opinion, Singaporean Patent Application No. 201103340-4, Jul. 6, 2012, 31 pages.
Legace, T.A., et al., "Secreted PCSK9 decreases the number of LDL receptors in hepatocytes and in livers of parabiotic mice," J. Clin. Invest., vol. 116, pp. 2995-3005, 2006.
Leren, T.P., "Mutations in the *PCSK9* gene in Norwegian subjects with autosomal dominant hypercholesterolemia," Clin. Genet., vol. 65, pp. 419-422, 2004.
Li, S., et al., "Folate-Mediated Targeting of Antisense Oligodeoxynucleotides to Ovarian Cancer Cells," Pharmaceutical Research, vol. 15, No. 10, pp. 1540-1545, 1998.
Love, K.T., et al., "Lipid-like materials for low-dose, in vivo gene silencing," PNAS, vol. 107, No. 5, pp. 1864-1869, Feb. 2010.
Lu, P.Y., et al., "Delivery siRNA in vivo for functional genomics and novel therapeutics," RNA Interference Technology, Cambridge, Appasani, pp. 303-317, 2005.
Manoharan, M., et al., "Oligonucleotide Conjugates as Potential Antisense Drugs with Improved Uptake, Biodistribution, Targeted Delivery, and Mechanism of Action," Antisense & Nucleic Acid Drug Development, vol. 12, pp. 103-128, 2002.
Maxwell, K.N., et al., "Adenoviral-mediated expression of Pcsk9 in mice results in a low-density lipoprotein receptor knockout phenotype," PNAS, vol. 101, No. 18, pp. 7100-7105, May 2004.
Maxwell, K.N., et al., "Novel putative SREBP and LXR target genes identified by microarray analysis in liver of cholesterol-fed mice," Journal of Lipid Research, vol. 44, pp. 2109-2119, 2003.
Morrissey, D.V., et al., "Potent and persistent in vivo anti-HBV activity of chemically modified siRNAs," Nature Biotechnology, vol. 23, No. 8, pp. 1002-1007, Aug. 2005.
Notice of Preliminary Rejection for Korea Patent Application No. 10-2008-7030164, Aug. 13, 2010, 11 pages.
Office Action for U.S. Appl. No. 12/478,452, dated Mar. 25, 2011, 16 Pages.
Office Action for U.S. Appl. No. 12/816,207, dated Jul. 25, 2011, 13 Pages.
Office Action for U.S. Appl. No. 12/900,430, dated Apr. 20, 2012, 17 Pages.
Office Action for U.S. Appl. No. 13/245,730, dated Jul. 20, 2012, 21 Pages.
Official Action for Eurasian Patent Application No. 200870528, Oct. 4, 2010, 3 Pages.
Park, S.W., et al., "Post-transcriptional Regulation of Low Density Lipoprotein Receptor Protein by Proprotein Convertase Subtilisin/Kexin Type 9a in Mouse Liver," The Journal of Biological Chemistry, vol. 279, No. 48, pp. 50630-50638, Nov. 2004.
PCT International Search Report and Written Opinion for PCT/US2009/032743, Dec. 10, 2009, 11 Pages.
PCT International Search Report and Written Opinion for PCT/US2007/068655, Oct. 29, 2007, 15 Pages.
PCT International Search Report and Written Opinion for PCT/US2010/038707, Dec. 16, 2010, 18 Pages.
PCT International Search Report and Written Opinion for PCT/US2010/038679, Aug. 30, 2010, 9 Pages.
PCT International Search Report and Written Opinion for PCT/US2010/049868, Jan. 31, 2011, 15 Pages.
PCT International Search Report and Written Opinion for PCT/US2011/058682, May 25, 2012, 12 Pages.
PCT International Search Report and Written Opinion for PCT/US2010/047726, Dec. 13, 2010, 18 Pages.
PCT International Search Report for PCT/US2010/038224, Sep. 27, 2010, 2 Pages.
PCT Invitation to Pay Additional Fees and, Where Applicable, Protest Fee, PCT/US2010/038707, Oct. 14, 2010, 2 Pages.
PCT Invitation to Pay Additional Fees and, Where Applicable, Protest Fee, PCT/US2009/032743, Sep. 17, 2009, 2 Pages.
Rader, D.J., et al., "Monogenic hypercholesterolemia: new insights in pathogenesis and treatment," Journal of Clinical Investigation, vol. 111, pp. 1795-1803, 2003.
Rashid, S., et al., "Decreases plasma cholesterol and hypersensitivity to statin in mice lacking *Pcsk9*," PNAS, vol. 102, No. 15, pp. 5374-5379, Apr. 2005.
Requisition by the Examiner for Canadian Patent Application No. 2,651,839, Sep. 6, 2011, 3 pages.
Reynolds, et al. (2004) "Rational siRNA design for RNA interference," Nature Biotechnology, vol. 22, No. 3, pp. 326-330.
Robbins, M., et al., "Stable expression of shRNAs in human $CD34^+$ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Samarsky, D., et al., "RNAi in drug development: Practical considerations," RNA Interference Technology, Cambridge, Appasani, pp. 384-395, 2005.
Sauer, I., et al., "An Apolipoprotein E-Derived Peptide Mediates Uptake of Sterically Stabilized Liposomes into Brain Capillary Endothelial Cells," Biochemistry, 2005, pp. 2021-2029, vol. 44, No. 6.
Seidah, N. G., et al., "Proprotein and prohormone convertases: a family of subtilases generating diverse bioactive polypeptides," Brain Research, vol. 848, pp. 45-62, 1999.
Semple, S., et al., "Rational design of cationic lipids for siRNA delivery", Nature Biotechnology, Feb. 1, 2010, pp. 172-176, vol. 28, No. 2.
Shioji, K., et al., "Genetic variants in *PCSK9* affect the cholesterol level in Japanese," J. Hum. Genet., vol. 49, pp. 109-114, 2004.
Supplementary European Search Report for European Patent Application No. EP 09739290, May 7, 2012, 11 Pages.
Taylor, N.A., et al., "Curbing activation: proprotein convertases in homeostasis and pathology," FASEB, vol. 17, pp. 1215-1227, Jul. 2003.
Templeton, N.S., et al., "Improved DNA: liposome complexes for increases systemic delivery and gene expression," Nature Biotechnology, vol. 15, pp. 647-652, 1997.
Timms, K.M., et al., "A mutation in *PCSK9* causing autosomal-dominant hypercholesterolemia in a Utah pedigree," Hum. Genet., vol. 114, pp. 349-353, 2004.
Tuschl T., "RNA Interference and Small Interfering RNAs" Chembiochem, 2001, pp. 239-245, vol. 2.
Tuschl, T., "Expanding small RNA interference," Nature Biotechnology, May 2002, pp. 446-448, vol. 20.
Tuschl, T., "Functional genomics: RNA sets the standard," Nature, Jan. 16, 2003, vol. 421, No. 6920, pp. 220-221.
Tuschl, T., "Mammalian RNA Interference," RNAi, A Guide to Gene Silencing, Chapter 13, G.J. Hannon (ed,), 2003, pp. 265-295.

(56) References Cited

OTHER PUBLICATIONS

Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., et al., "Targeted mRNA Degradation by Double-Stranded RNA in Vitro," Genes & Development, 1999, pp. 3191-3197, vol. 13.
U.S. Appl. No. 60/799,458, filed May 11, 2006.
U.S. Appl. No. 60/817,203, filed Jun. 27, 2006.
U.S. Appl. No. 60/829,914, filed Oct. 18, 2006.
U.S. Appl. No. 60/840,089, filed Aug. 25, 2006.
U.S. Appl. No. 60/901,134, filed Feb. 13, 2007.
U.S. Appl. No. 61/024,968, filed Jan. 31, 2008.
U.S. Appl. No. 61/039,083, filed Mar. 24, 2008.
U.S. Appl. No. 61/076,548, filed Jun. 27, 2008.
U.S. Appl. No. 61/187,169, filed Jun. 15, 2009.
U.S. Appl. No. 61/187,242, filed Jun. 15, 2009.
U.S. Appl. No. 61/188,765, filed Aug. 11, 2008.
U.S. Appl. No. 61/218,350, filed Jun. 18, 2009.
U.S. Appl. No. 61/239,378, filed Sep. 2, 2009.
U.S. Appl. No. 61/244,790, filed Sep. 22, 2009.
U.S. Appl. No. 61/244,859, filed Sep. 22, 2009.
U.S. Appl. No. 61/285,598, filed Dec. 11, 2009.
U.S. Appl. No. 61/293,474, filed Jan. 8, 2010.
U.S. Appl. No. 61/313,584, filed Mar. 12, 2010.
U.S. Appl. No. 61/313/578, filed Mar. 12, 2010.
U.S. Appl. No. 61/408,513, filed Oct. 29, 2010.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Weil, et al (2002) "Targeting the Kinesin Eg5 to Monitor siRNA Transfection in Mammalian Cells," *Biotechniques* 33(6):1244-1248.
Yang, D., et al., "Evidence that processed small dsRNAs may mediate sequence-specific mRNA degradation during RNAi in *Drosophila* embryos," Current Biology, vol. 10, No. 19, pp. 1191-1200, 2000.
Zhou, A., et al., "Proteolytic Processing in the Secretory Pathway," The Journal of Biological Chemistry, vol. 274, No. 30, pp. 20745-20748, 1999.
Zimmerman, et al. (2006) "RNAi-mediated gene silencing in non-human primates," *Nature*, vol. 441, May 4: 111-114.
Lalanne, F., et al., "Wild-type PCSK9 inhibits LDL clearance but does not affect apoB-containing lipoprotein production in mouse and cultured cells," J. Lipid Res., vol. 46, No. 6, pp. 1312-1319, Jun. 2005.

\* cited by examiner

```
                              SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
aagcaaaaca ggucuagaat t                                                   21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uucuagaccu guuuugcuut t                                                   21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
uuccgaauaa acuccaggct t                                                   21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
gccuggaguu uauucggaat t                                                   21

<210> SEQ ID NO 5
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
aguuaguuua gauucucgat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
ucgagaaucu aaacuaacut t                                              21

<210> SEQ ID NO 7
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gucguguauc cucucuacuc gaa                                            23

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gcacauagga gagaugagcu u                                              21

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
auggaauacu cuugguuac                                                 19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
guaaccaaga guauuccau                                                 19
```

```
<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
auuaguauua ugcaaauug                                                       19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
caauuugcau aauacuaau                                                       19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
cugcacgguu cuuugugact t                                                    21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
gucacaaaga accgugcagt t                                                    21

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gaauggacag gucaaucaau cuu                                                  23

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 16
gauugauuga ccuguccauu c                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
gccuggaguu uauucggaat t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
uuccgaauaa acuccaggct t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
uucuagaccu guuuugcuut t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
aagcaaaaca ggucuagaat t                                              21
```

METHODS FOR INCREASING EFFICACY OF LIPID FORMULATED SIRNA

CROSS REFERENCE TO RELATED APPLICATIONS

This application is the National Stage of International Application No. PCT/US2010/038679, filed Jun. 15, 2010 and claims the benefit of U.S. Provisional Application No. 61/187,242, filed Jun. 15, 2009, the entire disclosure of which is hereby incorporated by reference in its entirety for all purposes.

REFERENCE TO A SEQUENCE LISTING

This application includes a Sequence Listing submitted electronically as a text file named 15265PCT_sequencelisting.txt, created on Dec. 14, 2011, with a size of 6,166 bytes. The sequence listing is incorporated by reference.

FIELD OF THE INVENTION

This invention relates to methods for increasing the efficacy of lipid formulated siRNA.

BACKGROUND OF THE INVENTION

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene. The dsRNA, e.g., siRNA, can be formulated in a number of formulations including, e.g., a lipid formulation.

SUMMARY OF THE INVENTION

Disclosed herein are methods for increasing the efficacy of lipid formulated siRNAs via administration of an agent that increases LDL receptor (LDLR) levels. Also disclosed are kits comprising the lipid formulated siRNA and the LDLR increasing agent.

According, the invention provides a method for administering a neutral liposomal formulated, siRNA targeting a gene to a subject comprising administering to the subject an agent that increases LDLR levels, and subsequently administering a first effective dose of the neutral liposomal formulated, siRNA targeting a gene, wherein said first effective dose is lower than a dose of the neutral liposomal formulated siRNA administered to the subject without the agent. In some embodiments the first effective dose is administered within 3 days of administering the agent.

The agent increases levels of LDL receptor by, e.g., at least 15%. Examples of said agents include but are not limited to statins, estradiols, or an inhibitor of PCSK9 expression, e.g., a PCSK9 targeted siRNA. Others examples of said agents include but are not limited to berberine, HMG CoA Reductase inhibitors, Squalene Synthetase inhibitors, HMG CoA Synthetase inhibitors, fenofibrates, LDLR RNAa, IDOL targeted siRNA, niacin, and ezetimibe. In some embodiments the agent is a PCSK9 targeted siRNA described herein, e.g., AD-10792 or, e.g., AD-9680. A PCSK9 targeted siRNA can be administered at a dose of about 0.5 to 10 mg/kg, e.g., at a dose of about 3 mg/kg.

The siRNA targeting a gene of interest is lipid formulated. The lipid formulation can be any known to one of skill in the art, including those disclosed herein, e.g., SNALP or LNP-01, LNP-8, or LNP-9. In some embodiments the lipid formulated siRNA includes an ApoE polypeptide.

The method includes administration of an siRNA targeting a gene. The gene can be any of interest and generally is associated with a disease or pathology. In some embodiments, the gene targeted by the siRNA is expressed in a cell expressing LDLR. For example, the gene targeted by the siRNA can be expressed in hepatocytes or adrenal gland or skin cells or muscle cells or kidney cells. In other embodiments the siRNA targets a VSP, TTR, PCSK-9, SCAP, S14, MIG12, APOC3, APOB, PNPLA3, Hepcidin, or a PCSK5 gene. For example, the siRNA can target a PCSK9 gene and includes the duplex, e.g., AD-9680 described herein, or includes an antisense strand with at least 15 contiguous nucleotides of the AD-9680 antisense strand, described herein.

The method can be performed in any subject of interest, e.g., a mouse or rat or monkey or human. In one embodiment the subject is human, e.g., a human in need of treatment for a disease correlated with expression of the targeted gene.

In the method described herein, the first effective dose of the neutral liposomal formulated siRNA is at least 2-50 fold, e.g., at least 2 fold, e.g., at least 10 fold, lower than dose administered without the agent. The siRNA inhibits expression of the target genes by at least 15%. In some embodiments the siRNA targets a PCSK9 gene and the first effective dose results in maintenance of at least a 40% decrease in total cholesterol levels.

In one embodiment the agent and the siRNA targeting a gene are the same compound, e.g., an siRNA targeting PCSK9. The method includes administering to a human an initial dose of neutral liposomal formulated, PCSK9 targeted dsRNA resulting in an initial lowering of total serum cholesterol levels in the human by at least 15%, and subsequently administering a first effective dose of the neutral liposomal formulated, PCSK9 targeted dsRNA resulting in maintenance of lowering of total serum cholesterol levels in the human by at least 15%, wherein said first effective dose is at least two fold lower than a dose of the neutral liposomal formulated, PCSK9 targeted dsRNA administered to the subject without the initial dose of the PCSK9 targeted dsRNA. The siRNA targeting PCSK can be, e.g., AD-10792 or AD-9680 described herein.

BRIEF DESCRIPTION OF THE DRAWINGS

The prefixes "AD-" "DP-" and "AL-DP-" are used interchangeably e.g., AL-DP-10792 and AD-10792.

DETAILED DESCRIPTION OF THE INVENTION

Figure 1A:
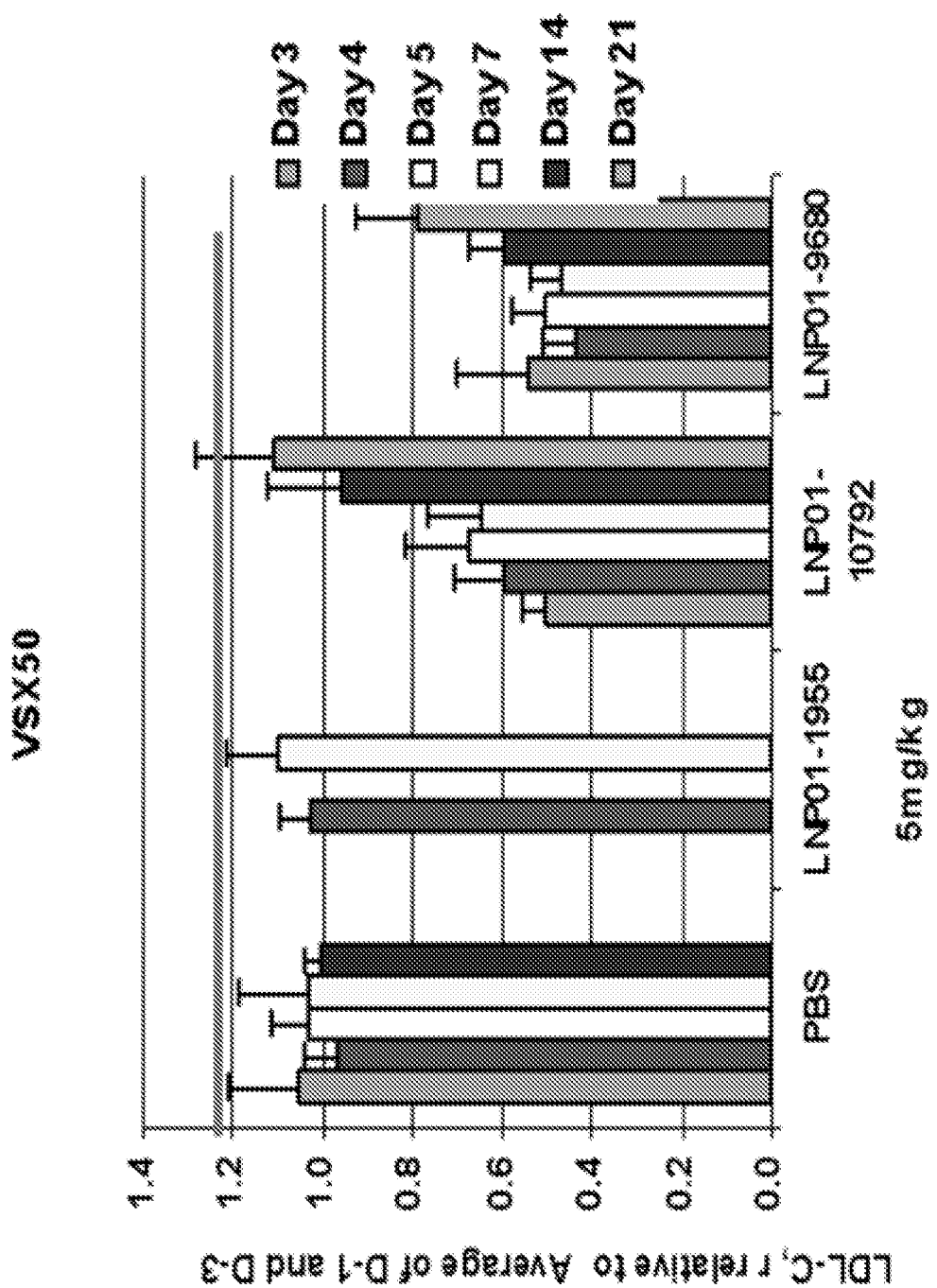
FIG. 1A-D shows the effects of PCSK9 siRNAs on LDLc and ApoB protein levels, total cholesterol/HDLc ratios, and PCSK9 protein levels, respectively, in nonhuman primates following a single dose of formulated AD-10792 or AD-9680.

The invention provides methods for increasing the efficacy of lipid formulated siRNA treatment via increasing expression of the low density lipoprotein receptor (LDL-R) using an agent, e.g., a statin or, e.g., a PCSK9 targeted siRNA.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"LDL" refers to low density lipoprotein particle.

"LDL-R" and "LDL receptor" are used interchangeably and refer to a low density lipoprotein particle receptor.

"Agent" and "agent that increase LDL-R expression" refers to any composition that, upon administration to a subject, increases the levels of LDL-R as determined by any method well known to one of skill in the art, e.g., as determined via mRNA or protein assay. Example agents include statins and PCSK9 targeted siRNA, as described herein.

"Neutral liposomal formulation" refers to a liposomal formulation with a near neutral or neutral surface charge at a physiological pH. Physiological pH can be, e.g., about 7.0 to about 7.5, or, e.g., about 7.5, or, e.g., 7.0, 7.1, 7.2, 7.3, 7.4, or 7.5, or, e.g., 7.3, or, e.g., 7.4. An example of a neutral liposomal formulation is an ionizable lipid nanoparticle (iLNP). A neutral liposomal formulation can include an ionizable cationic lipid, e.g., DLin-KC2-DMA. The weak basicity of the lipid headgroups of ionizable cationic lipids can affect the surface charge in a pH-dependent manner, rendering them positively charged at acidic pH, but close to charge-neutral at physiologic pH. A comparison of the similarities and differences between neutral liposomal formulations and cationic liposomal formulations (i.e., formulations with positive surface charge at a physiological pH), e.g., cLNPs, is described in more detail in Akinc et al., *Molecular Therapy* (May 11, 2010; Epub ahead of print), doi:10.1038/mt.2010.85; which is herein incorporated by reference in its entirety for all purposes.

"Target gene of interest," "target gene," and "gene of interest" and the like are used interchangeably, and refer to a gene that is targeted by the liposomal formulated siRNA. Examples include but are not limited to VSP (e.g., Eg5 and VEGF), TTR, PCSK9, SCAP, S14, MIG12, APOC3, APOB, PNPLA3, Hepcidin, or PCSK5 gene.

As used herein, "PCSK9" refers to the proprotein convertase subtilisin kexin 9 gene or protein (also known as FH3, HCHOLA3, NARC-1, NARC1). Examples of mRNA sequences to PCSK9 include but are not limited to the following: human: NM_174936; mouse: NM_153565, and rat: NM_199253. Additional examples of PCSK9 mRNA sequences are readily available using, e.g., GenBank.

As used herein, "Eg5" refers to the human kinesin family member 11, which is also known as KIF11, Eg5, HKSP, KSP, KNSL1 or TRIPS. Eg5 sequence can be found as NCBI GeneID: 3832, HGNC ID: HGNC: 6388 and RefSeq ID number: NM_004523. The terms "Eg5" and "KSP" and "Eg5/KSP" are used interchangeably As used herein, "VEGF," also known as vascular permeability factor, is an angiogenic growth factor. VEGF is a homodimeric 45 kDa glycoprotein that exists in at least three different isoforms. VEGF isoforms are expressed in endothelial cells. The VEGF gene contains 8 exons that express a 189-amino acid protein isoform. A 165-amino acid isoform lacks the residues encoded by exon 6, whereas a 121-amino acid isoform lacks the residues encoded by exons 6 and 7. VEGF145 is an isoform predicted to contain 145 amino acids and to lack exon 7. VEGF can act on endothelial cells by binding to an endothelial tyrosine kinase receptor, such as Flt-1 (VEGFR-1) or KDR/flk-1 (VEGFR-2). VEGFR-2 is expressed in endothelial cells and is involved in endothelial cell differentiation and vasculogenesis. A third receptor, VEGFR-3, has been implicated in lymphogenesis.

The various isoforms have different biologic activities and clinical implications. For example, VEGF145 induces angiogenesis and like VEGF189 (but unlike VEGF165), VEGF145 binds efficiently to the extracellular matrix by a mechanism that is not dependent on extracellular matrix-associated heparin sulfates. VEGF displays activity as an endothelial cell mitogen and chemoattractant in vitro and induces vascular permeability and angiogenesis in vivo. VEGF is secreted by a wide variety of cancer cell types and promotes the growth of tumors by inducing the development of tumor-associated vasculature. Inhibition of VEGF function has been shown to limit both the growth of primary experimental tumors as well as the incidence of metastases in immunocompromised mice. Various dsRNAs directed to VEGF are described in co-pending U.S. Ser. Nos. 11/078,073 and 11/340,080, which are hereby incorporated by reference in their entirety.

As used herein, "transthyretin" ("TTR") refers to a gene in a cell. TTR is also known as ATTR, HsT2651, PALB, prealbumin, TBPA, and transthyretin (prealbumin, amyloidosis type I). The sequence of a human TTR mRNA transcript can be found at NM_000371. The sequence of mouse TTR mRNA can be found at NM_013697.2, and the sequence of rat TTR mRNA can be found at NM_012681.1.

As used herein, "GNAQ" refers to a G-alpha q subunit (GNAQ) of a heterotrimeric G gene. GNAQ is also known as guanine nucleotide binding protein (G protein), q polypeptide and G-ALPHA-q, GAQ. The sequence of a human GNAQ mRNA transcript can be found at NM_002072.2. The sequence of rat GNAQ mRNA can be found at NM_031036

As used herein, "target sequence" refers to a contiguous portion of the nucleotide sequence of an mRNA molecule formed during the transcription of the target gene of interest, including mRNA that is a product of RNA processing of a primary transcription product.

As used herein, "VSP" refers to the dual target of VEGF and Eg5/KSP.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide having the first nucleotide sequence to the oligonucleotide or polynucleotide having the second nucleotide sequence over the entire length of the first and second nucleotide sequences. Such sequences can be referred to as "fully complementary" with respect to each other. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA having one oligonucleotide 21 nucleotides in length and another oligonucleotide 23 nucleotides in length, wherein the longer oligonucleotide has a sequence of 21 nucleotides that is fully complementary to the shorter oligonucleotide, may yet be referred to as "fully complementary."

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide that is substantially complementary to a contiguous portion of the mRNA of interest (e.g., encoding a target gene) including a 5' UTR, an open reading frame (ORF), or a 3' UTR. For example, a polynucleotide is complementary to at least a part of a target mRNA if the sequence is substantially complementary to a non-interrupted portion of an mRNA encoding the target mRNA.

The term "double-stranded RNA" or "dsRNA", as used herein, refers a duplex structure comprising two anti-parallel and substantially complementary, as defined above, nucleic acid strands. In general, the majority of nucleotides of each strand are ribonucleotides, but as described in detail herein, each or both strands can also include at least one non-ribonucleotide, e.g., a deoxyribonucleotide and/or a modified nucleotide. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

The two strands forming the duplex structure may be different portions of one larger RNA molecule, or they may be separate RNA molecules. Where separate RNA molecules, such dsRNA are often referred to in the literature as siRNA ("short interfering RNA"). Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In general, the majority of nucleotides of each strand are ribonucleotides, but as described in detail herein, each or both strands can also include at least one non-ribonucleotide, e.g., a deoxyribonucleotide and/or a modified nucleotide. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. For clarity, chemical caps or non-nucleotide chemical moieties conjugated to the 3' end or 5' end of an siRNA are not considered in determining whether an siRNA has an overhang or is blunt ended.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally the most tolerated mismatches are in the terminal regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence," "inhibit the expression of," "down-regulate the expression of," "suppress the expression of," and the like, in as far as they refer to the target gene of interest, herein refer to the at least partial suppression of the expression of the target gene of interest, as manifested by a reduction of the amount of mRNA which may be isolated or detected from a first cell or group of cells in which the target gene of interest is transcribed and which has or have been treated such that the expression of the target gene of interest is inhibited, as compared to a second cell or group of cells substantially identical to the first cell or group of cells but which has or have not been so treated (control cells). The degree of inhibition is usually expressed in terms of $$\frac{(\text{mRNA in control cells}) - (\text{mRNA in treated cells})}{(\text{mRNA in control cells})} \cdot 100\%$$

Alternatively, the degree of inhibition may be given in terms of a reduction of a parameter that is functionally linked to target gene of interest expression, e.g. the amount of protein encoded by the target gene of interest which is produced by a cell, or the number of cells displaying a certain phenotype. In principle, target gene silencing can be determined in any cell expressing the target, either constitutively or by genomic engineering, and by any appropriate assay. However, when a reference is needed in order to determine whether a given dsRNA inhibits the expression of the target gene of interest by a certain degree and therefore is encompassed by the instant invention, the assays provided in the Examples below shall serve as such reference.

For example, in certain instances, expression of a target gene is suppressed by at least about 5%, 10%, 15%, 20%, 25%, 30%, 35%, 40%, 45%, or 50% by administration of the double-stranded oligonucleotide of the invention. In some embodiment, a target gene is suppressed by at least about 60%, 70%, or 80% by administration of the double-stranded oligonucleotide of the invention. In some embodiments, a target gene is suppressed by at least about 85%, 90%, or 95% by administration of the double-stranded oligonucleotide of the invention.

As used herein in the context of target gene expression, the terms "treat", "treatment", and the like, refer to relief from or alleviation of pathological processes which can be mediated by down regulating the target gene of interest. In the context of the present invention insofar as it relates to any of the other conditions recited herein below (other than pathological processes which can be mediated by down regulating the target gene of interest), the terms "treat", "treatment", and the like mean to relieve or alleviate at least one symptom associated with such condition, or to slow or reverse the progression of such condition. For example, in the context of hyperlipidemia and target gene PCSK9, treatment will involve a decrease in serum lipid levels.

As used herein, the phrases "therapeutically effective amount" and "prophylactically effective amount" refer to an amount that provides a therapeutic benefit in the treatment, prevention, or management of pathological processes that can be mediated by down regulating the target gene of interest or an overt symptom of pathological processes which can be mediated by down regulating the target gene of interest. The specific amount that is therapeutically effective can be readily determined by an ordinary medical practitioner, and may vary depending on factors known in the art, such as, e.g., the type of pathological processes that can be mediated by down regulating the target gene of interest, the patient's history and age, the stage of pathological processes that can be mediated by down regulating target gene of interest expression, and the administration of other anti-pathological processes that can be mediated by down regulating target gene of interest expression.

As used herein, a "pharmaceutical composition" includes a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof and are described in more detail below. The term specifically excludes cell culture medium.

As used herein, a "transformed cell" is a cell into which a vector has been introduced from which a dsRNA molecule may be expressed.

Methods for Increasing Efficacy of Lipid Formulated siRNAs

Disclosed herein are methods for increasing the efficacy, e.g., lowering the effective dose, of a lipid formulated siRNA targeting a gene of interest. The method includes administering an agent e.g., a statin or, e.g., a PCSK9 targeted siRNA, that increases LDL receptor (LDLR) levels before administration of the lipid formulated siRNA targeting a gene of interest.

The method utilizes any agent that increases LDLR levels. Examples include but are not limited to statins and estradiol. Other examples of agents that increase LDLR levels are well known to one of skill in the art. Examples of other agents are described in more detail below.

In other embodiments, the agent is an inhibitor of PCSK9 expression, e.g., a PCSK9 targeted siRNA. The examples below describe examples of PCSK9 targeted siRNAs. In one embodiment, the agent is an siRNA including at least 15 contiguous nucleotides of the antisense strand of AD-9680. In another embodiment, the agent is AD-9680. The agent is administered at a dose effective to increase LDLR levels. Dosage of, e.g., statins, are well know to one of skill in the art. Dosage of a PCSK9 targeted siRNA agent can be about 0.5 to 10 mg/kg. In some embodiments, the agent is a PCSK9 targeted siRNA agent administered at a dose of about 3 mg/kg.

The agent increases LDLR levels in the subject by 5 to 60%. In some embodiments, LDLR levels are increased by at least 1, 2, 3, 4, 5, 6, 7, 8, 9, 10, 11, 12, 13, 14, 15, 16, 17, 18, 19, 20, 25, 30, 35, 40, 45, 50, 55, or by at least 60%. In one embodiment, the method includes administration of an agent that increases LDLR levels by about 15%. The agent increases LDLR levels for at least 1, 2, 3, 4, 5, 7, 10, 14, 21, 25, 30 or 40 or more days.

The liposomal formulated siRNA targeting a gene of interest is administered after the agent, within 1, 2, 3, 4, 5, or 7, 10, 14, 21, 25, 30 or 40 or more days after the agent is administered, thereby inhibiting the expression of the target gene in a subject. In an embodiment, the siRNA is administered at the same time as the agent. In an embodiment, the siRNA is administered less than 1 day after the agent. In one embodiment, doses of dsRNA are administered not more than once every four weeks, not more than once every three weeks, not more than once every two weeks, or not more than once every week. In another embodiment, the administrations can be maintained for one, two, three, or six months, or one year or longer.

In another embodiment, administration of the siRNA can be provided when Low Density Lipoprotein cholesterol (LDLc) levels reach or surpass a predetermined minimal level, such as greater than 70 mg/dL, 130 mg/dL, 150 mg/dL, 200 mg/dL, 300 mg/dL, or 400 mg/dL.

The method is directed to increasing the efficiency, e.g., lowering the effective does of a lipid formulated siRNA targeting a gene of interest. Further discussions of lipid formulations are disclosed herein. In some embodiments the lipid formulation includes 2,2-Dilinoleyl-4-dimethylaminoethyl-[1,3]-dioxolane (XTC) or 1,2-Dilinolenyloxy-N,N-dimethylaminopropane (DLinDMA). Additional formulations that recruit ApoE to the cell surface are contemplated by the invention. The lipid formulation can include ApoE.

The lipid formulated siRNA targets a gene of interest. The gene targeted by the siRNA can be expressed in hepatocytes or skin cells or adrenal gland cells or muscle cells or kidney cells. In one embodiment, the target gene is expressed in hepatocytes. Exemplary target genes include VSP (VEGF; Eg5), TTR, PCSK-9, SCAP, S14, MIG12, APOC3, APOB, PNPLA3, Hepcidin, or a PCSK5 gene. In one embodiment, the target gene is a PCSK9 gene. In another embodiment the target gene is VSP, e.g., VEGF and Eg5/KSP. In a further embodiment the target gene is a TTR gene. Additional target gene information is described in more detail below. One of skill understands that experiments can be performed to identify effective siRNAs targeting additional genes of interest.

A detailed description of siRNA targeting a gene of interest is described below in the section "Double-stranded ribonucleic acid (dsRNA)."

Exemplary siRNA targeting a gene of interest can be found in the following U.S. published patent applications which are herein incorporated by reference for all purposes including for the purpose of providing sequences of sense and antisense strands of dsRNA (siRNA) targeting genes of interest: 2006-0094032, 2007-0281899, 2006-0166918, 2006-0217324, 2008-0015161, and U.S. Pat. No. 7,528,118. Also described in the incorporated patent applications are experiments and results for the design and screening of siRNA targeting the relevant target gene.

In some embodiments the target gene of interest is the PCSK9 gene, and the siRNA includes at least 15 contiguous nucleotides of the antisense strand of any of the duplexes described herein, e.g., AD-9680 described below. The siRNA can contain at least 15, 16, 17, 18, 19, 20, 21, 22, or 23 contiguous nucleotides of the antisense strand of AD-9680. In one embodiment, the method includes an siRNA having the antisense strand of AD-9680. In another embodiment the siRNA is the duplex AD-9680.

In one embodiment, the dsRNA does not activate the immune system, e.g., it does not increase cytokine levels, such as TNF-alpha or IFN-alpha levels. For example, when measured by an assay, such as an in vitro PBMC assay, such as described herein, the increase in levels of TNF-alpha or IFN-alpha, is less than 30%, 20%, or 10% of control cells treated with a control dsRNA, e.g., a dsRNA that does not target the gene of interest.

The methods and kits described herein are administered to any subject of interest, e.g., any mammal. The term "mammal" as used herein includes both humans and non-humans and includes but is not limited to humans, non-human primates, canines, felines, murines, bovines, equines, and porcines. In one aspect the subject is a mouse or rat or monkey or human. In another aspect the subject is a human subject. In some embodiments, the subject is a human in need of treatment for a disease correlated with expression of the targeted gene. For example, the methods can be used to treat diseases and conditions that can be modulated by down regulating PCSK9 gene expression, e.g., hyperlipidemia and other forms of lipid imbalance such as hypercholesterolemia, hypertriglyceridemia and the pathological conditions associated with these disorders such as heart and circulatory diseases. In some embodiments, a patient treated with a PCSK9 dsRNA is also administered a non-dsRNA therapeutic agent, such as an agent known to treat lipid disorders.

Dosages of the liposomal formulated, gene targeted siRNA are described in further detail herein. Using the methods of the invention, wherein an agent is administered to increase LDLR levels, the first effective dose of the neutral liposomal formulated, siRNA is 2-50 fold lower than dose administered without the agent. In some embodiments the first effective dose is lowered 1, 2, 3, 4, 5, 10, 15, 20, 25, 30, 35, 40, or 50 fold lower. In one embodiment the first effective dose of the neutral liposomal formulated siRNA is at least 2 fold lower than the dose administered without the agent. In another embodiment the first effective dose of the neutral liposomal formulated, siRNA is at least 10 fold lower than the dose administered without the agent.

The invention provides a method for inhibiting the expression of a target gene in a subject. For example, in certain instances, expression of the target gene is suppressed by at least about 5%, 10%, 15%, 20%, 25%, 30%, 35%, 40%, 45%, or 50% by administration of a siRNA. In some embodiments, the target gene is suppressed by at least about 60%, 70%, or 80% by administration of the siRNA. In some embodiments, the target gene is suppressed by at least about 85%, 90%, or 95% by administration of the siRNA. For example, the incorporated patent applications describing target genes and siRNAs that target target genes provide a wide range of values for inhibition of expression obtained in assays using various dsRNA molecules at various concentrations.

In some embodiments the liposomal formulated siRNA targets the PCSK9 gene and administration results in a decrease in LDLc (low density lipoprotein cholesterol) levels in the blood, and more particularly in the serum, of the mammal. In some embodiments, LDLc levels are decreased by at least 5%, 10%, 15%, 20%, 25%, 30%, 40%, 50%, or 60%, or more, as compared to pretreatment levels. In one aspect the siRNA targets a PCSK9 gene and the first effective dose results in maintenance of at least a 40% decrease in total cholesterol levels.

The method includes administering a composition containing a liposomal formulated dsRNA. When the organism to be treated is a mammal such as a human, the composition can be administered by any means known in the art and described in more detail herein including, but not limited to oral or parenteral routes, including intravenous, intramuscular, subcutaneous, transdermal, and airway (aerosol) administration. In some embodiments, the compositions are administered by intravenous infusion or injection.

In another embodiment, the method can include administration of a non-dsRNA therapeutic agent, such as an agent known to treat a condition associated with expression of the gene of interest. In one embodiment, the gene targeted dsRNA is administered to the patient, and then the non-dsRNA agent is administered to the patient (or vice versa). In another embodiment, the gene targeted dsRNA and the non-dsRNA therapeutic agent are administered at the same time.

For example, the gene of interest can be the PCSK9 gene, and the method can include administration of a non-dsRNA therapeutic for treatment of lipid disorders, such as hypercholesterolemia, atherosclerosis or dyslipidemia. For example, a PCSK9 targeted dsRNA of the invention can be administered with, e.g., an HMG-CoA reductase inhibitor (e.g., a statin).

In one embodiment, a dsRNA targeting PCSK9 is administered in combination with an ezetimibe/simvastatin combination (e.g., Vytorin® (Merck/Schering-Plough Pharmaceuticals)).

In another aspect, the invention features, a method of instructing an end user, e.g., a caregiver or a subject, on how to administer a dsRNA described herein. The method includes, optionally, providing the end user with one or more doses of the dsRNA, and instructing the end user to administer the dsRNA on a regimen described herein, thereby instructing the end user.

Agents

The invention includes the use of one or more agents that increase LDLR levels in a mammal. Examples include but are not limited to dsRNA (e.g., PCSK9 dsRNA), statins, and/or estradiol. Examples of agents can also include but are not limited to berberine, HMG CoA reductase inhibitors, squalene synthetase inhibitors, HMG CoA synthetase inhibitors, fenofibrates, LDLR RNAa, IDOL targeted siRNA, niacin, and ezetimibe. Other examples of agents that increase LDLR levels are well known to one of skill in the art.

An agent is administered at a dose effective in a mammal to increase LDLR levels. Dosage of, e.g., statins, are well know to one of skill in the art. Generally, one of skill in the art, e.g. a physician, can determine what the effective dose of a particular agent is based on the medical literature and the results of clinical trials. In an embodiment, the dosage of an agent is less than 0.1, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, or 55 or more mg/kg. Dosage of a PCSK9 targeted siRNA agent can be about 0.5 to 10 mg/kg. In some embodiments, the agent is a PCSK9 targeted siRNA agent administered at a dose of about 3 mg/kg.

In an embodiment, an agent can include: an HMG-CoA reductase inhibitor (e.g., a statin), a fibrate, a bile acid sequestrant, niacin, an antiplatelet agent, an angiotensin converting enzyme inhibitor, an angiotensin II receptor antagonist (e.g., losartan potassium, such as Merck & Co.'s Cozaar®), an acylCoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR) agonist, a gene-based therapy, a composite vascular protectant (e.g., AGI-1067, from Atherogenics), a glycoprotein IIb/IIIa inhibitor, aspirin or an aspirin-like compound, an IBAT inhibitor (e.g., S-8921, from Shionogi), a squalene synthase inhibitor, or a monocyte chemoattractant protein (MCP)-I inhibitor. Exemplary HMG-CoA reductase inhibitors include atorvastatin (Pfizer's Lipitor®/Tahor/Sortis/Torvast/Cardyl), pravastatin (Bristol-Myers Squibb's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis). Exemplary fibrates include, e.g., bezafibrate (e.g., Roche's Befizal®/Cedur®/Bezalip®, Kissei's Bezatol), clofibrate (e.g., Wyeth's Atromid-S®), fenofibrate (e.g., Fournier's Lipidil/Lipantil, Abbott's Tricor®, Takeda's Lipantil, generics), gemfibrozil (e.g., Pfizer's Lopid/Lipur) and ciprofibrate (Sanofi-Synthelabo's Modalim®). Exemplary bile acid sequestrants include, e.g., cholestyramine (Bristol-Myers Squibb's Questran® and Questran Light™), colestipol (e.g., Pharmacia's Colestid), and colesevelam (Genzyme/Sankyo's WelChol™). Exemplary niacin therapies include, e.g., immediate release formulations, such as Aventis' Nicobid, Upsher-Smith's Niacor, Aventis' Nicolar, and Sanwakagaku's Perycit. Niacin extended release formulations include, e.g., Kos Pharmaceuticals' Niaspan and Upsher-Smith's SIo-Niacin. Exemplary antiplatelet agents include, e.g., aspirin (e.g., Bayer's aspirin), clopidogrel (Sanofi-Synthelabo/Bristol-Myers Squibb's Plavix), and ticlopidine (e.g., Sanofi-Synthelabo's Ticlid and Daiichi's Panaldine). Other aspirin-like compounds useful in combination with a dsRNA include, e.g., Asacard (slow-release aspirin, by Pharmacia) and Pamicogrel (Kanebo/Angelini Ricerche/CEPA). Exemplary angiotensin-converting enzyme inhibitors include, e.g., ramipril (e.g., Aventis' Altace) and enalapril (e.g., Merck & Co.'s Vasotec). Exemplary acyl CoA cholesterol acetyltransferase (ACAT) inhibitors include, e.g., avasimibe (Pfizer), eflucimibe (BioMérieux Pierre Fabre/Eli Lilly), CS-505 (Sankyo and Kyoto), and SMP-797 (Sumito). Exemplary cholesterol absorption inhibitors include, e.g., ezetimibe (Merck/Schering-Plough Pharmaceuticals Zetia®) and Pamaqueside (Pfizer). Exemplary CETP inhibitors include, e.g., Torcetrapib (also called CP-529414, Pfizer), JTT-705 (Japan Tobacco), and CETi-I (Avant Immunotherapeutics). Exemplary microsomal triglyceride transfer protein (MTTP) inhibitors include, e.g., implitapide (Bayer), R-103757 (Janssen), and CP-346086 (Pfizer). Other exemplary cholesterol modulators include, e.g., NO-1886 (Otsuka/TAP Pharmaceutical), CI-1027 (Pfizer), and WAY-135433 (Wyeth-Ayerst). Exemplary bile acid modulators include, e.g., HBS-107 (Hisamitsu/Banyu), Btg-511 (British Technology Group), BARI-1453 (Aventis), S-8921 (Shionogi), SD-5613 (Pfizer), and AZD-7806 (AstraZeneca). Exemplary peroxisome proliferation activated receptor (PPAR) agonists include, e.g., tesaglitazar (AZ-242) (AstraZeneca), Netoglitazone (MCC-555) (Mitsubishi/Johnson & Johnson), GW-409544 (Ligand Pharmaceuticals/GlaxoSmithKline), GW-501516 (Ligand Pharmaceuticals/GlaxoSmithKline), LY-929 (Ligand Pharmaceuticals and Eli Lilly), LY-465608 (Ligand Pharmaceuticals and Eli Lilly), LY-518674 (Ligand Pharmaceuticals and Eli Lilly), and MK-767 (Merck and Kyorin). Exemplary gene-based therapies include, e.g., AdGWEGF121.10 (Gen- Vec), ApoAl (UCB Pharma/Groupe Fournier), EG-004 (Trinam) (Ark Therapeutics), and ATP-binding cassette transporter-Al (ABCAl) (CV Therapeutics/Incyte, Aventis, Xenon). Exemplary Glycoprotein IIb/IIIa inhibitors include, e.g., roxifiban (also called DMP754, Bristol-Myers Squibb), Gantofiban (Merck KGaA/Yamanouchi), and Cromafiban (Millennium Pharmaceuticals). Exemplary squalene synthase inhibitors include, e.g., BMS-1884941 (Bristol-Myers Squibb), CP-210172 (Pfizer), CP-295697 (Pfizer), CP-294838 (Pfizer), and TAK-475 (Takeda). An exemplary MCP-I inhibitor is, e.g., RS-504393 (Roche Bioscience). The anti-atherosclerotic agent BO-653 (Chugai Pharmaceuticals), and the nicotinic acid derivative Nyclin (Yamanouchi Pharmaceuticals) are also appropriate for administering in combination with a dsRNA featured in the invention. Exemplary combination therapies suitable for administration with a dsRNA include, e.g., advicor (Niacin/lovastatin from Kos Pharmaceuticals), amlodipine/atorvastatin (Pfizer), and ezetimibe/simvastatin (e.g., Vytorin® 10/10, 10/20, 10/40, and 10/80 tablets by Merck/Schering-Plough Pharmaceuticals). Agents for treating hypercholesterolemia, and suitable for administration in combination with a dsRNA include, e.g., lovastatin, niacin Altoprev® Extended-Release Tablets (Andrx Labs), lovastatin Caduet® Tablets (Pfizer), amlodipine besylate, atorvastatin calcium Crestor® Tablets (AstraZeneca), rosuvastatin calcium Lescol® Capsules (Novartis), fluvastatin sodium Lescol® (Reliant, Novartis), fluvastatin sodium Lipitor® Tablets (Parke-Davis), atorvastatin calcium Lofibra® Capsules (Gate), Niaspan Extended-Release Tablets (Kos), niacin Pravachol Tablets (Bristol-Myers Squibb), pravastatin sodium TriCor® Tablets (Abbott), fenofibrate Vytorin® 10/10 Tablets (Merck/Schering-Plough Pharmaceuticals), ezetimibe, simvastatin WelChol™ Tablets (Sankyo), colesevelam hydrochloride Zetia® Tablets (Schering), ezetimibe Zetia® Tablets (Merck/Schering-Plough Pharmaceuticals), and ezetimibe Zocor® Tablets (Merck).

Double-Stranded Ribonucleic Acid (dsRNA)

As described in more detail herein, the invention provides methods for administration of double-stranded ribonucleic acid (dsRNA) molecules for inhibiting the expression of a target gene in a subject. The dsRNA includes an antisense strand having a region of complementarity that is complementary to at least a part of an mRNA formed in the expression of the target gene, and the region of complementarity is less than 30 nucleotides in length, generally 19-24 nucleotides in length. The dsRNA, upon contact with a cell expressing the target gene, inhibits the expression of said target gene, e.g., as measured such as by an assay described herein. The dsRNA of the invention can further include one or more single-stranded nucleotide overhangs.

As described herein, the agent used in the methods of the invention can also be a dsRNA, e.g., an siRNA targeting PCSK9.

The dsRNA can be synthesized by standard methods known in the art as further discussed below, e.g., by use of an automated DNA synthesizer, such as are commercially available from, for example, Biosearch, Applied Biosystems, Inc.

The dsRNA includes two nucleic acid strands that are sufficiently complementary to hybridize to form a duplex structure. One strand of the dsRNA (the antisense strand) can have a region of complementarity that is substantially complementary, and generally fully complementary, to a target sequence, derived from the sequence of an mRNA formed during the expression of the target gene. The other strand (the sense strand) includes a region that is complementary to the antisense strand, such that the two strands hybridize and form a duplex structure when combined under suitable conditions.

Generally, the duplex structure is between 15 and 30, or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ. In one embodiment the region of complementarity is 19 nucleotides in length.

Each strand of the dsRNA of invention is generally between 15 and 30, or between 18 and 25, or 18, 19, 20, 21, 22, 23, 24, or 25 nucleotides in length. In other embodiments, each is strand is 25-30 nucleotides in length. Each strand of the duplex can be the same length or of different lengths. When two different siRNAs are used in combination, the lengths of each strand of each siRNA can be identical or can differ.

The dsRNA of the invention can include one or more single-stranded overhang(s) of one or more nucleotides. In one embodiment, at least one end of the dsRNA has a single-stranded nucleotide overhang of 1 to 4, generally 1 or 2 nucleotides. In another embodiment, the antisense strand of the dsRNA has 1-10 nucleotides overhangs each at the 3' end and the 5' end over the sense strand. In further embodiments, the sense strand of the dsRNA has 1-10 nucleotides overhangs each at the 3' end and the 5' end over the antisense strand. In one embodiment, the dsRNA includes a 2 nucleotide overhang at the 3' end of each strand.

A dsRNAs having at least one nucleotide overhang can have unexpectedly superior inhibitory properties than the blunt-ended counterpart. In some embodiments the presence of only one nucleotide overhang strengthens the interference activity of the dsRNA, without affecting its overall stability. Generally, single-stranded overhangs are located at the 3'-terminal end of the antisense strand or, alternatively, at the 3'-terminal end of the sense strand. The dsRNA can also have a blunt end, generally located at the 5'-end of the antisense strand. Such dsRNAs can have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

The dsRNA of the invention can contain one or more mismatches to the target sequence. In one embodiment, the dsRNA of the invention contains no more than 1, no more than 2, or no more than 3 mismatches. In one embodiment, the antisense strand of the dsRNA contains mismatches to the target sequence, and the area of mismatch is not located in the center of the region of complementarity. In another embodiment, the antisense strand of the dsRNA contains mismatches to the target sequence and the mismatch is restricted to 5 nucleotides from either end, for example 5, 4, 3, 2, or 1 nucleotide from either the 5' or 3' end of the region of complementarity. For example, for a 23 nucleotide dsRNA strand which is complementary to a region of the target gene, the dsRNA does not contain any mismatch within the central 13 nucleotides. The methods described within the invention can be used to determine whether a dsRNA containing a mismatch to a target sequence is effective in inhibiting the expression of the target gene. Consideration of the efficacy of dsRNAs with mismatches in inhibiting expression of the target gene is important, especially if the particular region of complementarity in the target gene is known to have polymorphic sequence variation within the population.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In embodiments, the dsRNAs of the invention can include at least one strand of a length described herein. In another embodiment, it can be reasonably expected that shorter dsRNAs minus only a few nucleotides on one or both ends may be similarly effective as compared to the 21 nt dsRNAs. Hence, dsRNAs having a partial sequence of at least 15, 16, 17, 18, 19, 20, or more contiguous nucleotides and differing in their ability to inhibit the expression of the target gene by not more than 5, 10, 15, 20, 25, or 30% inhibition from a dsRNA comprising the full 21 nt sequence, are contemplated by the invention. Further dsRNAs that cleave within the target sequence of a target gene can readily be made using the target gene sequence and the target sequence provided.

In addition, an identified dsRNA identifies a site in the target mRNA that is susceptible to RNAi based cleavage. As such the present invention further includes other dsRNA that target within the sequence targeted by one of the dsRNA of the present invention. As used herein a second dsRNA is said to target within the sequence of a first dsRNA if the second dsRNA cleaves the message anywhere within the mRNA that is complementary to the antisense strand of the first dsRNA.

Target Genes and dsRNA

The methods described herein use a lipid formulated dsRNA targeting a gene of interest (i.e. a target gene). In an embodiment, the gene targeted by the dsRNA can be expressed in hepatocytes or skin cells or adrenal gland cells or muscle cells or kidney cells. In one embodiment, the target gene is expressed in hepatocytes. Example target genes include but are not limited to VSP (VEGF and Eg5/KSP), TTR, PCSK9, GNAQ, HTT, SCAP, S14, MIG12, APOC3, APOB, PNPLA3, Hepcidin, or PCSK5.

In an embodiment, the target gene is a PCSK9 gene. Exemplary dsRNA targeting PCSK9 can be found in the following U.S. published patent applications and/or U.S. patents which are herein incorporated by reference for all purposes including for the purpose of providing sequences of sense and antisense strands of dsRNA (e.g., siRNA) targeting the gene of interest: Ser. Nos. 12/554,231; 12/478,452; and U.S. Pat. No. 7,605,251. Also described in the incorporated patents and/or patent applications are experiments and results for the design and screening of dsRNAs targeting the gene of interest.

In some embodiments the target gene of interest is the PCSK9 gene, and the dsRNA includes at least 15 contiguous nucleotides of the antisense strand of any of the duplexes described in the relevant patents and patent applications described above. In some embodiments, the dsRNA includes at least 15 contiguous nucleotides of the sense strand of any of the duplexes described in the relevant patents and patent applications described above. In an embodiment, the dsRNA can contain at least 15, 16, 17, 18, 19, 20, 21, 22, or 23 contiguous nucleotides of the nucleotide sequence of the antisense strand of AD-9680 (AAGCAAAACAGGUCUA-GAATT) (SEQ ID NO:1). In an embodiment, the dsRNA can contain at least 15, 16, 17, 18, 19, 20, 21, 22, or 23 contiguous nucleotides of the nucleotide sequence of the sense strand of AD-9680 (UUCUAGACCUGUUUUGCUUTT) (SEQ ID NO:2). In another embodiment the siRNA is the duplex AD-9680. In an embodiment, the dsRNA can contain at least 15, 16, 17, 18, 19, 20, 21, 22, or 23 contiguous nucleotides of the nucleotide sequence of the antisense strand of AD-10792 (UUCCGAAUAAACUCCAGGCTT) (SEQ ID NO:3). In an embodiment, the dsRNA can contain at least 15, 16, 17, 18, 19, 20, 21, 22, or 23 contiguous nucleotides of the nucleotide sequence of the sense strand of AD-10792 (GCCUGGAGU-UUAUUCGGAATT) (SEQ ID NO:4). In another embodiment the siRNA is the duplex AD-10792.

In an embodiment, the target gene is an Eg5 gene. Exemplary dsRNA targeting Eg5 can be found in the following U.S. published patent applications and/or U.S. patents which are herein incorporated by reference for all purposes including for the purpose of providing sequences of sense and antisense strands of dsRNA (e.g., siRNA) targeting the gene of interest: U.S. Pat. No. 7,718,629; Ser. Nos. 12/754,110; 12/552,207; and 12/723,471. Also described in the incorporated patents and/or patent applications are experiments and results for the design and screening of dsRNAs targeting the gene of interest.

In some embodiments the target gene of interest is the Eg5 gene, and the dsRNA includes at least 15 contiguous nucleotides of the antisense strand of any of the duplexes described in the relevant patents and patent applications described above. In some embodiments, the dsRNA includes at least 15 contiguous nucleotides of the sense strand of any of the duplexes described in the relevant patents and patent applications described above. In an embodiment, the dsRNA can contain at least 15, 16, 17, 18, 19, 20, 21, 22, or 23 contiguous nucleotides of the nucleotide sequence of the antisense strand of AD12115 (AGUUAGUUUAGAUUCUCGATT) (SEQ ID NO:5). In an embodiment, the dsRNA can contain at least 15, 16, 17, 18, 19, 20, 21, 22, or 23 contiguous nucleotides of the nucleotide sequence of the sense strand of AD12115 (UC-GAGAAUCUAAACUAACUTT) (SEQ ID NO:6). In another embodiment the siRNA is the duplex AD12115.

In an embodiment, the target gene is a VEGF gene. Exemplary dsRNA targeting VEGF can be found in the following U.S. published patent applications and/or U.S. patents which are herein incorporated by reference for all purposes including for the purpose of providing sequences of sense and antisense strands of dsRNA (e.g., siRNA) targeting the gene of interest: Ser. Nos. 11/078,073; 11/340,080; 11/694,215; and 12/754,110. Also described in the incorporated patents and/or patent applications are experiments and results for the design and screening of dsRNAs targeting the gene of interest.

In some embodiments the target gene of interest is the VEGF gene, and the dsRNA includes at least 15 contiguous nucleotides of the antisense strand of any of the duplexes described in the relevant patents and patent applications described above. In some embodiments, the dsRNA includes at least 15 contiguous nucleotides of the sense strand of any of the duplexes described in the relevant patents and patent applications described above. In an embodiment, the dsRNA can contain at least 15, 16, 17, 18, 19, 20, 21, 22, or 23 contiguous nucleotides of the nucleotide sequence of the antisense strand of AL-DP-4094 (GUCGUGUAUCCUCUC-UACUCGAA) (SEQ ID NO:7). In an embodiment, the dsRNA can contain at least 15, 16, 17, 18, 19, 20, 21, 22, or 23 contiguous nucleotides of the nucleotide sequence of the sense strand of AL-DP-4094 (GCACAUAG-GAGAGAUGAGCUU) (SEQ ID NO:8). In another embodiment the siRNA is the duplex AL-DP-4094.

In one embodiment, the target gene is both VEGF and Eg5/KSP, e.g., VSP. The lipid formulated dsRNA includes two dsRNAs. Exemplary sense and antisense sequences are described herein, e.g., duplex AD-12115 targeting Eg5/KSP and AL-DP-4094 targeting VEGF.

In an embodiment, the target gene is a TTR gene. Exemplary dsRNA targeting TTR can be found in the following U.S. published patent applications and/or U.S. patents which are herein incorporated by reference for all purposes including for the purpose of providing sequences of sense and antisense strands of dsRNA (e.g., siRNA) targeting the gene of interest: Ser. No. 12/582,669. Also described in the incorporated patents and/or patent applications are experiments and results for the design and screening of dsRNAs targeting the gene of interest.

In some embodiments the target gene of interest is the TTR gene, and the dsRNA includes at least 15 contiguous nucleotides of the antisense strand of any of the duplexes described in the relevant patents and patent applications described above. In some embodiments, the dsRNA includes at least 15 contiguous nucleotides of the sense strand of any of the duplexes described in the relevant patents and patent applications described above. In an embodiment, the dsRNA can contain at least 15, 16, 17, 18, 19, 20, 21, 22, or 23 contiguous nucleotides of the nucleotide sequence of the antisense strand of AD-18328 (AUGGAAUACUCUUGGUUAC) (SEQ ID NO:9). In an embodiment, the dsRNA can contain at least 15, 16, 17, 18, 19, 20, 21, 22, or 23 contiguous nucleotides of the nucleotide sequence of the sense strand of AD-18328 (GUAACCAAGAGUAUUCCAU) (SEQ ID NO:10). In another embodiment the siRNA is the duplex AD-18328.

In an embodiment, the target gene is a GNAQ gene. Exemplary dsRNA targeting GNAQ can be found in the following U.S. published patent applications and/or U.S. patents which are herein incorporated by reference for all purposes including for the purpose of providing sequences of sense and antisense strands of dsRNA (e.g., siRNA) targeting the gene of interest: Ser. No. 12/635,630. Also described in the incorporated patents and/or patent applications are experiments and results for the design and screening of dsRNAs targeting the gene of interest.

In some embodiments the target gene of interest is the GNAQ gene, and the dsRNA includes at least 15 contiguous nucleotides of the antisense strand of any of the duplexes described in the relevant patents and patent applications described above. In some embodiments, the dsRNA includes at least 15 contiguous nucleotides of the sense strand of any of the duplexes described in the relevant patents and patent applications described above. In an embodiment, the dsRNA can contain at least 15, 16, 17, 18, 19, 20, 21, 22, or 23 contiguous nucleotides of the nucleotide sequence of the antisense strand of AD-20057 (AUUAGUAUUAUGCAAA-UUG) (SEQ ID NO:11). In an embodiment, the dsRNA can contain at least 15, 16, 17, 18, 19, 20, 21, 22, or 23 contiguous nucleotides of the nucleotide sequence of the sense strand of AD-20057 (CAAUUUGCAUAAUACUAAU) (SEQ ID NO:12). In another embodiment the siRNA is the duplex AD-20057.

In an embodiment, the target gene is a HTT gene. Exemplary dsRNA targeting HTT can be found in the following U.S. published patent applications and/or U.S. patents which are herein incorporated by reference for all purposes including for the purpose of providing sequences of sense and antisense strands of dsRNA (e.g., siRNA) targeting the gene of interest: U.S. Pat. No. 7,662,797; Ser. Nos. 11/588,674; and 12/417,502. Also described in the incorporated patents and/or patent applications are experiments and results for the design and screening of dsRNAs targeting the gene of interest.

In some embodiments the target gene of interest is the HTT gene, and the dsRNA includes at least 15 contiguous nucleotides of the antisense strand of any of the duplexes described in the relevant patents and patent applications described above. In some embodiments, the dsRNA includes at least 15 contiguous nucleotides of the sense strand of any of the duplexes described in the relevant patents and patent applications described above. In an embodiment, the dsRNA can contain at least 15, 16, 17, 18, 19, 20, 21, 22, or 23 contiguous nucleotides of the nucleotide sequence of the antisense strand of AL-DP-5997 (cugcacgguucuuugugacTT) (SEQ ID NO:13). In an embodiment, the dsRNA can contain at least 15, 16, 17, 18, 19, 20, 21, 22, or 23 contiguous nucleotides of the nucleotide sequence of the sense strand of AL-DP-5997 (gucacaaagaaccgugcagTT) (SEQ ID NO:14). In another embodiment the siRNA is the duplex AL-DP-5997.

In an embodiment, the target gene is a ApoB gene. Exemplary dsRNA targeting ApoB can be found in the following U.S. published patent applications and/or U.S. patents which are herein incorporated by reference for all purposes including for the purpose of providing sequences of sense and antisense strands of dsRNA (e.g., siRNA) targeting the gene of interest: U.S. Pat. No. 7,528,118; Ser. Nos. 12/400,744; and 12/728,139. Also described in the incorporated patents and/or patent applications are experiments and results for the design and screening of dsRNAs targeting the gene of interest.

In some embodiments the target gene of interest is the ApoB gene, and the dsRNA includes at least 15 contiguous nucleotides of the antisense strand of any of the duplexes described in the relevant patents and patent applications described above. In some embodiments, the dsRNA includes at least 15 contiguous nucleotides of the sense strand of any of the duplexes described in the relevant patents and patent applications described above. In an embodiment, the dsRNA can contain at least 15, 16, 17, 18, 19, 20, 21, 22, or 23 contiguous nucleotides of the nucleotide sequence of the antisense strand of RNA agent number 35 (gaauggacaggu-caaucaaucuu) (SEQ ID NO:15). In an embodiment, the dsRNA can contain at least 15, 16, 17, 18, 19, 20, 21, 22, or 23 contiguous nucleotides of the nucleotide sequence of the sense strand of RNA agent number 35 (gauugauugaccuguc-cauuc) (SEQ ID NO:16). In another embodiment the siRNA is the duplex RNA agent number 35.

Modifications

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Preferred modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other certain dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, an dsRNA mimetic that has been shown to have excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Other embodiments of the invention are dsRNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy(2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples herein below.

Other preferred modifications include 2'-methoxy(2'-$OCH_3$), 2'-aminopropoxy(2'-$OCH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

dsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2 degree. C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Other nucleotide substitutions, such as "Universal" bases can be incorporated into siRNA duplexes to increase the number of target sequences any particular siRNA might have complementarity to and activity against. Universal bases are non-canonical synthetic molecules that mimic structures of traditional nucleotides (the genetic building blocks of DNA and RNA). However, instead of selectively pairing according to Watson/Crick rules (A with T or U, C with G), universal bases 'stack' equally well with all natural bases. Incorporating universal bases into siRNAs may enable the siRNA to tolerate a mutation at that specific site in its target mRNA. Thus, by decreasing the need for absolute complementarity between siRNA and its mRNA target, universal-base containing siRNAs may be an approach to (1) prevent drug resistance caused by site-specific viral mutations and (2) create siRNAs able to be broadly reactive across viral species with similar, but not absolutely conserved, targets. Among the modifications that can be used as universal bases are: 3-Nitropyrrole, 5-Nitroindole, Imidazole-4-Carboxamide, 2,4-difluorotoluoyl, and Inosine.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, each of which is herein incorporated by reference, and U.S. Pat. No. 5,750,692, also herein incorporated by reference.

Conjugates

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-5-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937). Preferred conjugates will assist in targeting cells. Such conjugates include, but are not limited to, mannose and folate conjugates.

Representative U.S. patents that teach the preparation of such dsRNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Synthesis

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In one embodiment, the oligonucleotides or linked nucleosides featured in the invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group. A summary listing of some of the oligonucleotide modifications known in the art is found at, for example, PCT Publication WO 200370918.

In some embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydroxysuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In one embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative U.S. patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Examples of modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate. The use of a cholesterol conjugate is particularly preferred since such a moiety can increase targeting liver cells, a site of target expression.

Vector Encoded dsRNA Agents

In another aspect of the invention, target gene specific dsRNA molecules that modulate target gene expression activity are expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., Proc. Natl. Acad. Sci. USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In one embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., Curr. Topics Micro. Immunol. (1992) 158:97-129)); adenovirus (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into many different cell types, including epithelial cells, in vitro and/or in vivo (see, e.g., Eglitis, et al., Science (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the dsRNA molecule(s) to be expressed can be used, for example vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentivirral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), *J Virol* 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; Anderson W F (1998), *Nature* 392: 25-30; and Rubinson D A et al., *Nat. Genet.* 33: 401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector having, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20: 1006-1010.

Suitable AAV vectors for expressing the dsRNA of the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or generally RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single target gene or multiple target genes over a period of a week or more are also contemplated by the invention. Successful introduction of the vectors of the invention into host cells can be monitored using various known methods. For example, transient transfection. can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The target specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Pharmaceutical Compositions

In one embodiment, the invention provides pharmaceutical compositions containing a dsRNA, as described herein, and a pharmaceutically acceptable carrier and methods of administering the same. The pharmaceutical composition containing the dsRNA is useful for treating a disease or disorder associated with the expression or activity of a target gene, such as pathological processes mediated by target gene expression. Such pharmaceutical compositions are formulated based on the mode of delivery. In an embodiment, the invention provides pharmaceutical compositions having an agent, as described herein, and a pharmaceutically acceptable carrier and methods of administering the same. In an embodiment, the invention provides pharmaceutical compositions having a dsRNA and an agent, as described herein, and a pharmaceutically acceptable carrier and methods of administering the same.

Dosage

The pharmaceutical compositions featured herein are administered in dosages sufficient to inhibit expression of target genes. In general, a suitable dose of dsRNA will be in the range of 0.01 to 200.0 milligrams per kilogram body weight of the recipient per day, generally in the range of 1 to 50 mg per kilogram body weight per day. For example, the dsRNA can be administered at 0.01 mg/kg, 0.05 mg/kg, 0.5 mg/kg, 1 mg/kg, 1.5 mg/kg, 2.0 mg/kg, 3.0 mg/kg, 5.0 mg/kg, 10 mg/kg, 20 mg/kg, 30 mg/kg, 40 mg/kg, or 50 mg/kg per single dose.

In another embodiment, the dosage is between 0.01 and 0.2 mg/kg. For example, the dsRNA can be administered at a dose of 0.01 mg/kg, 0.02 mg/kg, 0.03 mg/kg, 0.04 mg/kg, 0.05 mg/kg, 0.06 mg/kg, 0.07 mg/kg 0.08 mg/kg 0.09 mg/kg, 0.10 mg/kg, 0.11 mg/kg, 0.12 mg/kg, 0.13 mg/kg, 0.14 mg/kg, 0.15 mg/kg, 0.16 mg/kg, 0.17 mg/kg, 0.18 mg/kg, 0.19 mg/kg, or 0.20 mg/kg.

In one embodiment, the dosage is between 0.2 mg/kg and 1.5 mg/kg. For example, the dsRNA can be administered at a dose of 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, or 1.5 mg/kg.

The dsRNA can be administered at a dose of 0.03, 0.1, 0.3, or 1.3, or 3.0 mg/kg.

The pharmaceutical composition can be administered once daily, or the dsRNA may be administered as two, three, or more sub-doses at appropriate intervals throughout the day. The effect of a single dose on target mRNA levels is long lasting, such that subsequent doses are administered at not more than 7 day intervals, or at not more than 1, 2, 3, or 4 week intervals.

In one embodiment the lipid formulated mRNA targeted dsRNA is administered at a first dose of about 3 mg/kg followed by administering at least one subsequent dose once a week, wherein the subsequent dose is lower than the first dose, e.g., the subsequent dose is about 1.0 mg/kg or about 0.3 mg/kg. The subsequent dose can be administered, e.g., once a week for four weeks. In some embodiments the dsRNA is administered using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by target gene expression. Such models are used for in vivo testing of dsRNA, as well as for determining a therapeutically effective dose. A suitable mouse model is, for example, a mouse containing a plasmid expressing a human target gene. Another suitable mouse model is a transgenic mouse carrying a transgene that expresses a human target gene.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately to determine useful doses in humans. Levels in plasma may be measured, for example, by high performance liquid chromatography.

In addition to their administration, as discussed above, the dsRNAs featured in the invention can be administered in combination with other known agents effective in treatment of pathological processes mediated by target gene expression. In any event, the administering physician can adjust the amount and timing of dsRNA administration on the basis of results observed using standard measures of efficacy known in the art or described herein.

Administration

The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, and subdermal, oral or parenteral, e.g., subcutaneous.

For example, when treating a mammal with hyperlipidemia, the dsRNA molecules are administered systemically via parental means. Parenteral administration includes intravenous, intra-arterial, subcutaneous, intraperitoneal or intramuscular injection or infusion; or intracranial, e.g., intraparenchymal, intrathecal or intraventricular, administration. For example, dsRNAs, conjugated or unconjugated or formulated with or without liposomes, can be administered intravenously to a patient. For such, a dsRNA molecule can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. For parenteral, intrathecal, or intraventricular administration, a dsRNA molecule can be formulated into compositions such as sterile aqueous solutions, which also can contain buffers, diluents, and other suitable additives (e.g., penetration enhancers, carrier compounds, and other pharmaceutically acceptable carriers). Formulations are described in more detail herein.

The dsRNA can be delivered in a manner to target a particular tissue, such as the liver (e.g., the hepatocytes of the liver).

Formulations

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. In one aspect are formulations that target the liver when treating hepatic disorders such as hyperlipidemia.

In addition, dsRNA that target the target gene can be formulated into compositions containing the dsRNA admixed, encapsulated, conjugated, or otherwise associated with other molecules, molecular structures, or mixtures of nucleic acids. For example, a composition containing one or more dsRNA agents that target the target gene can contain other therapeutic agents, such as other cancer therapeutics or one or more dsRNA compounds that target other target genes.

Oral, Parenteral, Topical, and Biologic Formulations

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. dsRNAs featured in the invention may be delivered orally, in granular form including sprayed dried particles, or complexed to form micro or nanoparticles. dsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, U.S. Patent Publication. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). dsRNAs featured in the invention may be encapsulated within liposomes or may form complexes thereto. Alternatively, dsRNAs may be complexed to lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference. In addition, dsRNA molecules can be administered to a mammal as biologic or abiologic means as described in, for example, U.S. Pat. No. 6,271,359. Abiologic delivery can be accomplished by a variety of methods including, without limitation, (1) loading liposomes with a dsRNA acid molecule provided herein and (2) complexing a dsRNA molecule with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin™ (Invitrogen/Life Technologies, Carlsbad, Calif.) and Effectene™ (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (Nature Biotechnology, 15: 647-652 (1997)) can be used. In other embodiments, polycations such as polyethyleneimine can be used to achieve delivery in vivo and ex vivo (Boletta et al., J. Am. Soc. Nephrol. 7: 1728 (1996)). Additional information regarding the use of liposomes to deliver nucleic acids can be found in U.S. Pat. No. 6,271,359, PCT Publication WO 96/40964 and Morrissey, D. et al. 2005. Nat. Biotechnol. 23(8):1002-7.

Biologic delivery can be accomplished by a variety of methods including, without limitation, the use of viral vectors. For example, viral vectors (e.g., adenovirus and herpes virus vectors) can be used to deliver dsRNA molecules to liver cells. Standard molecular biology techniques can be used to introduce one or more of the dsRNAs provided herein into one of the many different viral vectors previously developed to deliver nucleic acid to cells. These resulting viral vectors can be used to deliver the one or more dsRNAs to cells by, for example, infection.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include: liposomes obtained from natural phospholipids are biocompatible and biodegradable; liposomes can incorporate a wide range of water and lipid soluble drugs; and liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al., S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes, it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a dsRNA featured in the invention (e.g., a dsRNA targeting a gene of interest or, e.g., an agent such as a dsRNA targeting PCSK9) is fully encapsulated in the lipid formulation, e.g., to form a nucleic acid lipid panicle. Nucleic acid-lipid particles typically contain a cationic lipid, a non-cationic lipid, a sterol, and a lipid that prevents aggregation of the particle (e.g., a PEG-lipid conjugate). Nucleic acid-lipid particles are extremely useful for systemic applications, as they exhibit extended circulation lifetimes following intravenous (i.v.) injection and accumulate at distal sites (e.g., sites physically separated from the administration site). In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

Nucleic acid-lipid particles can further include one or more additional lipids and/or other components such as cholesterol. Other lipids may be included in the liposome compositions for a variety of purposes, such as to prevent lipid oxidation or to attach ligands onto the liposome surface. Any of a number of lipids may be present, including amphipathic, neutral, cationic, and anionic lipids. Such lipids can be used alone or in combination. Specific examples of additional lipid components that may be present are described herein.

Additional components that may be present in a nucleic acid-lipid particle include bilayer stabilizing components such as polyamide oligomers (see, e.g., U.S. Pat. No. 6,320,017), peptides, proteins, detergents, lipid-derivatives, such as PEG coupled to phosphatidylethanolamine and PEG conjugated to ceramides (see, U.S. Pat. No. 5,885,613).

A nucleic acid-lipid particle can include one or more of a second amino lipid or cationic lipid, a neutral lipid, a sterol, and a lipid selected to reduce aggregation of lipid particles during formation, which may result from steric stabilization of particles which prevents charge-induced aggregation during formation.

Nucleic acid-lipid particles include, e.g., a SPLP, pSPLP, and SNALP. The term"SNALP" refers to a stable nucleic acid-lipid particle, including SPLP. The term "SPLP" refers to a nucleic acid-lipid particle comprising plasmid DNA encapsulated within a lipid vesicle. SPLPs include "pSPLP," which include an encapsulated condensing agent-nucleic acid complex as set forth in PCT Publication No. WO 00/03683.

The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1, or about 6:1, 7:1, 8:1, 9:1, 10:1, 11:1, 12:1, or 33:1.

Cationic Lipids

Cationic lipids can include ionizable cationic lipids and non-ionizable cationic lipids. A cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALNY-100), (6Z,9Z,28Z,31Z)-heptatriaconta-6,9,28,31-tetraen-19-yl 4-(dimethylamino)butanoate (MC3), or a mixture thereof.

Other cationic lipids, which carry a net positive charge at about physiological pH, in addition to those specifically described above, may also be included in lipid particles of the invention. Such cationic lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

As used herein, the term "amino lipid" is meant to include those lipids having one or two fatty acid or fatty alkyl chains and an amino head group (including an alkylamino or dialkylamino group) that may be protonated to form a cationic lipid at physiological pH.

Other amino lipids would include those having alternative fatty acid groups and other dialkylamino groups, including those in which the alkyl substituents are different (e.g., N-ethyl-N-methylamino-, N-propyl-N-ethylamino- and the like). For those embodiments in which $R^{11}$ and $R^{12}$ are both long chain alkyl or acyl groups, they can be the same or different. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ are preferred. Other scaffolds can also be used to separate the amino group and the fatty acid or fatty alkyl portion of the amino lipid. Suitable scaffolds are known to those of skill in the art.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwiterrionic, are not excluded from use in the invention.

In certain embodiments, protonatable lipids according to the invention have a pKa of the protonatable group in the range of about 4 to about 11. Most preferred is pKa of about 4 to about 7, because these lipids will be cationic at a lower pH formulation stage, while particles will be largely (though not completely) surface neutralized at physiological pH around pH 7.4. One of the benefits of this pKa is that at least some nucleic acid associated with the outside surface of the particle will lose its electrostatic interaction at physiological pH and be removed by simple dialysis; thus greatly reducing the particle's susceptibility to clearance.

One example of a cationic lipid is 1,2-Dilinolenyloxy-N, N-dimethylaminopropane (DLinDMA). Synthesis and preparation of nucleic acid-lipid particles including DlinDMA is described in International application number PCT/CA2009/00496, filed Apr. 15, 2009.

In one embodiment, the cationic lipid XTC (2,2-Dilinoleyl-4-dimethylaminoethyl-[1,3]-dioxolane) is used to prepare nucleic acid-lipid particles. Synthesis of XTC is described, e.g., in PCT/US10/22614 filed on Jan. 29, 2010, which is hereby incorporated by reference.

In another embodiment, the cationic lipid MC3 ((6Z,9Z, 28Z,31Z)-heptatriaconta-6,9,28,31-tetraen-19-yl-4-(dimethylamino)butanoate), (e.g., DLin-M-C3-DMA) is used to prepare nucleic acid-lipid particles. Synthesis of MC3 and MC3 comprising formulations are described, e.g., in U.S. Ser. No. 12/813,448, filed Jun. 10, 2010, which is hereby incorporated by reference.

In another embodiment, the cationic lipid ALNY-100 ((3aR,5s,6aS)—N,N-dimethyl-2,2-di((9Z,12Z)-octadeca-9, 12-dienyl)tetrahydro-3aH-cyclopenta[d][1,3]dioxol-5-amine) is used to prepare nucleic acid-lipid particles. Synthesis of ALNY-100 is described in International patent application number PCT/US09/63933 filed on Nov. 10, 2009, which is herein incorporated by reference.

The cationic lipid may comprise from about 20 mol % to about 70 mol % or about 45-65 mol % or about 40 mol % of the total lipid present in the particle.

Non-Cationic Lipids

The nucleic acid-lipid particles of the invention can include a non-cationic lipid. The non-cationic lipid may be an anionic lipid or a neutral lipid. Examples include but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof.

Anionic lipids suitable for use in lipid particles of the invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Neutral lipids, when present in the lipid particle, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono- or di-unsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the invention are DOPE, DSPC, POPC, or any related phosphatidylcholine. The neutral lipids useful in the invention may also be composed of sphingomyelin, dihydrosphingomyeline, or phospholipids with other head groups, such as serine and inositol.

In one embodiment the non-cationic lipid is distearoylphosphatidylcholine (DSPC). In another embodiment the non-cationic lipid is dipalmitoylphosphatidylcholine (DPPC).

The non-cationic lipid may be from about 5 mol % to about 90 mol %, about 5 mol % to about 10 mol %, about 10 mol %, or about 58 mol % if cholesterol is included, of the total lipid present in the particle.

Conjugated Lipids

Conjugated lipids can be used in nucleic acid-lipid particle to prevent aggregation, including polyethylene glycol (PEG)-modified lipids, monosialoganglioside Gm1, and polyamide oligomers ("PAO") such as (described in U.S. Pat. No. 6,320, 017). Other compounds with uncharged, hydrophilic, steric-barrier moieties, which prevent aggregation during formulation, like PEG, Gm1 or ATTA, can also be coupled to lipids for use as in the methods and compositions of the invention. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids).

Specific examples of PEG-modified lipids (or lipid-polyoxyethylene conjugates) that are useful in the invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in co-pending U.S. Ser. No. 08/486,214, incorporated herein by reference, PEG-modified dialkylamines and PEG-modified 1,2-diacyloxypropan-3-amines. Particularly preferred are PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mePEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 mins. in some assays. As illustrated in U.S. patent application Ser. No. 08/486,214, at least three characteristics influence the rate of exchange: length of acyl chain, saturation of acyl chain, and size of the steric-barrier head group. Compounds having suitable variations of these features may be useful for the invention. For some therapeutic applications, it may be preferable for the PEG-modified lipid to be rapidly lost from the nucleic acid-lipid particle in vivo and hence the PEG-modified lipid will possess relatively short lipid anchors. In other therapeutic applications, it may be preferable for the nucleic acid-lipid particle to exhibit a longer plasma circulation lifetime and hence the PEG-modified lipid will possess relatively longer lipid anchors. Exemplary lipid anchors include those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl($Ci_2$), a PEG-dimyristyloxypropyl($Ci_4$), a PEG-dipalmityloxypropyl ($Ci_6$), or a PEG-distearyloxypropyl($Ci_8$). Additional conjugated lipids include polyethylene glycol-didimyristoyl glycerol (C14-PEG or PEG-C14, where PEG has an average molecular weight of 2000 Da) (PEG-DMG); (R)-2,3-bis(octadecyloxy)propyl1-(methoxy poly(ethylene glycol)2000) propylcarbamate) (PEG-DSG); PEG-carbamoyl-1,2-dimyristyloxypropylamine, in which PEG has an average molecular weight of 2000 Da (PEG-cDMA); N-Acetylgalactosamine ((R)-2,3-bis(octadecyloxy)propyl1-(methoxy poly(ethylene glycol)2000)propylcarbamate)) (GalNAc-PEG-DSG); and polyethylene glycol-dipalmitoylglycerol (PEG-DPG).

In one embodiment the conjugated lipid is PEG-DMG. In another embodiment the conjugated lipid is PEG-cDMA. In still another embodiment the conjugated lipid is PEG-DPG. Alternatively the conjugated lipid is GalNAc-PEG-DSG.

The conjugated lipid that prevents aggregation of particles may be from 0 mol % to about 20 mol % or about 0.5 to about 5.0 mol % or about 2 mol % of the total lipid present in the particle.

The sterol component of the lipid mixture, when present, can be any of those sterols conventionally used in the field of liposome, lipid vesicle or lipid particle preparation. A preferred sterol is cholesterol.

In some embodiments, the nucleic acid-lipid particle further includes a sterol, e.g., a cholesterol at, e.g., about 10 mol % to about 60 mol % or about 25 to about 40 mol % or about 48 mol % of the total lipid present in the particle.

Lipoproteins

In one embodiment, the formulations of the invention further comprise an apolipoprotein. As used herein, the term "apolipoprotein" or "lipoprotein" refers to apolipoproteins known to those of skill in the art and variants and fragments thereof and to apolipoprotein agonists, analogues or fragments thereof described below.

Suitable apolipoproteins include, but are not limited to, ApoA-I, ApoA-II, ApoA-IV, ApoA-V and ApoE, and active polymorphic forms, isoforms, variants and mutants as well as fragments or truncated forms thereof. In certain embodiments, the apolipoprotein is a thiol containing apolipoprotein. "Thiol containing apolipoprotein" refers to an apolipoprotein, variant, fragment or isoform that contains at least one cysteine residue. The most common thiol containing apolipoproteins are ApoA-I Milano (ApoA-$I_M$) and ApoA-I Paris (ApoA-$I_P$) which contain one cysteine residue (Jia et al., 2002, Biochem. Biophys. Res. Comm. 297: 206-13; Bielicki and Oda, 2002, Biochemistry 41: 2089-96). ApoA-II, ApoE2 and ApoE3 are also thiol containing apolipoproteins. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; 5,116,739; the disclosures of which are herein incorporated by reference. ApoE3 is disclosed in Weisgraber, et al., "Human E apoprotein heterogeneity: cysteine-arginine interchanges in the amino acid sequence of the apo-E isoforms," J. Biol. Chem. (1981) 256: 9077-9083; and Rall, et al., "Structural basis for receptor binding heterogeneity of apolipoprotein E from type III hyperlipoproteinemic subjects," Proc. Nat. Acad. Sci. (1982) 79: 4696-4700. (See also GenBank accession number K00396.)

In certain embodiments, the apolipoprotein can be in its mature form, in its preproapolipoprotein form or in its proapolipoprotein form. Homo- and heterodimers (where feasible) of pro- and mature ApoA-I (Duverger et al., 1996, Arterioscler. Thromb. Vasc. Biol. 16(12):1424-29), ApoA-I Milano (Klon et al., 2000, Biophys. J. 79:(3)1679-87; Franceschini et al., 1985, J. Biol. Chem. 260: 1632-35), ApoA-I Paris (Daum et al., 1999, J. Mol. Med. 77:614-22), ApoA-II (Shelness et al., 1985, J. Biol. Chem. 260(14):8637-46; Shelness et al., 1984, J. Biol. Chem. 259(15):9929-35), ApoA-IV (Duverger et al., 1991, Euro. J. Biochem. 201(2):373-83), and ApoE (McLean et al., 1983, J. Biol. Chem. 258(14):8993-9000) can also be utilized within the scope of the invention.

In certain embodiments, the apolipoprotein can be a fragment, variant or isoform of the apolipoprotein. The term "fragment" refers to any apolipoprotein having an amino acid sequence shorter than that of a native apolipoprotein and which fragment retains the activity of native apolipoprotein, including lipid binding properties. By "variant" is meant substitutions or alterations in the amino acid sequences of the apolipoprotein, which substitutions or alterations, e.g., additions and deletions of amino acid residues, do not abolish the activity of native apolipoprotein, including lipid binding properties. Thus, a variant can comprise a protein or peptide having a substantially identical amino acid sequence to a native apolipoprotein provided herein in which one or more amino acid residues have been conservatively substituted with chemically similar amino acids. Examples of conservative substitutions include the substitution of at least one hydrophobic residue such as isoleucine, valine, leucine or methionine for another. Likewise, the present invention contemplates, for example, the substitution of at least one hydrophilic residue such as, for example, between arginine and lysine, between glutamine and asparagine, and between glycine and serine (see U.S. Pat. Nos. 6,004,925, 6,037,323 and 6,046,166). The term "isoform" refers to a protein having the same, greater or partial function and similar, identical or partial sequence, and may or may not be the product of the same gene and usually tissue specific (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al., 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sacre et al., 2003, FEBS Lett. 540(1-3):181-7; Weers, et al., 2003, Biophys. Chem. 100(1-3):481-92; Gong et al., 2002, J. Biol. Chem. 277(33):29919-26; Ohta et al., 1984, J. Biol. Chem. 259(23):14888-93 and U.S. Pat. No. 6,372,886).

In certain embodiments, the methods and compositions of the present invention include the use of a chimeric construction of an apolipoprotein. For example, a chimeric construction of an apolipoprotein can be comprised of an apolipoprotein domain with high lipid binding capacity associated with an apolipoprotein domain containing ischemia reperfusion protective properties. A chimeric construction of an apolipoprotein can be a construction that includes separate regions within an apolipoprotein (i.e., homologous construction) or a chimeric construction can be a construction that includes separate regions between different apolipoproteins (i.e., heterologous constructions). Compositions comprising a chimeric construction can also include segments that are apolipoprotein variants or segments designed to have a specific character (e.g., lipid binding, receptor binding, enzymatic, enzyme activating, antioxidant or reduction-oxidation property) (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al., 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sorenson et al., 1999, Arterioscler. Thromb. Vasc. Biol. 19(9):2214-25; Palgunachari 1996, Arterioscler. Throb. Vasc. Biol. 16(2):328-38: Thurberg et al., J. Biol. Chem. 271(11):6062-70; Dyer 1991, J. Biol. Chem. 266(23):150009-15; Hill 1998, J. Biol. Chem. 273(47):30979-84).

Apolipoproteins utilized in the invention also include recombinant, synthetic, semi-synthetic or purified apolipoproteins. Methods for obtaining apolipoproteins or equivalents thereof, utilized by the invention are well-known in the art. For example, apolipoproteins can be separated from plasma or natural products by, for example, density gradient centrifugation or immunoaffinity chromatography, or produced synthetically, semi-synthetically or using recombinant DNA techniques known to those of the art (see, e.g., Mulugeta et al., 1998, J. Chromatogr. 798(1-2): 83-90; Chung et al., 1980, J. Lipid Res. 21(3):284-91; Cheung et al., 1987, J. Lipid Res. 28(8):913-29; Persson, et al., 1998, J. Chromatogr. 711: 97-109; U.S. Pat. Nos. 5,059,528, 5,834,596, 5,876,968 and 5,721,114; and PCT Publications WO 86/04920 and WO 87/02062).

Apolipoproteins utilized in the invention further include apolipoprotein agonists such as peptides and peptide analogues that mimic the activity of ApoA-I, ApoA-I Milano (ApoA-$I_M$), ApoA-I Paris (ApoA-$I_P$), ApoA-II, ApoA-IV, and ApoE. For example, the apolipoprotein can be any of those described in U.S. Pat. Nos. 6,004,925, 6,037,323, 6,046,166, and 5,840,688, the contents of which are incorporated herein by reference in their entireties.

Apolipoprotein agonist peptides or peptide analogues can be synthesized or manufactured using any technique for peptide synthesis known in the art including, e.g., the techniques described in U.S. Pat. Nos. 6,004,925, 6,037,323 and 6,046,166. For example, the peptides may be prepared using the solid-phase synthetic technique initially described by Merrifield (1963, J. Am. Chem. Soc. 85:2149-2154). Other peptide synthesis techniques may be found in Bodanszky et al., Peptide Synthesis, John Wiley & Sons, 2d Ed., (1976) and other references readily available to those skilled in the art. A summary of polypeptide synthesis techniques can be found in Stuart and Young, Solid Phase Peptide. Synthesis, Pierce Chemical Company, Rockford, Ill., (1984). Peptides may also be synthesized by solution methods as described in The Proteins, Vol. II, 3d Ed., Neurath et al., Eds., p. 105-237, Academic Press, New York, N.Y. (1976). Appropriate protective groups for use in different peptide syntheses are described in the above-mentioned texts as well as in McOmie, Protective Groups in Organic Chemistry, Plenum Press, New York, N.Y. (1973). The peptides of the present invention might also be prepared by chemical or enzymatic cleavage from larger portions of, for example, apolipoprotein A-I.

In certain embodiments, the apolipoprotein can be a mixture of apolipoproteins. In one embodiment, the apolipoprotein can be a homogeneous mixture, that is, a single type of apolipoprotein. In another embodiment, the apolipoprotein can be a heterogeneous mixture of apolipoproteins, that is, a mixture of two or more different apolipoproteins. Embodiments of heterogenous mixtures of apolipoproteins can comprise, for example, a mixture of an apolipoprotein from an animal source and an apolipoprotein from a semi-synthetic source. In certain embodiments, a heterogenous mixture can comprise, for example, a mixture of ApoA-I and ApoA-I Milano. In certain embodiments, a heterogeneous mixture can comprise, for example, a mixture of ApoA-I Milano and ApoA-I Paris. Suitable mixtures for use in the methods and compositions of the invention will be apparent to one of skill in the art.

If the apolipoprotein is obtained from natural sources, it can be obtained from a plant or animal source. If the apolipoprotein is obtained from an animal source, the apolipoprotein can be from any species. In certain embodiments, the apolipoprotien can be obtained from an animal source. In certain embodiments, the apolipoprotein can be obtained from a human source. In preferred embodiments of the invention, the apolipoprotein is derived from the same species as the individual to which the apolipoprotein is administered.

Other Components

In numerous embodiments, amphipathic lipids are included in lipid particles of the invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the lipid particles of the invention are programmable fusion lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the lipid particle membrane over time. Exemplary lipid anchors include those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons.

A lipid particle conjugated to a nucleic acid agent can also include a targeting moiety, e.g., a targeting moiety that is specific to a cell type or tissue. Targeting of lipid particles using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can include the entire protein or fragments thereof. Targeting mechanisms generally require that the targeting agents be positioned on the surface of the lipid particle in such a manner that the targeting moiety is available for interaction with the target, for example, a cell surface receptor. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002).

The use of lipid particles, i.e., liposomes, with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci. (USA)*, 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes,* 149 *Methods in Enzymology* 111-119 (Academic Press, Inc. 1987)). Other targeting methods include the biotin-avidin system.

Production of Nucleic Acid-Lipid Particles

In one embodiment, the nucleic acid-lipid particle formulations of the invention are produced via an extrusion method or an in-line mixing method.

The extrusion method (also refer to as preformed method or batch process) is a method where the empty liposomes (i.e. no nucleic acid) are prepared first, followed by the addition of nucleic acid to the empty liposome. Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing. These methods are disclosed in the U.S. Pat. No. 5,008,050; U.S. Pat. No. 4,927,637; U.S. Pat. No. 4,737,323; *Biochim Biophys Acta.* 1979 Oct. 19; 557(1):9-23; *Biochim Biophys Acta.* 1980 Oct. 2; 601(3):559-7; *Biochim Biophys Acta.* 1986 Jun. 13; 858(1):161-8; and *Biochim. Biophys. Acta* 1985 812, 55-65, which are hereby incorporated by reference in their entirety.

The in-line mixing method is a method wherein both the lipids and the nucleic acid are added in parallel into a mixing chamber. The mixing chamber can be a simple T-connector or any other mixing chamber that is known to one skill in the art. These methods are disclosed in U.S. Pat. No. 6,534,018 and U.S. Pat. No. 6,855,277; US publication 2007/0042031 and *Pharmaceuticals Research*, Vol. 22, No. 3, March 2005, p. 362-372, which are hereby incorporated by reference in their entirety.

It is further understood that the formulations of the invention can be prepared by any methods known to one of ordinary skill in the art.

Characterization of Nucleic Acid-Lipid Particles

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. In one embodiment, the formulations of the invention are entrapped by at least 75%, at least 80% or at least 90%.

For nucleic acid-lipid particle formulations, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Formulations of Nucleic Acid-Lipid Particles

LNP01

One example of synthesis of a nucleic acid-lipid particle is as follows. Nucleic acid-lipid particles are synthesized using the lipidoid ND98.4HCl (MW 1487) (Formula I), Cholesterol (Sigma-Aldrich), and PEG-Ceramide C16 (Avanti Polar Lipids). This nucleic acid-lipid particle is sometimes referred to as a LNP01 particles. Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

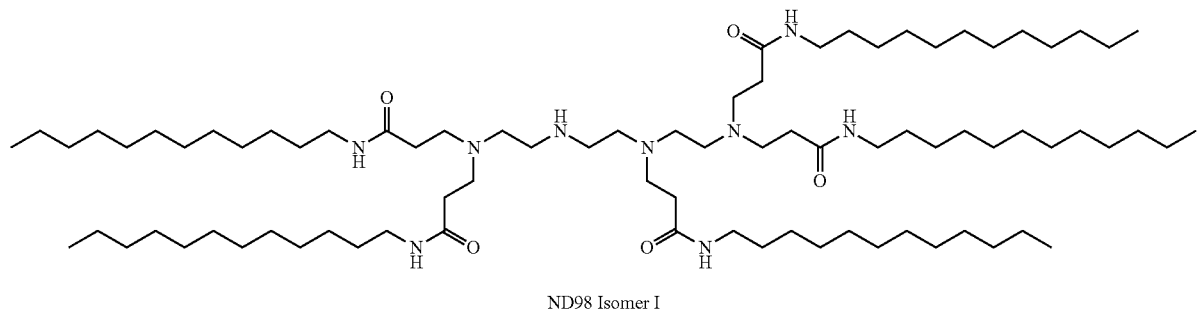

ND98 Isomer I

LNP01 formulations are described, e.g., in International Application Publication No. WO 2008/042973, which is hereby incorporated by reference.

Additional exemplary nucleic acid-lipid particle formulations are described in the following table. It is to be understood that the name of the nucleic acid-lipid particle in the table is not meant to be limiting. For example, as used herein, the term SNALP refers to formulations that include the cationic lipid DLinDMA.

| Name | cationic lipid/non-cationic lipid/cholesterol/PEG-lipid conjugate mol % ratio Lipid:siRNA ratio |
|---|---|
| SNALP | DLinDMA/DPPC/Cholesterol/PEG-cDMA (57.1/7.1/34.4/1.4) lipid:siRNA ~7:1 |
| LNP-S-X | XTC/DPPC/Cholesterol/PEG-cDMA 57.1/7.1/34.4/1.4 lipid:siRNA ~7:1 |
| LNP05 | XTC/DSPC/Cholesterol/PEG-DMG 57.5/7.5/31.5/3.5 lipid:siRNA ~6:1 |
| LNP06 | XTC/DSPC/Cholesterol/PEG-DMG 57.5/7.5/31.5/3.5 lipid:siRNA ~11:1 |
| LNP07 | XTC/DSPC/Cholesterol/PEG-DMG 60/7.5/31/1.5, lipid:siRNA ~6:1 |
| LNP08 | XTC/DSPC/Cholesterol/PEG-DMG 60/7.5/31/1.5, lipid:siRNA ~11:1 |
| LNP09 | XTC/DSPC/Cholesterol/PEG-DMG 50/10/38.5/1.5 lipid:siRNA ~10:1 |
| LNP10 | ALNY-100/DSPC/Cholesterol/PEG-DMG 50/10/38.5/1.5 lipid:siRNA ~10:1 |
| LNP11 | MC3/DSPC/Cholesterol/PEG-DMG 50/10/38.5/1.5 lipid:siRNA ~10:1 |

| Name | cationic lipid/non-cationic lipid/cholesterol/PEG-lipid conjugate mol % ratio Lipid:siRNA ratio |
|---|---|
| LNP13 | XTC/DSPC/Cholesterol/PEG-DMG 50/10/38.5/1.5 lipid:siRNA ~33:1 |
| LNP14 | MC3/DSPC/Cholesterol/PEG-DMG 40/15/40/5 lipid:siRNA ~11:1 |
| LNP15 | MC3/DSPC/Cholesterol/PEG-DSG/GalNAc-PEG-DSG 50/10/35/4.5/0.5 lipid:siRNA ~11:1 |
| LNP16 | MC3/DSPC/Cholesterol/PEG-DMG 50/10/38.5/1.5 lipid:siRNA ~7:1 |
| LNP17 | MC3/DSPC/Cholesterol/PEG-DSG 50/10/38.5/1.5 lipid:siRNA ~10:1 |
| LNP18 | MC3/DSPC/Cholesterol/PEG-DMG 50/10/38.5/1.5 lipid:siRNA ~12:1 |
| LNP19 | MC3/DSPC/Cholesterol/PEG-DMG 50/10/35/5 lipid:siRNA ~8:1 |
| LNP20 | MC3/DSPC/Cholesterol/PEG-DPG 50/10/38.5/1.5 lipid:siRNA ~10:1 |
| LNP22 | XTC/DSPC/Cholesterol/PEG-DSG 50/10/38.5/1.5 lipid:siRNA ~10:1 |

XTC comprising formulations are described, e.g., in PCT/US10/22614 filed on Jan. 29, 2010, which is hereby incorporated by reference.

MC3 comprising formulations are described, e.g., in U.S. Ser. No. 12/813,448, filed Jun. 10, 2010, which is hereby incorporated by reference.

ALNY-100 comprising formulations are described, e.g., International patent application number PCT/US09/63933, filed on Nov. 10, 2009, which is hereby incorporated by reference.

Additional representative formulations delineated in Tables 1 and 2. Lipid refers to a cationic lipid.

TABLE 1

Composition of exemplary nucleic acid-lipid particle (mole %) prepared via extrusion methods.

| Lipid (mol %) | DSPC (mol %) | Chol (mol %) | PEG (mol %) | Lipid/ siRNA |
|---|---|---|---|---|
| 20 | 30 | 40 | 10 | 2.13 |
| 20 | 30 | 40 | 10 | 2.35 |
| 20 | 30 | 40 | 10 | 2.37 |
| 20 | 30 | 40 | 10 | 3.23 |
| 20 | 30 | 40 | 10 | 3.91 |
| 30 | 20 | 40 | 10 | 2.89 |
| 30 | 20 | 40 | 10 | 3.34 |
| 30 | 20 | 40 | 10 | 3.34 |
| 30 | 20 | 40 | 10 | 4.10 |
| 30 | 20 | 40 | 10 | 5.64 |
| 40 | 10 | 40 | 10 | 3.02 |
| 40 | 10 | 40 | 10 | 3.35 |
| 40 | 10 | 40 | 10 | 3.74 |
| 40 | 10 | 40 | 10 | 5.80 |
| 40 | 10 | 40 | 10 | 8.00 |
| 45 | 5 | 40 | 10 | 3.27 |
| 45 | 5 | 40 | 10 | 3.30 |
| 45 | 5 | 40 | 10 | 4.45 |
| 45 | 5 | 40 | 10 | 7.00 |
| 45 | 5 | 40 | 10 | 9.80 |
| 50 | 0 | 40 | 10 | 27.03 |
| 20 | 35 | 40 | 5 | 3.00 |
| 20 | 35 | 40 | 5 | 3.32 |
| 20 | 35 | 40 | 5 | 3.05 |
| 20 | 35 | 40 | 5 | 3.67 |
| 20 | 35 | 40 | 5 | 4.71 |
| 30 | 25 | 40 | 5 | 2.47 |
| 30 | 25 | 40 | 5 | 2.98 |
| 30 | 25 | 40 | 5 | 3.29 |
| 30 | 25 | 40 | 5 | 4.99 |
| 30 | 25 | 40 | 5 | 7.15 |
| 40 | 15 | 40 | 5 | 2.79 |
| 40 | 15 | 40 | 5 | 3.29 |
| 40 | 15 | 40 | 5 | 4.33 |
| 40 | 15 | 40 | 5 | 7.05 |
| 40 | 15 | 40 | 5 | 9.63 |
| 45 | 10 | 40 | 5 | 2.44 |
| 45 | 10 | 40 | 5 | 3.21 |
| 45 | 10 | 40 | 5 | 4.29 |
| 45 | 10 | 40 | 5 | 6.50 |
| 45 | 10 | 40 | 5 | 8.67 |
| 20 | 35 | 40 | 5 | 4.10 |
| 20 | 35 | 40 | 5 | 4.83 |
| 30 | 25 | 40 | 5 | 3.86 |
| 30 | 25 | 40 | 5 | 5.38 |
| 30 | 25 | 40 | 5 | 7.07 |
| 40 | 15 | 40 | 5 | 3.85 |
| 40 | 15 | 40 | 5 | 4.88 |
| 40 | 15 | 40 | 5 | 7.22 |
| 40 | 15 | 40 | 5 | 9.75 |
| 45 | 10 | 40 | 5 | 2.83 |
| 45 | 10 | 40 | 5 | 3.85 |
| 45 | 10 | 40 | 5 | 4.88 |
| 45 | 10 | 40 | 5 | 7.05 |
| 45 | 10 | 40 | 5 | 9.29 |
| 45 | 20 | 30 | 5 | 4.01 |
| 45 | 20 | 30 | 5 | 3.70 |
| 50 | 15 | 30 | 5 | 4.75 |
| 50 | 15 | 30 | 5 | 3.80 |
| 55 | 10 | 30 | 5 | 3.85 |
| 55 | 10 | 30 | 5 | 4.13 |
| 60 | 5 | 30 | 5 | 5.09 |
| 60 | 5 | 30 | 5 | 4.67 |
| 65 | 0 | 30 | 5 | 4.75 |
| 65 | 0 | 30 | 5 | 6.06 |
| 56.5 | 10 | 30 | 3.5 | 3.70 |
| 56.5 | 10 | 30 | 3.5 | 3.56 |
| 57.5 | 10 | 30 | 2.5 | 3.48 |
| 57.5 | 10 | 30 | 2.5 | 3.20 |
| 58.5 | 10 | 30 | 1.5 | 3.24 |
| 58.5 | 10 | 30 | 1.5 | 3.13 |
| 59.5 | 10 | 30 | 0.5 | 3.24 |
| 59.5 | 10 | 30 | 0.5 | 3.03 |
| 45 | 10 | 40 | 5 | 7.57 |
| 45 | 10 | 40 | 5 | 7.24 |
| 45 | 10 | 40 | 5 | 7.48 |
| 45 | 10 | 40 | 5 | 7.84 |
| 65 | 0 | 30 | 5 | 4.01 |
| 60 | 5 | 30 | 5 | 3.70 |
| 55 | 10 | 30 | 5 | 3.65 |
| 50 | 10 | 35 | 5 | 3.43 |
| 50 | 15 | 30 | 5 | 3.80 |
| 45 | 15 | 35 | 5 | 3.70 |
| 45 | 20 | 30 | 5 | 3.75 |
| 45 | 25 | 25 | 5 | 3.85 |
| 55 | 10 | 32.5 | 2.5 | 3.61 |
| 60 | 10 | 27.5 | 2.5 | 3.65 |
| 60 | 10 | 25 | 5 | 4.07 |
| 55 | 5 | 38.5 | 1.5 | 3.75 |
| 60 | 10 | 28.5 | 1.5 | 3.43 |
| 55 | 10 | 33.5 | 1.5 | 3.48 |
| 60 | 5 | 33.5 | 1.5 | 3.43 |
| 55 | 5 | 37.5 | 2.5 | 3.75 |
| 60 | 5 | 32.5 | 2.5 | 4.52 |
| 60 | 5 | 32.5 | 2.5 | 3.52 |
| 45 | 15 (DMPC) | 35 | 5 | 3.20 |

TABLE 1-continued

Composition of exemplary nucleic acid-lipid particle (mole %) prepared via extrusion methods.

| Lipid (mol %) | DSPC (mol %) | Chol (mol %) | PEG (mol %) | Lipid/siRNA |
|---|---|---|---|---|
| 45 | 15 (DPPC) | 35 | 5 | 3.43 |
| 45 | 15 (DOPC) | 35 | 5 | 4.52 |
| 45 | 15 (POPC) | 35 | 5 | 3.85 |
| 55 | 5 | 37.5 | 2.5 | 3.96 |
| 55 | 10 | 32.5 | 2.5 | 3.56 |
| 60 | 5 | 32.5 | 2.5 | 3.80 |
| 60 | 10 | 27.5 | 2.5 | 3.75 |
| 60 | 5 | 30 | 5 | 4.19 |
| 60 | 5 | 33.5 | 1.5 | 3.48 |
| 60 | 5 | 33.5 | 1.5 | 6.64 |
| 60 | 5 | 30 | 5 | 3.90 |
| 60 | 5 | 30 | 5 | 4.65 |
| 60 | 5 | 30 | 5 | 5.88 |
| 60 | 5 | 30 | 5 | 7.51 |
| 60 | 5 | 30 | 5 | 9.51 |
| 60 | 5 | 30 | 5 | 11.06 |
| 62.5 | 2.5 | 50 | 5 | 6.63 |
| 45 | 15 | 35 | 5 | 3.31 |
| 45 | 15 | 35 | 5 | 6.80 |
| 60 | 5 | 25 | 10 | 6.48 |
| 60 | 5 | 32.5 | 2.5 | 3.43 |
| 60 | 5 | 30 | 5 | 3.90 |
| 60 | 5 | 30 | 5 | 7.61 |
| 45 | 15 | 35 | 5 | 3.13 |
| 45 | 15 | 35 | 5 | 6.42 |
| 60 | 5 | 25 | 10 | 6.48 |
| 60 | 5 | 32.5 | 2.5 | 3.03 |
| 60 | 5 | 30 | 5 | 3.43 |
| 60 | 5 | 30 | 5 | 6.72 |
| 60 | 5 | 30 | 5 | 4.13 |
| 70 | 5 | 20 | 5 | 5.48 |
| 80 | 5 | 10 | 5 | 5.94 |
| 90 | 5 | 0 | 5 | 9.50 |
| 60 | 5 | 30 | 5 C12PEG | 3.85 |
| 60 | 5 | 30 | 5 | 3.70 |
| 60 | 5 | 30 | 5 C16PEG | 3.80 |
| 60 | 5 | 30 | 5 | 4.19 |
| 60 | 5 | 29 | 5 | 4.07 |
| 60 | 5 | 30 | 5 | 3.56 |
| 60 | 5 | 30 | 5 | 3.39 |
| 60 | 5 | 30 | 5 | 3.96 |
| 60 | 5 | 30 | 5 | 4.01 |
| 60 | 5 | 30 | 5 | 4.07 |
| 60 | 5 | 30 | 5 | 4.25 |
| 60 | 5 | 30 | 5 | 3.80 |
| 60 | 5 | 30 | 5 | 3.31 |
| 60 | 5 | 30 | 5 | 4.83 |
| 60 | 5 | 30 | 5 | 4.67 |
| 60 | 5 | 30 | 5 | 3.96 |
| 57.5 | 7.5 | 33.5 | 1.5 | 3.39 |
| 57.5 | 7.5 | 32.5 | 2.5 | 3.39 |
| 57.5 | 7.5 | 31.5 | 3.5 | 3.52 |
| 57.5 | 7.5 | 30 | 5 | 4.19 |
| 60 | 5 | 30 | 5 | 3.96 |
| 60 | 5 | 30 | 5 | 3.96 |
| 60 | 5 | 30 | 5 | 3.56 |
| 60 | 5 | 33.5 | 1.5 | 3.52 |
| 60 | 5 | 25 | 10 | 5.18 |
| 60 | 5 (DPPC) | 30 | 5 | 4.25 |
| 60 | 5 | 32.5 | 2.5 | 3.70 |
| 57.5 | 7.5 | 31.5 | 3.5 | 3.06 |
| 57.5 | 7.5 | 31.5 | 3.5 | 3.65 |
| 57.5 | 7.5 | 31.5 | 3.5 | 4.70 |
| 57.5 | 7.5 | 31.5 | 3.5 | 6.56 |

TABLE 2

Composition of exemplary nucleic acid-lipid particles prepared via in-line mixing

| Lipid (mol %) | DSPC (mol %) | Chol (mol %) | PEG (mol %) | Lipid A/siRNA |
|---|---|---|---|---|
| 55 | 5 | 37.5 | 2.5 | 3.96 |
| 55 | 10 | 32.5 | 2.5 | 3.56 |
| 60 | 5 | 32.5 | 2.5 | 3.80 |
| 60 | 10 | 27.5 | 2.5 | 3.75 |
| 60 | 5 | 30 | 5 | 4.19 |
| 60 | 5 | 33.5 | 1.5 | 3.48 |
| 60 | 5 | 33.5 | 1.5 | 6.64 |
| 60 | 5 | 25 | 10 | 6.79 |
| 60 | 5 | 32.5 | 2.5 | 3.96 |
| 60 | 5 | 34 | 1 | 3.75 |
| 60 | 5 | 34.5 | 0.5 | 3.28 |
| 50 | 5 | 40 | 5 | 3.96 |
| 60 | 5 | 30 | 5 | 4.75 |
| 70 | 5 | 20 | 5 | 5.00 |
| 80 | 5 | 10 | 5 | 5.18 |
| 60 | 5 | 30 | 5 | 13.60 |
| 60 | 5 | 30 | 5 | 14.51 |
| 60 | 5 | 30 | 5 | 6.20 |
| 60 | 5 | 30 | 5 | 4.60 |
| 60 | 5 | 30 | 5 | 6.20 |
| 60 | 5 | 30 | 5 | 5.82 |
| 40 | 5 | 54 | 1 | 3.39 |
| 40 | 7.5 | 51.5 | 1 | 3.39 |
| 40 | 10 | 49 | 1 | 3.39 |
| 50 | 5 | 44 | 1 | 3.39 |
| 50 | 7.5 | 41.5 | 1 | 3.43 |
| 50 | 10 | 39 | 1 | 3.35 |
| 60 | 5 | 34 | 1 | 3.52 |
| 60 | 7.5 | 31.5 | 1 | 3.56 |
| 60 | 10 | 29 | 1 | 3.80 |
| 70 | 5 | 24 | 1 | 3.70 |
| 70 | 7.5 | 21.5 | 1 | 4.13 |
| 70 | 10 | 19 | 1 | 3.85 |
| 60 | 5 | 34 | 1 | 3.52 |
| 60 | 5 | 34 | 1 | 3.70 |
| 60 | 5 | 34 | 1 | 3.52 |
| 60 | 7.5 | 27.5 | 5 | 5.18 |
| 60 | 7.5 | 29 | 3.5 | 4.45 |
| 60 | 5 | 31.5 | 3.5 | 4.83 |
| 60 | 7.5 | 31 | 1.5 | 3.48 |
| 57.5 | 7.5 | 30 | 5 | 4.75 |
| 57.5 | 7.5 | 31.5 | 3.5 | 4.83 |
| 57.5 | 5 | 34 | 3.5 | 4.67 |
| 57.5 | 7.5 | 33.5 | 1.5 | 3.43 |
| 55 | 7.5 | 32.5 | 5 | 4.38 |
| 55 | 7.5 | 34 | 3.5 | 4.13 |
| 55 | 5 | 36.5 | 3.5 | 4.38 |
| 55 | 7.5 | 36 | 1.5 | 3.35 |

Synthesis of Cationic Lipids.

Any of the compounds, e.g., cationic lipids and the like, used in the nucleic acid-lipid particles of the invention may be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(═O)alkyl, —C(═O)alkenyl, and —C(═O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (═O) two hydrogen atoms are replaced. In this regard, substituents include oxo, halogen, heterocycle, —CN, —OR$^x$, —NR$^x$R$^y$, —NR$^x$C(═O)R$^y$, —NR$^x$SO$_2$R$^y$, —C(═O)R$^x$, —C(═O)OR$^x$, —C(═O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR$^x$, heterocycle, —NR$^x$R$^y$, —NR$^x$C(═O)R$^y$, —NR$^x$SO$_2$R$^y$, —C(═O)R$^x$, —C(═O)OR$^x$, —C(═O)NR$^x$R$^y$, —SO$_n$R$^x$ and —SO$_n$NR$^x$R$^y$.

"Halogen" means fluoro, chloro, bromo and iodo.

In some embodiments, the methods of the invention may require the use of protecting groups. Protecting group methodology is well known to those skilled in the art (see, for example, PROTECTIVE GROUPS IN ORGANIC SYNTHESIS, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In one embodiments, nucleic acid-lipid particles of the invention are formulated using a cationic lipid of formula A:

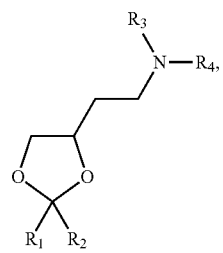

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above may be made by the following Reaction Schemes 1 or 2, wherein all substituents are as defined above unless indicated otherwise.

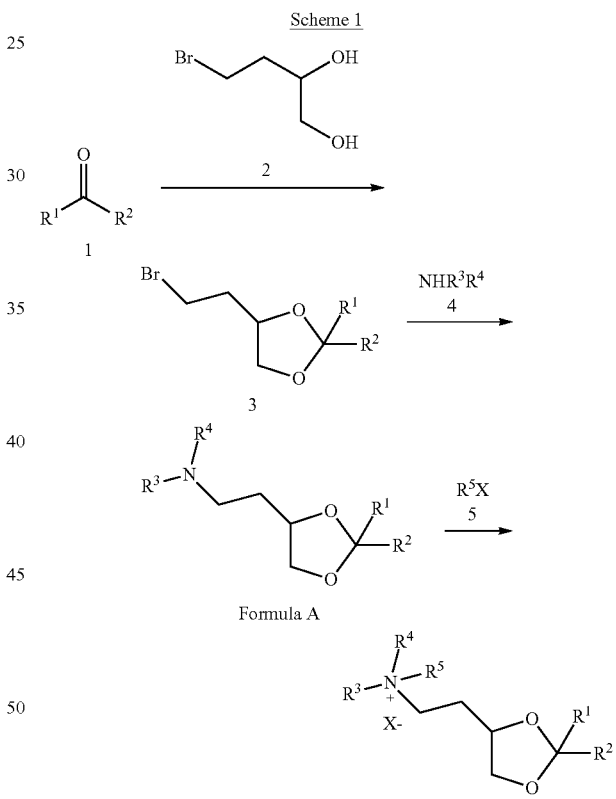

Lipid A, where R$_1$ and R$_2$ are independently alkyl, alkenyl or alkynyl, each can be optionally substituted, and R$_3$ and R$_4$ are independently lower alkyl or R$_3$ and R$_4$ can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

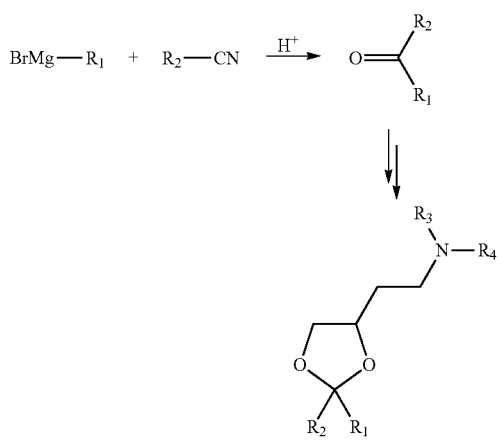

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl-4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

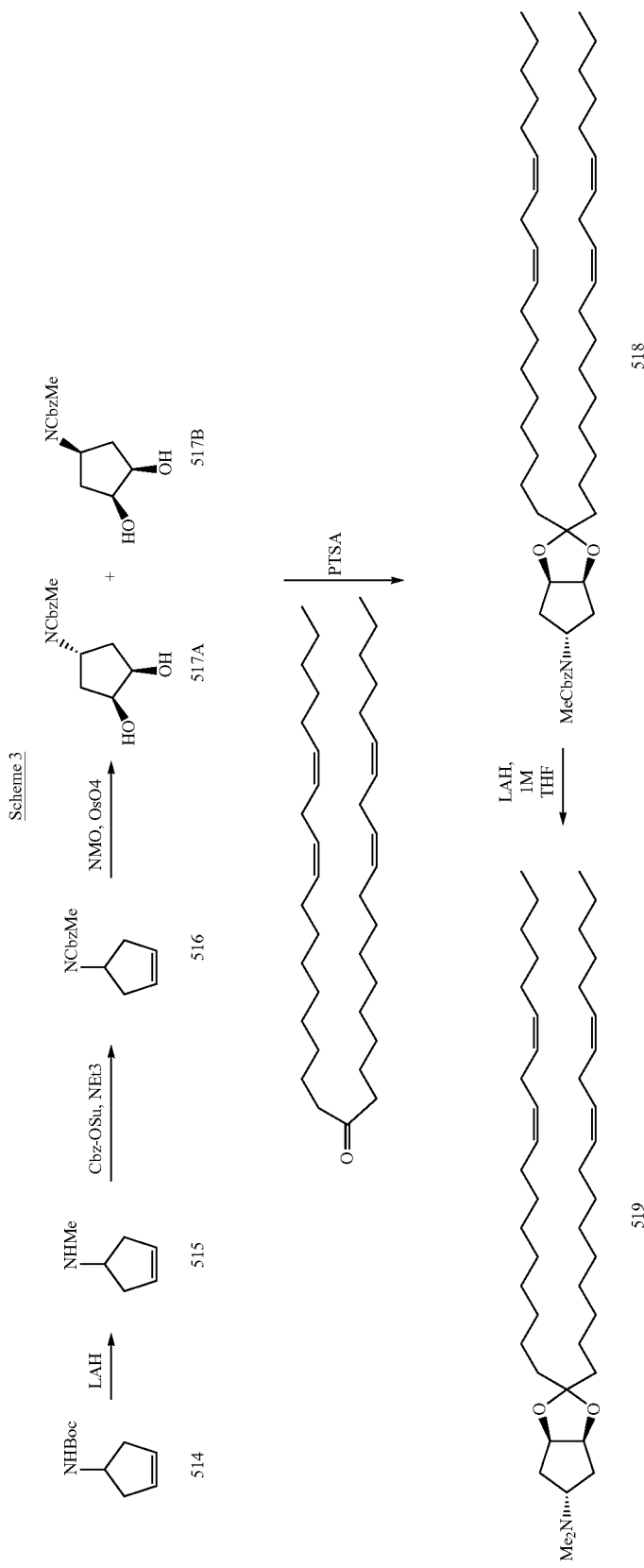

Synthesis of 515:

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g $^1$H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516:

To a stirred solution of compound 515 in 100 mL dry DCM in a 250 mL two neck RBF, was added NEt$_3$ (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). $^1$H-NMR (CDCl$_3$, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B:

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1×50 mL). Organic phase was dried over an. Na2SO4 and solvent was removed in vacuum. Silica gel column chromatographic purification of the crude material was afforded a mixture of diastereomers, which were separated by prep HPLC. Yield: ~6 g crude 517A—Peak-1 (white solid), 5.13 g (96%). $^1$H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H]-266.3, [M+NH4+]—283.5 present, HPLC—97.86%. Stereochemistry confirmed by X-ray.

Synthesis of 518:

Using a procedure analogous to that described for the synthesis of compound 505, compound 518 (1.2 g, 41%) was obtained as a colorless oil. $^1$H-NMR (CDCl$_3$, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC—98.65%.

General Procedure for the Synthesis of Compound 519:

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. $^{13}$C NMR=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6. Found 654.6.

Therapeutic Agent-Lipid Particle Compositions and Formulations

The invention includes compositions comprising a lipid particle of the invention and an active agent, wherein the active agent is associated with the lipid particle. In particular embodiments, the active agent is a therapeutic agent. In particular embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

"Fully encapsulated" as used herein indicates that the nucleic acid in the particles is not significantly degraded after exposure to serum or a nuclease assay that would significantly degrade free DNA. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, Calif.). Fully encapsulated also suggests that the particles are serum stable, that is, that they do not rapidly decompose into their component parts upon in vivo administration.

Active agents, as used herein, include any molecule or compound capable of exerting a desired effect on a cell, tissue, organ, or subject. Such effects may be biological, physiological, or cosmetic, for example. Active agents may be any type of molecule or compound, including e.g., nucleic acids, peptides and polypeptides, including, e.g., antibodies, such as, e.g., polyclonal antibodies, monoclonal antibodies, antibody fragments; humanized antibodies, recombinant antibodies, recombinant human antibodies, and Primatized™ antibodies, cytokines, growth factors, apoptotic factors, differentiation-inducing factors, cell surface receptors and their ligands; hormones; and small molecules, including small organic molecules or compounds.

In one embodiment, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative lacks therapeutic activity.

In various embodiments, therapeutic agents include any therapeutically effective agent or drug, such as anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs, e.g., anti-arrhythmic agents, vasoconstrictors, hormones, and steroids.

In certain embodiments, the therapeutic agent is an oncology drug, which may also be referred to as an anti-tumor drug, an anti-cancer drug, a tumor drug, an antineoplastic agent, or the like. Examples of oncology drugs that may be used according to the invention include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used according to the invention are ellipticin and ellipticin analogs or derivatives, epothilones, intracellular kinase inhibitors and camptothecins.

Additional Formulations

Emulsions

The compositions of the present invention may be prepared and formulated as emulsions. Emulsions are typically heterogeneous systems of one liquid dispersed in another in the form of droplets usually exceeding 0.1 µm in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, non-swelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly dsRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

The agent and dsRNAs targeting a gene of interest of the present invention can be formulated in a pharmaceutically acceptable carrier or diluent. A "pharmaceutically acceptable carrier" (also referred to herein as an "excipient") is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate);

lubricants (e.g., starch, polyethylene glycol, or sodium acetate); disintegrates (e.g., starch or sodium starch glycolate); and wetting agents (e.g., sodium lauryl sulfate).

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, typically with an excess of the latter substance, can result in a substantial reduction of the amount of nucleic acid recovered in the liver, kidney or other extra-circulatory reservoirs, presumably due to competition between the carrier compound and the nucleic acid for a common receptor. For example, the recovery of a partially phosphorothioate dsRNA in hepatic tissue can be reduced when it is co-administered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Methods of Preparing Lipid Particles

The methods and compositions of the invention make use of certain cationic lipids, the synthesis, preparation and characterization of which is described below and in the accompanying Examples. In addition, the present invention provides methods of preparing lipid particles, including those associated with a therapeutic agent, e.g., a nucleic acid. In the methods described herein, a mixture of lipids is combined with a buffered aqueous solution of nucleic acid to produce an intermediate mixture containing nucleic acid encapsulated in lipid particles wherein the encapsulated nucleic acids are present in a nucleic acid/lipid ratio of about 3 wt % to about 25 wt %, preferably 5 to 15 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

As described above, several of these cationic lipids are amino lipids that are charged at a pH below the $pK_a$ of the amino group and substantially neutral at a pH above the $pK_a$. These cationic lipids are termed titratable cationic lipids and can be used in the formulations of the invention using a two-step process. First, lipid vesicles can be formed at the lower pH with titratable cationic lipids and other vesicle components in the presence of nucleic acids. In this manner, the vesicles will encapsulate and entrap the nucleic acids. Second, the surface charge of the newly formed vesicles can be neutralized by increasing the pH of the medium to a level above the $pK_a$ of the titratable cationic lipids present, i.e., to physiological pH or higher. Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations. Additional details concerning these uses of such titratable cationic lipids in the formulation of nucleic acid-lipid particles are provided in U.S. Pat. No. 6,287,591 and U.S. Pat. No. 6,858,225, incorporated herein by reference.

It is further noted that the vesicles formed in this manner provide formulations of uniform vesicle size with high content of nucleic acids. Additionally, the vesicles have a size range of from about 30 to about 150 nm, more preferably about 30 to about 90 nm.

Without intending to be bound by any particular theory, it is believed that the very high efficiency of nucleic acid encapsulation is a result of electrostatic interaction at low pH. At acidic pH (e.g. pH 4.0) the vesicle surface is charged and binds a portion of the nucleic acids through electrostatic interactions. When the external acidic buffer is exchanged for a more neutral buffer (e.g. pH 7.5) the surface of the lipid particle or liposome is neutralized, allowing any external nucleic acid to be removed. More detailed information on the formulation process is provided in various publications (e.g., U.S. Pat. No. 6,287,591 and U.S. Pat. No. 6,858,225).

In view of the above, the present invention provides methods of preparing lipid/nucleic acid formulations. In the methods described herein, a mixture of lipids is combined with a buffered aqueous solution of nucleic acid to produce an intermediate mixture containing nucleic acid encapsulated in lipid particles, e.g., wherein the encapsulated nucleic acids are present in a nucleic acid/lipid ratio of about 10 wt % to about 20 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

In certain embodiments, the mixture of lipids includes at least two lipid components: a first amino lipid component of the present invention that is selected from among lipids which have a pKa such that the lipid is cationic at pH below the pKa and neutral at pH above the pKa, and a second lipid component that is selected from among lipids that prevent particle aggregation during lipid-nucleic acid particle formation. In particular embodiments, the amino lipid is a novel cationic lipid of the present invention.

In preparing the nucleic acid-lipid particles of the invention, the mixture of lipids is typically a solution of lipids in an organic solvent. This mixture of lipids can then be dried to form a thin film or lyophilized to form a powder before being hydrated with an aqueous buffer to form liposomes. Alternatively, in a preferred method, the lipid mixture can be solubilized in a water miscible alcohol, such as ethanol, and this ethanolic solution added to an aqueous buffer resulting in spontaneous liposome formation. In most embodiments, the alcohol is used in the form in which it is commercially available. For example, ethanol can be used as absolute ethanol (100%), or as 95% ethanol, the remainder being water. This method is described in more detail in U.S. Pat. No. 5,976,567).

In accordance with the invention, the lipid mixture is combined with a buffered aqueous solution that may contain the nucleic acids. The buffered aqueous solution of is typically a solution in which the buffer has a pH of less than the $pK_a$, of the protonatable lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the nucleic acid being encapsulated, and optimization of buffer concentration may be significant to achieving high loading levels (see, e.g., U.S. Pat. No. 6,287,591 and U.S. Pat. No. 6,858,225). Alternatively, pure water acidified to pH 5-6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of nucleic acid in buffer can vary, but will typically be from about 0.01 mg/mL to about 200 mg/mL, more preferably from about 0.5 mg/mL to about 50 mg/mL.

The mixture of lipids and the buffered aqueous solution of therapeutic nucleic acids is combined to provide an intermediate mixture. The intermediate mixture is typically a mixture of lipid particles having encapsulated nucleic acids. Additionally, the intermediate mixture may also contain some portion of nucleic acids which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$ of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of formulation produced. For example, when the total volume is about 10-20 mL or less, the solutions can be combined in a test tube and stirred together using a vortex mixer. Large-scale processes can be carried out in suitable production scale glassware.

Optionally, the lipid-encapsulated therapeutic agent (e.g., nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm. Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination. For certain methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

In particular embodiments, methods of the present invention further comprise a step of neutralizing at least some of the surface charges on the lipid portions of the lipid-nucleic acid compositions. By at least partially neutralizing the surface charges, unencapsulated nucleic acid is freed from the lipid particle surface and can be removed from the composition using conventional techniques. Preferably, unencapsulated and surface adsorbed nucleic acids are removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and nucleic acid release from the surface. The released nucleic acid can then be removed via chromatography using standard methods, and then switched into a buffer with a pH above the pKa of the lipid used.

Optionally the lipid vesicles (i.e., lipid particles) can be formed by hydration in an aqueous buffer and sized using any of the methods described above prior to addition of the nucleic acid. As described above, the aqueous buffer should be of a pH below the pKa of the amino lipid. A solution of the nucleic acids can then be added to these sized, preformed vesicles. To allow encapsulation of nucleic acids into such "pre-formed" vesicles the mixture should contain an alcohol, such as ethanol. In the case of ethanol, it should be present at a concentration of about 20% (w/w) to about 45% (w/w). In addition, it may be necessary to warm the mixture of pre-formed vesicles and nucleic acid in the aqueous buffer-ethanol mixture to a temperature of about 25° C. to about 50° C. depending on the composition of the lipid vesicles and the nature of the nucleic acid. It will be apparent to one of ordinary skill in the art that optimization of the encapsulation process to achieve a desired level of nucleic acid in the lipid vesicles will require manipulation of variable such as ethanol concentration and temperature. Examples of suitable conditions for nucleic acid encapsulation are provided in the Examples. Once the nucleic acids are encapsulated within the preformed vesicles, the external pH can be increased to at least partially neutralize the surface charge. Unencapsulated and surface adsorbed nucleic acids can then be removed as described above.

Method of Use

The lipid particles of the invention may be used to deliver a therapeutic agent to a cell, in vitro or in vivo. In particular embodiments, the therapeutic agent is a nucleic acid, which is delivered to a cell using a nucleic acid-lipid particles of the invention. While the following description of various methods of using the lipid particles and related pharmaceutical compositions of the invention are exemplified by description related to nucleic acid-lipid particles, it is understood that these methods and compositions may be readily adapted for the delivery of any therapeutic agent for the treatment of any disease or disorder that would benefit from such treatment.

In certain embodiments, the invention provides methods for introducing a nucleic acid into a cell. Preferred nucleic acids for introduction into cells are siRNA, immune-stimulating oligonucleotides, plasmids, antisense and ribozymes. These methods may be carried out by contacting the particles or compositions of the invention with the cells for a period of time sufficient for intracellular delivery to occur.

The compositions of the invention can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited with respect to the scope of the invention, it is believed that in the case of particles taken up into the cell by endocytosis the particles then interact with the endosomal membrane, resulting in destabilization of the endosomal membrane, possibly by the formation of non-bilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 μmol and about 10 mmol. In certain embodiments, treatment of the cells with the lipid-nucleic acid compositions will generally be carried out at physiological temperatures (about 37° C.) for periods of time from about 1 to 24 hours, preferably from about 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about $10^3$ to about $10^5$ cells/mL, more preferably about $2 \times 10^4$ cells/mL. The concentration of the suspension added to the cells is preferably of from about 0.01 to 20 μg/mL, more preferably about 1 μg/mL.

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630-643 (1989), and for cystic fibrosis, see Goodfellow, *Nature* 341:102-103 (1989)). Other uses for the compositions of the invention include introduction of antisense oligonucleotides in cells (see, Bennett, et al., *Mol. Pharm.* 41:1023-1033 (1992)).

Alternatively, the compositions of the invention can also be used for deliver of nucleic acids to cells in vivo, using methods which are known to those of skill in the art. With respect to application of the invention for delivery of DNA or mRNA sequences, Zhu, et al., *Science* 261:209-211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250-256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278-281 (1989), incorporated herein by reference, describes the in vivo transfection of lungs of mice with a functioning prokaryotic gene encoding the intracellular enzyme, chloramphenicol acetyltransferase (CAT). Thus, the compositions of the invention can be used in the treatment of infectious diseases.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. For one example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512-527 (1983); Mannino, et al., *Biotechniques* 6:682-690 (1988); Nicolau, et al., *Crit. Rev. Ther. Drug Carrier Syst.* 6:239-271 (1989), and Behr, *Acc. Chem. Res.* 26:274-278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, et al., *Am. J. Sci.* 298(4):278-281 (1989)) or by direct injection at the site of disease (Culver, Human Gene Therapy, MaryAnn Liebert, Inc., Publishers, New York. pp. 70-71 (1994)).

The methods of the invention may be practiced in a variety of hosts. Preferred hosts include mammalian species, such as humans, non-human primates, dogs, cats, cattle, horses, sheep, and the like.

Dosages for the lipid-therapeutic agent particles of the invention will depend on the ratio of therapeutic agent to lipid and the administrating physician's opinion based on age, weight, and condition of the patient.

In one embodiment, the invention provides a method of modulating the expression of a target polynucleotide or polypeptide. These methods generally comprise contacting a cell with a lipid particle of the invention that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value. For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polynucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In one particular embodiment, the invention provides a method of modulating the expression of a polypeptide by a cell, comprising providing to a cell a lipid particle that consists of or consists essentially of a cationic lipid of formula A, a neutral lipid, a sterol, a PEG of PEG-modified lipid, e.g., in a molar ratio of about 35-65% of cationic lipid of formula A, 3-12% of the neutral lipid, 15-45% of the sterol, and 0.5-10% of the PEG or PEG-modified lipid, wherein the lipid particle is associated with a nucleic acid capable of modulating the expression of the polypeptide. In particular embodiments, the molar lipid ratio is approximately 60/7.5/31/1.5 or 57.5/7.5/31.5/3.5 (mol % LIPID A/DSPC/Chol/PEG-DMG). In another group of embodiments, the neutral lipid in these compositions is replaced with DPPC (dipalmitoylphosphatidylcholine), POPC, DOPE or SM.

In particular embodiments, the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, the invention provides a method of treating a disease or disorder characterized by overexpression of a polypeptide in a subject, comprising providing to the subject a pharmaceutical composition of the invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In one embodiment, the pharmaceutical composition comprises a lipid particle that consists of or consists essentially of Lipid A, DSPC, Chol and PEG-DMG, PEG-C-DOMG or PEG-DMA, e.g., in a molar ratio of about 35-65% of cationic lipid of formula A, 3-12% of the neutral lipid, 15-45% of the sterol, and 0.5-10% of the PEG or PEG-modified lipid PEG-DMG, PEG-C-DOMG or PEG-DMA, wherein the lipid particle is associated with the therapeutic nucleic acid. In particular embodiments, the molar lipid ratio is approximately 60/7.5/31/1.5 or 57.5/7.5/31.5/3.5 (mol % LIPID A/DSPC/Chol/PEG-DMG). In another group of embodiments, the neutral lipid in these compositions is replaced with DPPC, POPC, DOPE or SM.

In another related embodiment, the invention includes a method of treating a disease or disorder characterized by underexpression of a polypeptide in a subject, comprising providing to the subject a pharmaceutical composition of the invention, wherein the therapeutic agent is a plasmid that encodes the polypeptide or a functional variant or fragment thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Methods for Inhibiting Expression of a Target Gene

In yet another aspect, the invention provides a method for inhibiting the expression of a target gene in a mammal. The method includes administering a composition featured in the invention to the mammal such that expression of the target gene is silenced.

In one embodiment, a method for inhibiting target gene expression includes administering a composition containing a dsRNA molecule having a nucleotide sequence that is complementary to at least a part of an RNA transcript of the target gene of the mammal to be treated. When the organism to be treated is a mammal such as a human, the composition may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection.

EXAMPLES

Example 1

PCSK9 siRNAs Reduce Circulating LDLc, ApoB, and PCSK9, but not HDLc in Non-Human Primates (NHPs)

In earlier experiments, siRNAs targeting PCSK9 acutely lowered both PCSK9 and total cholesterol levels by 72 hours post-dose and lasted ~21-30 days after a single dose in mice and rats. See, e.g., U.S. Ser. No. 12/554,231; U.S. Ser. No. 12/478,452; and U.S. Pat. No. 7,605,251. To extend these findings to a species whose lipoprotein profiles most closely mimic that of humans, further experiments were performed in the Cynomologous (Cyno) monkey model.

siRNA 1 based on AD-10792 (LNP01-10792 aka LNP01-1a2) and siRNA 2 based on AD-9680 (LNP-01-9680 aka LNP01-2a1), both targeting PCSK9 were administered to cynomologous monkeys.

| Name | Position in human access.# | Sense | Anti-sense | Sequence 5'-3' | SEQ ID NO: |
|---|---|---|---|---|---|
| AD-10792 | 1091 | 2' OMe | 2' OMe | GccuGGAGuuuAu ucGGAAdTsdT | 17 |
| | | | | UUCCGAAuAAACU CcAGGCdTsdT | 18 |
| AD-9680 | 3530 (3' UTR) | 2' OMe | 2' OMe | uucuAGAccuGuu uuGcuudTsdT | 19 |
| | | | | AAGcAAAAcAGGU CuAGAAdTsdT | 20 |

U, C, A, G: corresponding ribonucleotide; T: deoxythymidine; u, c, a, g: corresponding 2'-O-methyl ribonucleotide; Uf, Cf, Af, Gf: corresponding 2'-deoxy-2'-fluoro ribonucleotide; where nucleotides are written in sequence, they are connected by 3'-5' phosphodiester groups; nucleotides with interjected "s" are connected by 3'-O-5'-O phosphorothiodiester groups; unless denoted by prefix "p-", oligonucleotides are devoid of a 5'-phosphate group on the 5'-most nucleotide; all oligonucleotides bear 3'-OH on the 3'-most nucleotide.

As shown in FIG. 1, both siRNAs caused significant lipid lowering for up to 7 days post administration. siRNA 2 caused ~50% lipid lowering for at least 7 days post-administration, and ~60% lipid lowering at day 14 post-administration, and siRNA 1 caused ~60% LDLc lowering for at least 7 days.

Male Cynos were first pre-screened for those that had LDLc of 40 mg/dl or higher. Chosen animals were then put on a fasted/fed diet regime and acclimated for 11 days. At day −3 and −1 pre-dose, serum was drawn at both fasted and 4 hours post-fed time points and analyzed for total cholesterol (Tc), LDL (LDLc), HDL cholesterol (HDLc) as well as triglycerides (TG), and PCSK9 plasma levels. Animals were randomized based on their day −3 LDLc levels. On the day of dosing (designated day 1), either 1 mg/kg or 5 mg/kg of LNP01-1a2 and 5 mg/kg LNP01-2a1 were injected, along with PBS and 1 mg/kg LNP01-ctrl as controls. All doses were well tolerated with no in-life findings. As the experiment progressed it became apparent (based on LDLc lowering) that the lower dose was not efficacious. We therefore dosed the PBS group animals on day 14 with 5 mg/kg LNP01-ctrl control siRNA, which could then serve as an additional control for the high dose groups of 5 mg/kg LNP01-1a2 and 5 mg/kg LNP01-2a1. Initially blood was drawn from animals on days 3, 4, 5, and 7 post-dose and Tc, HDLc, LDLc, and TGs concentrations were measured. Additional blood draws from the LNP01-1a2, LNP01-2a1 high dose groups were carried out at day 14 and day 21 post-dose (as the LDLc levels had not returned to baseline by day 7).

Figure 1B:
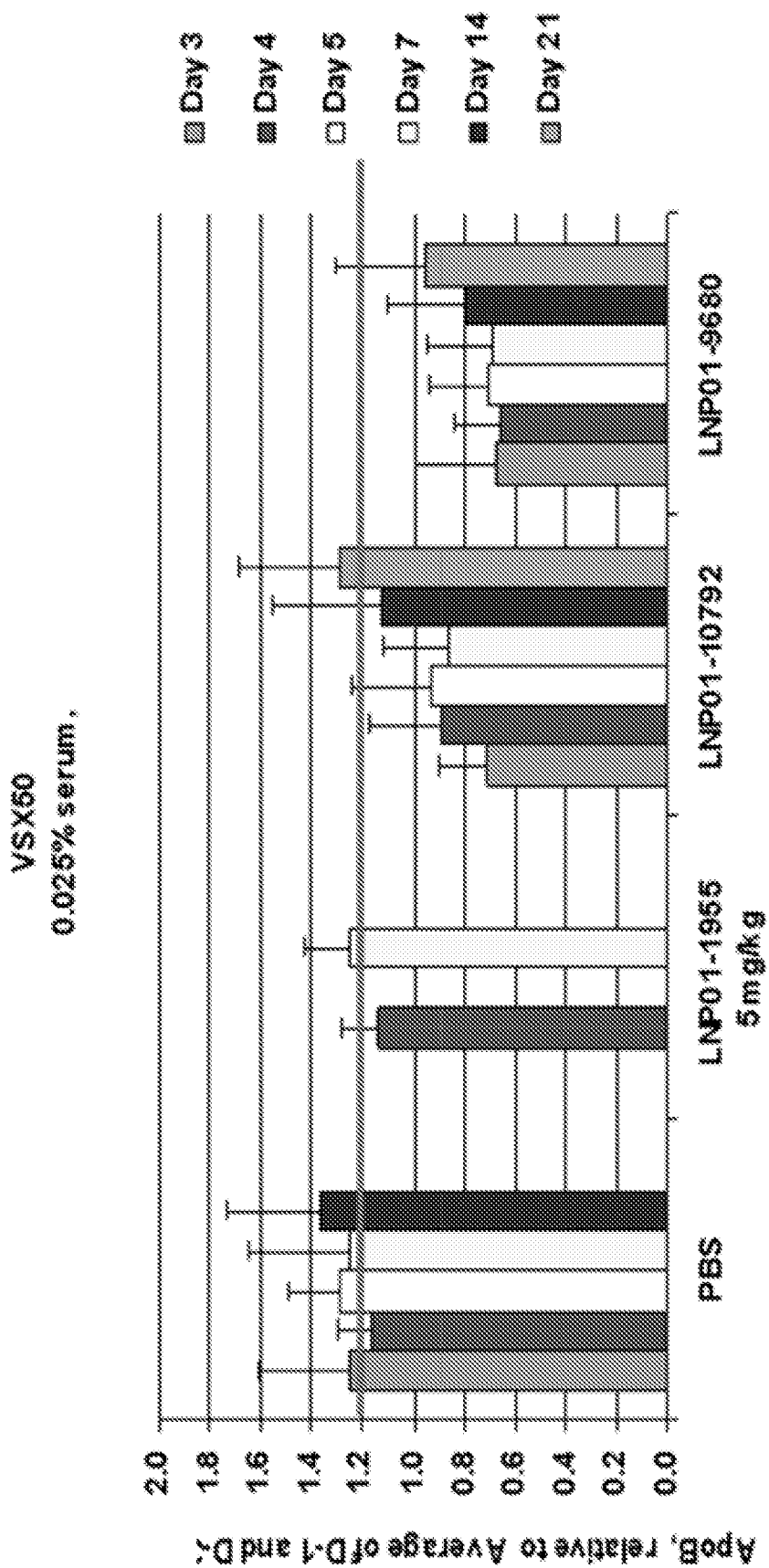
Figure 1C:
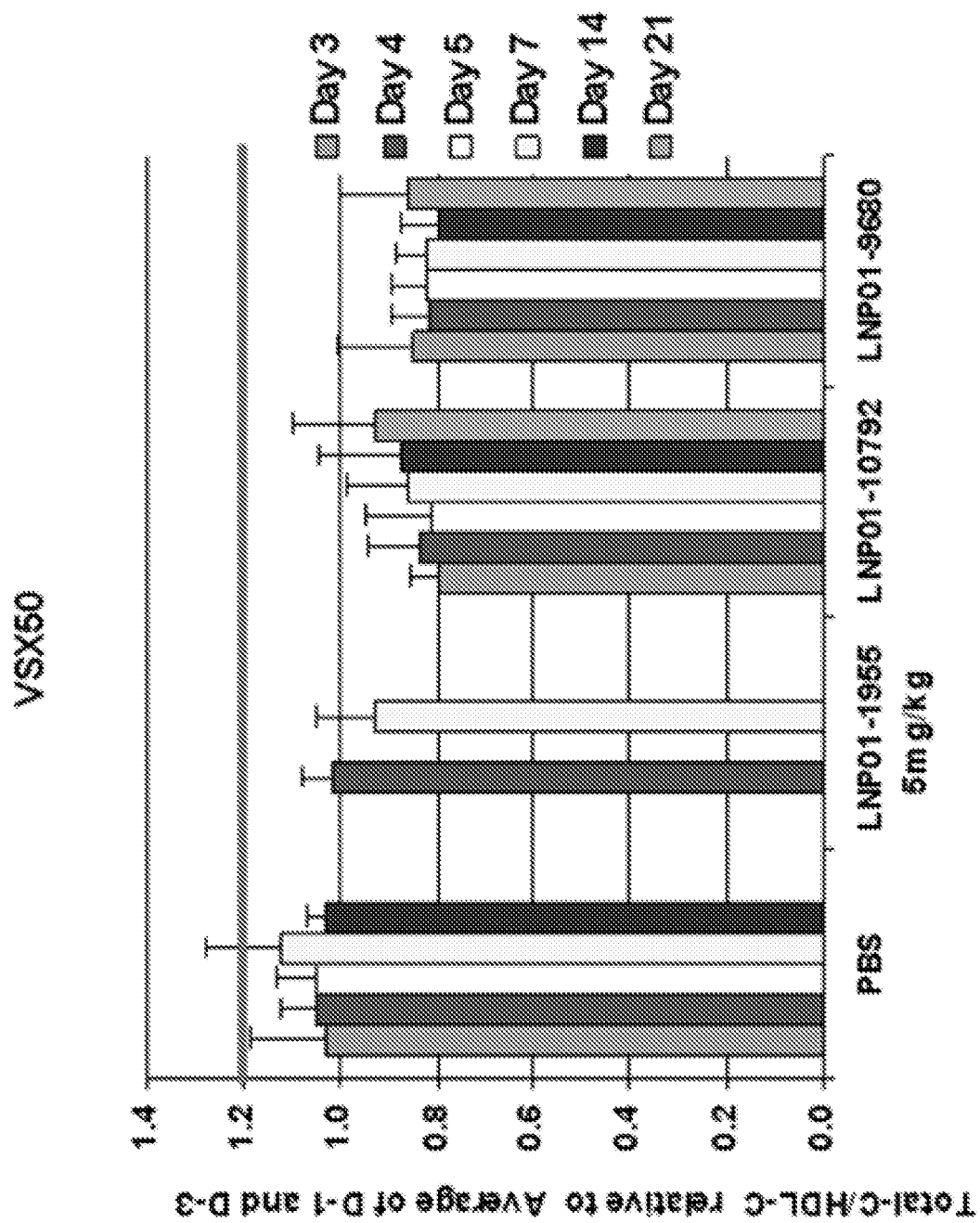
Figure 1D:
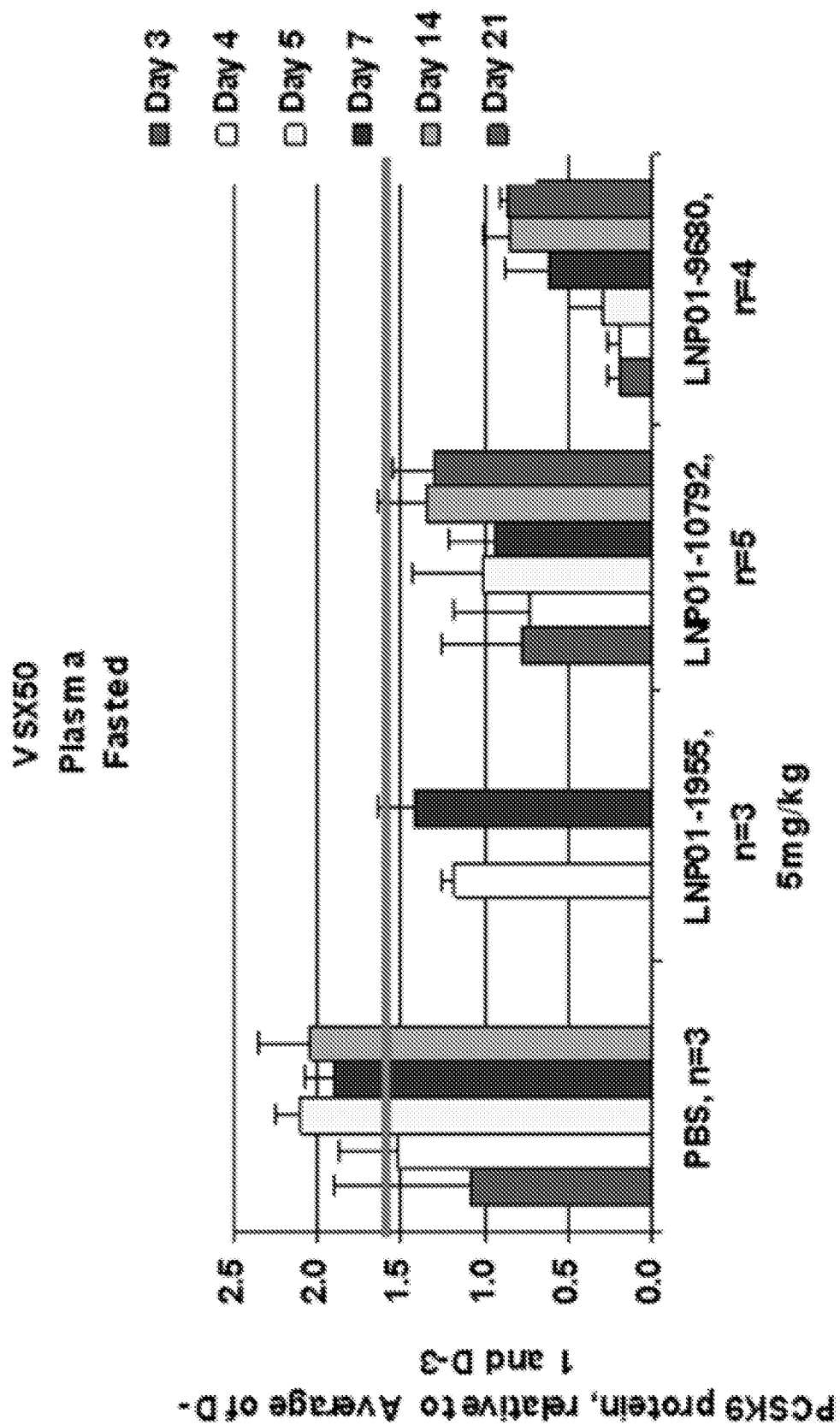

As shown in FIG. 1A, a single dose of LNP01-1a2 or LNP01-2a1 resulted in a statistically significant reduction of LDLc beginning at day 3 post-dose that returned to baseline over ~14 days (for LNP01-1a2) and ~21 days (LNP01-2a1). This effect was not seen in either the PBS, the control siRNA groups, or the 1 mg/kg treatment groups. LNP01-2a1 resulted in an average lowering of LDLc of 56% 72 hours post-dose, with 1 of 4 animals achieving nearly 70% LDLc, and all others achieving >50% LDLc decrease, as compared to pre-dose levels (see FIG. 1A). As expected, the lowering of LDLc in the treated animals also correlated with a reduction of circulating ApoB levels as measured by serum ELISA (FIG. 1B). Interestingly, the degree of LDLc lowering observed in this study of Cyno monkey was greater than those that have been reported for high dose statins, as well as, for other current standard of care compounds used for hypercholesterolemia. The onset of action is also much more acute than that of statins with effects being seen as early as 48 hours post-dose.

Neither LNP01-1a2 nor LNP01-2a1 treatments resulted in a lowering of HDLc. In fact, both molecules resulted (on average) in a trend towards a decreased Tc/HDL ratio (FIG.

1C). In addition, circulating triglyceride levels, and with the exception of one animal, ALT and AST levels were not significantly impacted.

Figure 2:
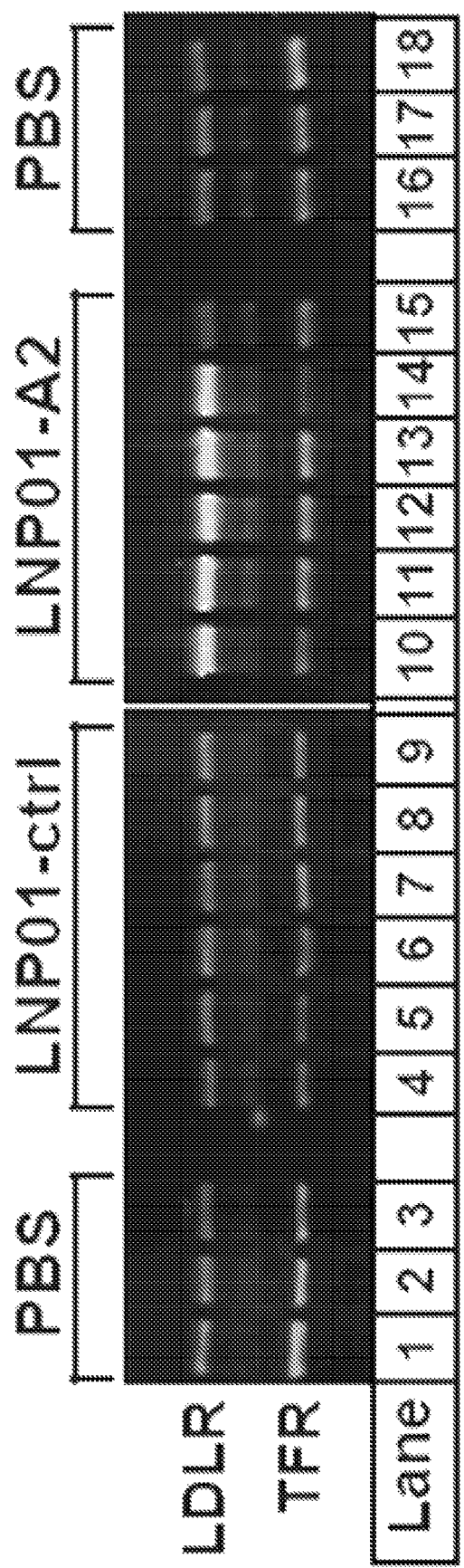
FIG. 2 is a Western blot showing that liver LDL receptor levels were upregulated following administration of PCSK9 siRNAs in rat.

PCSK9 protein levels were also measured in treated and control animals. As shown in FIG. 2, LNP01-1a2 and LNP01-2a1 treatment each resulted in trends toward decreased circulating PCSK9 protein levels versus pre-dose. Specifically, the more active siRNA LNP01-2a1 demonstrated significant reduction of circulating PCSK9 protein versus both PBS (day 3-21) and LNP01-ctrl siRNA control (day 4, day 7).

Example 2

Evaluation of SNALP-DLinDMA Formulated siRNAs

Figure 3:
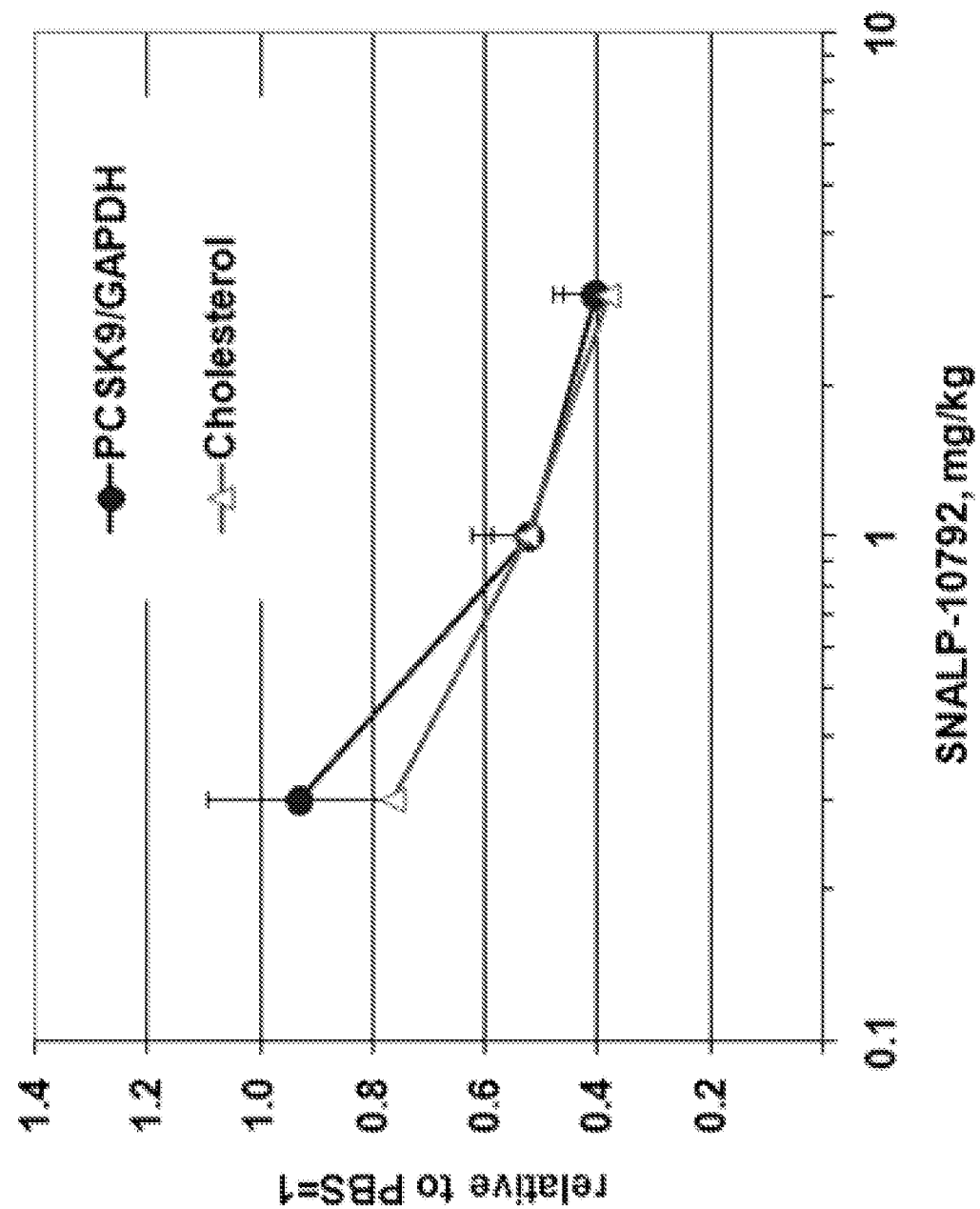
FIG. 3 is a graph showing the results of lipid formulated siRNAs on PCSK9 transcript levels and total serum cholesterol in rats.

Briefly, rats were dosed via tail injection with SNALP formulated siRNAs or PBS with a single dosage of about 0.3, 1.0, and 3.0 mg/kg of SNALP formulated AD-10792. Each dosage group included 5 rats. 72 hour post dosing rats were sacrificed and blood and liver samples were obtained, stored, and processed to determine PCSK9 mRNA and total serum cholesterol levels. The results are shown in FIG. 3. Compared to control PBS, SNALP formulated AD-10792 (FIG. 3A) had an ED50 of about 1.0 mg/kg for both lowering of PCSK9 transcript levels and total serum cholesterol levels. These results show that administration of SNALP formulated siRNA results in effective and efficient silencing of PCSK9 and subsequent lowering of total cholesterol in vivo.

Bolus Dosing

Bolus dosing of formulated siRNAs in Sprague-Dawley rats (5/group, 170-190 g body weight, Charles River Laboratories, MA) was performed by tail vein injection using a 27G needle. siRNAs were formulated in SNALP (and then dialyzed against PBS) and diluted with PBS to concentrations 0.066; 0.2 and 0.6 mg/ml allowing the delivery of 0.3; 1.0 and 3.0 mg/kg of SNALP formulated AD-10792 in 5 µl/g body weight. Rats were kept under an infrared lamp for approximately 3 min prior to dosing to ease injection.

72 hour post last dose rats were sacrificed by CO2-asphyxiation. 0.2 ml blood was collected by retro-orbital bleeding and the liver was harvested and frozen in liquid nitrogen. Serum and livers were stored at −80° C. Frozen livers were grinded using 6850 Freezer/Mill Cryogenic Grinder (SPEX CentriPrep, Inc) and powders stored at −80° C. until analysis.

PCSK9 mRNA levels were detected using the branched-DNA technology based kit from QuantiGene Reagent System (Panomics, USA) according to the protocol. 10-20 mg of frozen liver powders was lysed in 600 µl of 0.16 µg/ml Proteinase K (Epicentre, #MPRK092) in Tissue and Cell Lysis Solution (Epicentre, #MTC096H) at 65° C. for 3 hours. Then 10 µl of the lysates were added to 90 µl of Lysis Working Reagent (1 volume of stock Lysis Mixture in two volumes of water) and incubated at 52° C. overnight on Genospectra capture plates with probe sets specific to rat PCSK9 and rat GAPDH. Probes sets for rat PCSK9 and rat GAPDH were purchased from Panomics, USA. Chemo luminescence was read on a Victor2-Light (Perkin Elmer) as Relative light units. The ratio of rat PCSK9 mRNA to rat GAPDH mRNA in liver lysates was averaged over each treatment group and compared to a control group treated with PBS or a control group treated with an unrelated siRNA (blood coagulation factor VII).

Total serum cholesterol in rat serum was measured using the Total Cholesterol Assay (Wako, USA) according to manufacturer's instructions. Measurements were taken on a Victor2 1420 Multilabel Counter (Perkin Elmer) at 600 nm.

Example 3

Inhibition of PCSK9 Expression in Humans

A human subject is treated with a dsRNA targeted to a PCSK9 gene to inhibit expression of the PCSK9 gene and lower cholesterol levels for an extended period of time following a single dose.

A subject in need of treatment is selected or identified. The subject can be in need of LDL lowering, LDL lowering without lowering of HDL, ApoB lowering, or total cholesterol lowering. The identification of the subject can occur in a clinical setting, or elsewhere, e.g., in the subject's home through the subject's own use of a self-testing kit.

At time zero, a suitable first dose of an anti-PCSK9 siRNA is subcutaneously administered to the subject. The dsRNA is formulated as described herein. After a period of time following the first dose, e.g., 7 days, 14 days, and 21 days, the subject's condition is evaluated, e.g., by measuring LDL, ApoB, and/or total cholesterol levels. This measurement can be accompanied by a measurement of PCSK9 expression in said subject, and/or the products of the successful siRNA-targeting of PCSK9 mRNA. Other relevant criteria can also be measured. The number and strength of doses are adjusted according to the subject's needs.

After treatment, the subject's LDL, ApoB, or total cholesterol levels are lowered relative to the levels existing prior to the treatment, or relative to the levels measured in a similarly afflicted but untreated subject.

Example 4

Dose Response of SNALP-DlinDMA and XTC2 Formulated AD-10792 in Rats

Rats were treated with AD-10792 in two different formulations: a SNALP formulation with DlinDMA and a LNP formulation with XTC. Rats were treated via tail vein injection with the AD-10792 formulations. At day 3, total serum cholesterol and liver PCSK9 mRNA levels were determined. Rats were sacrificed by CO2-asphyxiation. 0.2 ml blood was collected by retro-orbital bleeding and the liver was harvested and frozen in liquid nitrogen. Serum and livers were stored at −80° C. Frozen livers were grinded using 6850 Freezer/Mill Cryogenic Grinder (SPEX CentriPrep, Inc) and powders stored at −80° C. until analysis.

PCSK9 mRNA levels were detected using the branched-DNA technology based kit from QuantiGene Reagent System (Panomics, USA) according to the protocol. 10-20 mg of frozen liver powders was lysed in 600 µl of 0.16 µg/ml Proteinase K (Epicentre, #MPRK092) in Tissue and Cell Lysis Solution (Epicentre, #MTC096H) at 65° C. for 3 hours. Then 10 µl of the lysates were added to 90 µl of Lysis Working Reagent (1 volume of stock Lysis Mixture in two volumes of water) and incubated at 52° C. overnight on Genospectra capture plates with probe sets specific to rat PCSK9 and rat GAPDH. Probes sets for rat PCSK9 and rat GAPDH were purchased from Panomics, USA. Chemo luminescence was read on a Victor2-Light (Perkin Elmer) as Relative light units. The ratio of rat PCSK9 mRNA to rat GAPDH mRNA in liver lysates was averaged over each treatment group and compared to a control group treated with PBS or a control group treated with an unrelated siRNA (blood coagulation factor VII).

Total serum cholesterol in rat serum was measured using the Total Cholesterol Assay (Wako, USA) according to manufacturer's instructions. Measurements were taken on a Victor2 1420 Multilabel Counter (Perkin Elmer) at 600 nm.

Figure 4:
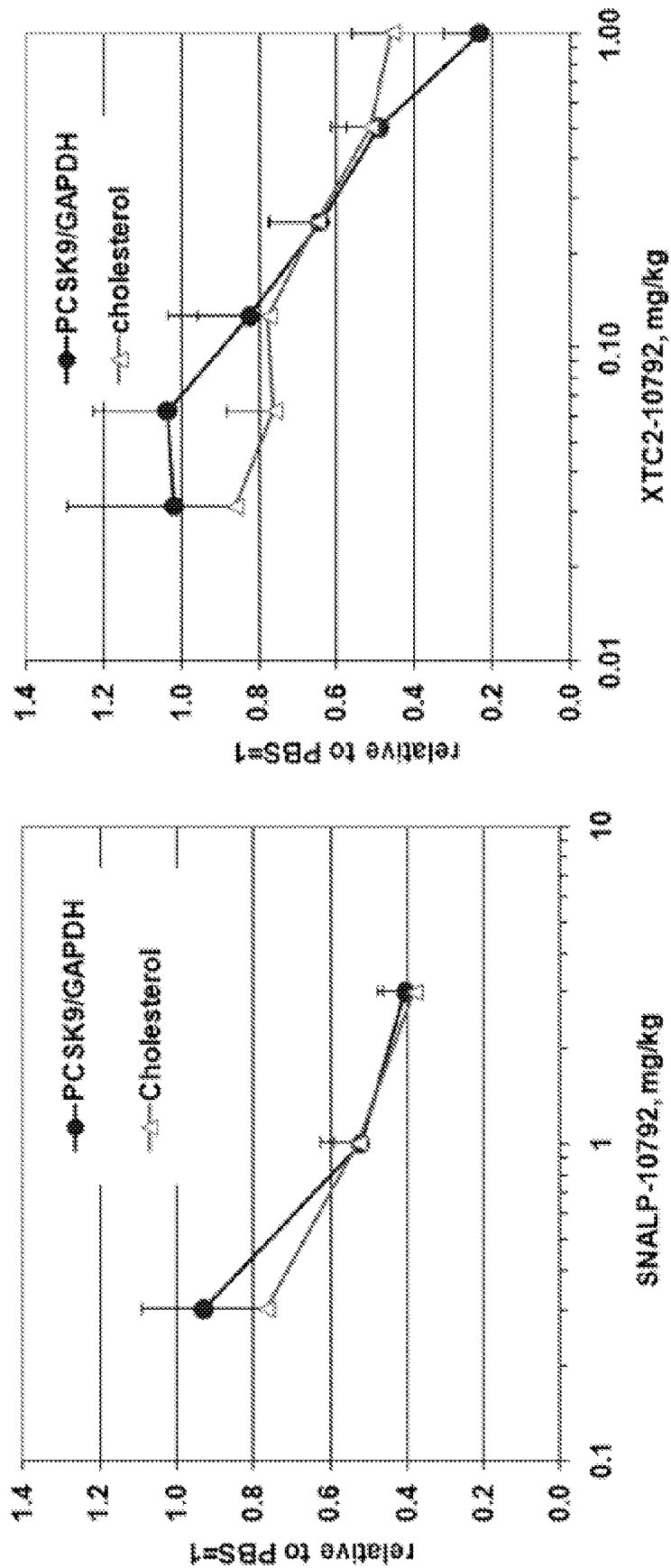
FIG. 4 shows the results of the SNALP and XTC2-PCSK9 siRNA dose response in rats.

The results are shown in the graph of FIG. 4. Administration of XTC formulated AD-10792 results in a lower EC50 of 0.4 mg/kg compared to administration of SNALP-DlinDMA formulated AD-10792 with an EC50 of 1.0 mg/kg.

Example 5

Maintenance of Decrease in Total Cholesterol Levels by Lower Dosage of AD-10792

Two different maintenance dosing regimens were investigated.

Rats were treated with 3 mg/kg bolus dose of SNALP-DlinDMA formulated AD-10792. At day 2, total serum cholesterol levels were determined. This was followed by once a week dosing at 1.0 and 0.3 mg/kg for four weeks. Rats were bled one day prior to repeated dosing and total serum cholesterol levels were determined. The negative control was PBS.

Figure 5:
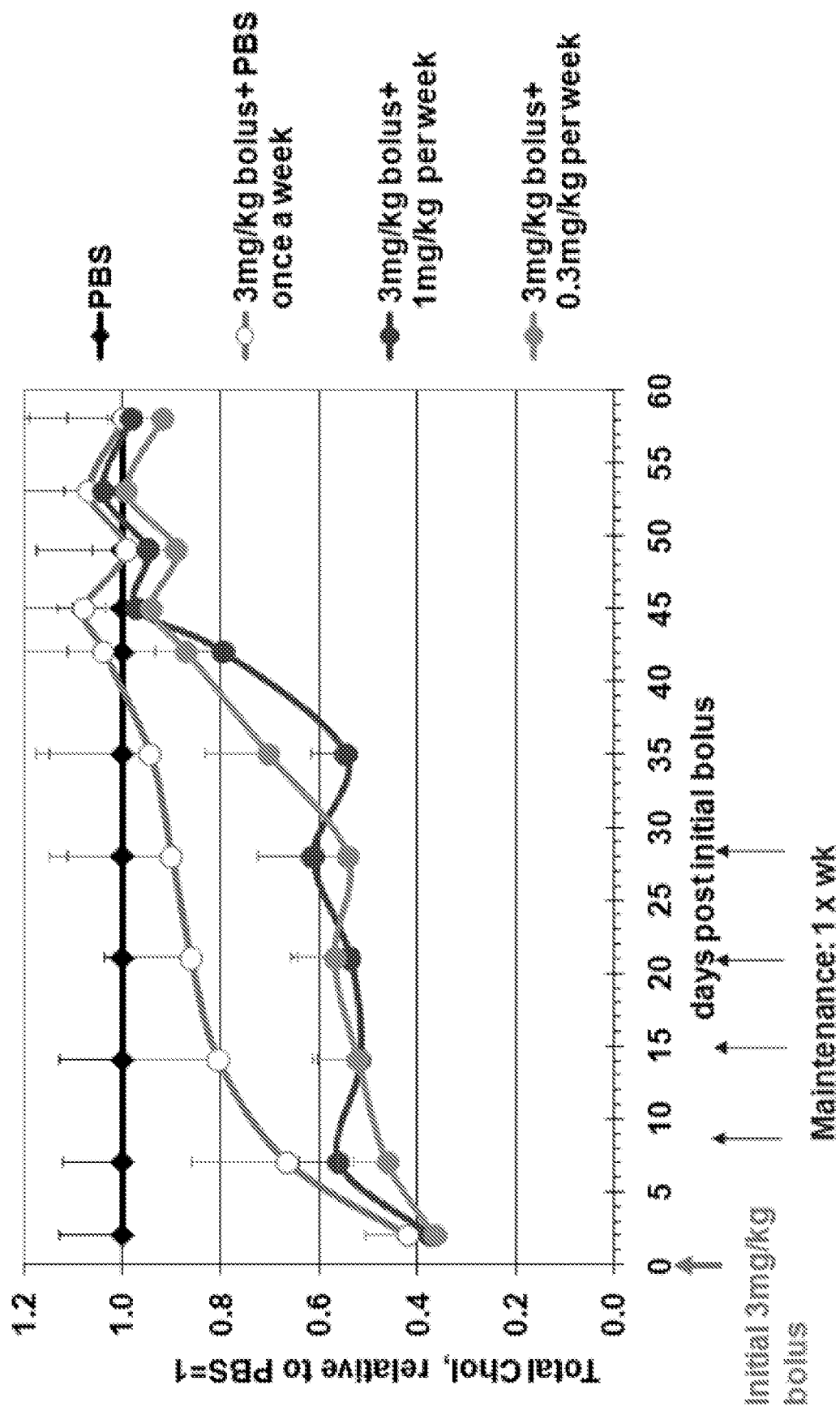
FIG. 5 shows the results of treatment with a maintenance dose of PCSK9 targeted siRNA.

The results are shown in the graph of FIG. 5. After 3 mg/kg bolus dose, total cholesterol levels decreased by 60% and were maintained at about 50% by repeated once a week 1.0 and 0.3 mg/kg dosing and come back to pre dose levels after repeated dosing is stopped.

A second maintenance dosing regimen was investigated. Rats were treated with 3 mg/kg bolus dose of SNALP-DlinDMA formulated AD-10792. At day 2, total serum cholesterol levels were determined. This was followed by once every 2 weeks dosing at 1.5 mg/kg for three weeks. Rats were bled one day prior to repeated dosing and total serum cholesterol levels were determined. The negative control was PBS.

Figure 6:
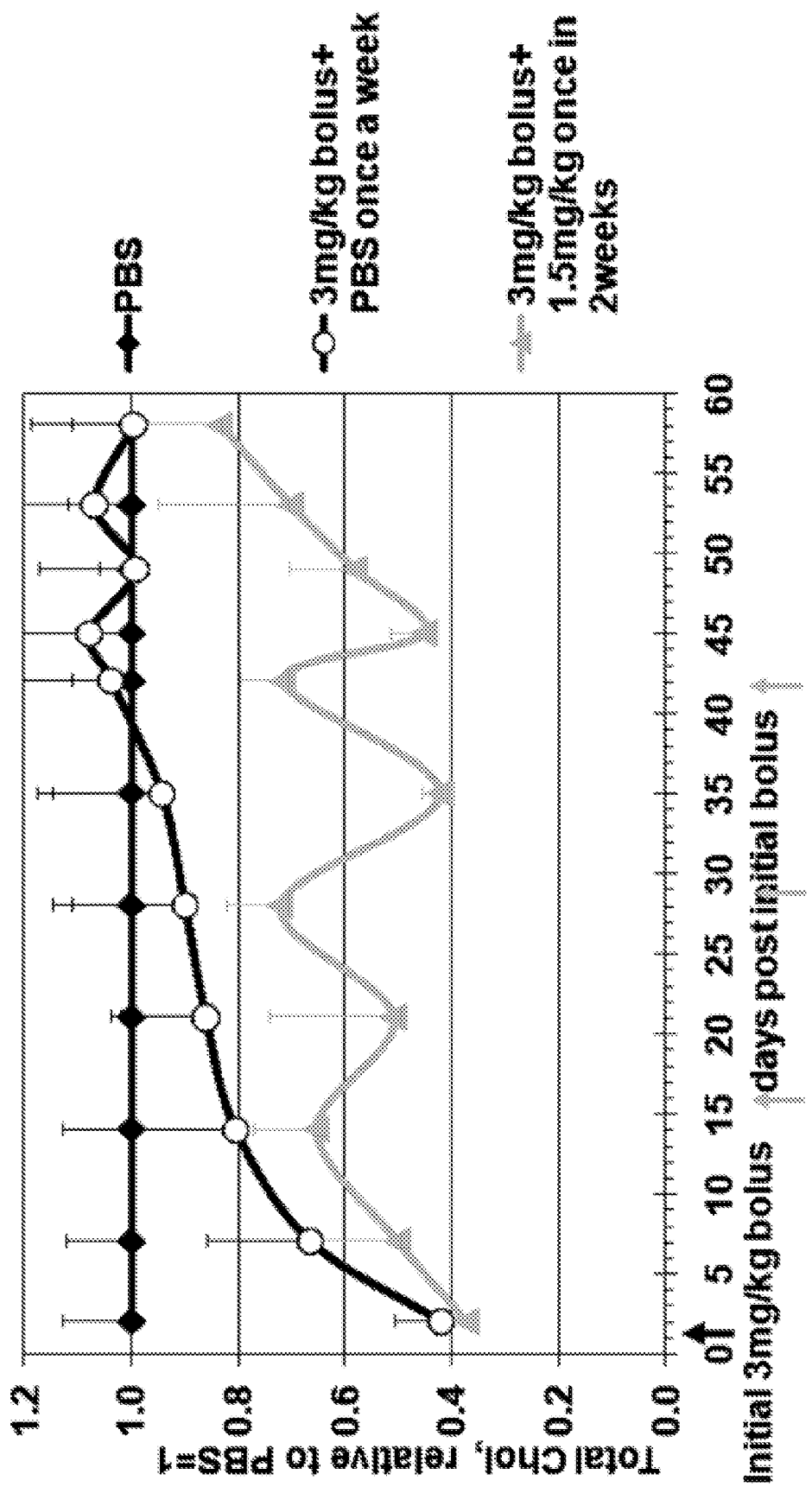
FIG. 6 the results of treatment with a maintenance dose of PCSK9 targeted siRNA.

The results are shown in the graph of FIG. 6. After 3 mg/kg bolus dose, total cholesterol levels decreased by 60% and were maintained at about 50% by repeated once every two weeks 1.5 mg/kg dosing and come back to pre dose levels after repeated dosing is stopped.

A 10 fold lower (than EC50), once a week, maintenance dose effectively maintains silencing with cholesterol levels returning to baseline by 15 days post last injection. Once in two weeks maintenance dosing of 1.5 mg/kg shows sinusoidal behavior.

The initial dose of PCSK9 increased LDLR levels as reflected by the decrease in total serum cholesterol. This increase in LDLR levels increased the efficacy of the PCSK9 targeted siRNA as reflected by the lower dosage of subsequent administration of AD-10792.

Example 6

Decrease in Target Gene Expression by Lower Dosage of AD12115 Following Administration of an Agent Different dosing regimens are investigated.

Rats or mice (in some instances engineered to express human Eg5) are treated with a 3.0 mg/kg bolus dose of SNALP-DlinDMA formulated AD-10792. At day 2, total serum cholesterol levels and Eg5 mRNA levels are determined. This is followed by once a week dosing for four weeks with AD12115 (Eg5) at the appropriate siRNA dose, e.g., 0.3 mg/kg or 1.0 mg/kg. Rats are bled and/or biopsied one day prior to repeated dosing and total cholesterol levels and Eg5 mRNA levels are determined. The negative control is PBS.

After the 3 mg/kg bolus dose, total cholesterol levels decrease. Eg5 mRNA levels significantly decrease following repeated once a week dosing with siRNA where the dose of siRNA required to achieve the significant decrease in mRNA expression is lower than if the siRNA had been administered without first administering the agent. Eg5 levels come back to pre-dose levels after repeated dosing is stopped. An approximately 10-fold lower (than EC50), once a week, siRNA dose effectively maintains gene silencing with mRNA levels returning to baseline by 15 days post last injection.

A second dosing regimen is investigated. Rats or mice are treated with a 3 mg/kg bolus dose of SNALP-DlinDMA formulated AD-10792. At day 2, total serum cholesterol levels and Eg5 mRNA levels are determined. This is followed by once every 2 weeks dosing with AD12115 at the appropriate siRNA dose, e.g., 1.5 mg/kg for three weeks. Rats are bled and/or biopsied one day prior to repeated dosing and total serum cholesterol levels and Eg5 mRNA levels are determined. The negative control is PBS.

After the 3 mg/kg bolus dose, total cholesterol levels decrease. Eg5 mRNA levels significantly decrease following repeated once every 2 weeks dosing with siRNA where the dose of siRNA required to achieve the significant decrease in mRNA expression is lower than if the siRNA had been administered without first administering the agent. Eg5 levels come back to pre-dose levels after repeated dosing is stopped.

A third dosing regimen is investigated. Rats or mice are treated with a dose of an agent, e.g., a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. At day 2, total serum cholesterol levels and Eg5 mRNA levels are determined. This is followed by once every 2 weeks or once a week dosing with AD12115 at the appropriate siRNA dose, e.g., 0.3 mg/kg, 1.0 mg/kg, or 1.5 mg/kg. Rats are bled and/or biopsied one day prior to repeated dosing and total serum cholesterol levels and Eg5 mRNA levels are determined. The negative control is PBS.

After the agent dose, total cholesterol levels decrease. Eg5 mRNA levels significantly decrease following repeated dosing with siRNA where the dose of siRNA required to achieve the significant decrease in mRNA expression is lower than if the siRNA had been administered without first administering the agent. Eg5 levels come back to pre-dose levels after repeated dosing is stopped. An approximately 5 to 10-fold lower (than EC50) siRNA dose effectively maintains gene silencing with mRNA levels returning to baseline by 15 days post last injection.

The initial dose of agent increases LDLR levels as reflected by the decrease in total serum cholesterol. This increase in LDLR levels increases the efficacy of the Eg5 targeted siRNA as reflected by the lower dosage of subsequent siRNA administration.

Example 7

Decrease in Target Gene Expression by Lower Dosage of AL-DP-4094 Following Administration of an Agent Different dosing regimens are investigated.

Rats or mice (in some instances engineered to express human VEGF) are treated with a 3.0 mg/kg bolus dose of SNALP-DlinDMA formulated AD-10792. At day 2, total serum cholesterol levels and VEGF mRNA levels are determined. This is followed by once a week dosing for four weeks with AL-DP-4094 (VEGF) at the appropriate siRNA dose, e.g., 0.3 mg/kg or 1.0 mg/kg. Rats are bled and/or biopsied one day prior to repeated dosing and total cholesterol levels and VEGF mRNA levels are determined. The negative control is PBS.

After the 3 mg/kg bolus dose, total cholesterol levels decrease. VEGF mRNA levels significantly decrease following repeated once a week dosing with siRNA where the dose of siRNA required to achieve the significant decrease in mRNA expression is lower than if the siRNA had been administered without first administering the agent. VEGF levels come back to pre-dose levels after repeated dosing is stopped. An approximately 10-fold lower (than EC50), once a week, siRNA dose effectively maintains gene silencing with mRNA levels returning to baseline by 15 days post last injection.

A second dosing regimen is investigated. Rats or mice are treated with a 3 mg/kg bolus dose of SNALP-DlinDMA formulated AD-10792. At day 2, total serum cholesterol levels and VEGF mRNA levels are determined. This is followed by once every 2 weeks dosing with AL-DP-4094 at the appropriate siRNA dose, e.g., 1.5 mg/kg for three weeks. Rats are bled and/or biopsied one day prior to repeated dosing and total serum cholesterol levels and VEGF mRNA levels are determined. The negative control is PBS.

After the 3 mg/kg bolus dose, total cholesterol levels decrease. VEGF mRNA levels significantly decrease following repeated once every 2 weeks dosing with siRNA where the dose of siRNA required to achieve the significant decrease in mRNA expression is lower than if the siRNA had been administered without first administering the agent. VEGF levels come back to pre-dose levels after repeated dosing is stopped.

A third dosing regimen is investigated. Rats or mice are treated with a dose of an agent, e.g., a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. At day 2, total serum cholesterol levels and VEGF mRNA levels are determined. This is followed by once every 2 weeks or once a week dosing with AL-DP-4094 at the appropriate siRNA dose, e.g., 0.3 mg/kg, 1.0 mg/kg, or 1.5 mg/kg. Rats are bled and/or biopsied one day prior to repeated dosing and total serum cholesterol levels and VEGF mRNA levels are determined. The negative control is PBS.

After the agent dose, total cholesterol levels decrease. VEGF mRNA levels significantly decrease following repeated dosing with siRNA where the dose of siRNA required to achieve the significant decrease in mRNA expression is lower than if the siRNA had been administered without first administering the agent. VEGF levels come back to pre-dose levels after repeated dosing is stopped. An approximately 5 to 10-fold lower (than EC50) siRNA dose effectively maintains gene silencing with mRNA levels returning to baseline by 15 days post last injection.

The initial dose of agent increases LDLR levels as reflected by the decrease in total serum cholesterol. This increase in LDLR levels increases the efficacy of the VEGF targeted siRNA as reflected by the lower dosage of subsequent siRNA administration.

Example 8

Decrease in Target Gene Expression by Lower Dosage of AD-18328 Following Administration of an Agent Different dosing regimens are investigated.

Rats or mice (in some instances engineered to express human TTR) are treated with a 3.0 mg/kg bolus dose of SNALP-DlinDMA formulated AD-10792. At day 2, total serum cholesterol levels and TTR mRNA levels are determined. This is followed by once a week dosing for four weeks with AD-18328 (TTR) at the appropriate siRNA dose, e.g., 0.3 mg/kg or 1.0 mg/kg. Rats are bled and/or biopsied one day prior to repeated dosing and total cholesterol levels and TTR mRNA levels are determined. The negative control is PBS.

After the 3 mg/kg bolus dose, total cholesterol levels decrease. TTR mRNA levels significantly decrease following repeated once a week dosing with siRNA where the dose of siRNA required to achieve the significant decrease in mRNA expression is lower than if the siRNA had been administered without first administering the agent. TTR levels come back to pre-dose levels after repeated dosing is stopped. An approximately 10-fold lower (than EC50), once a week, siRNA dose effectively maintains gene silencing with mRNA levels returning to baseline by 15 days post last injection.

A second dosing regimen is investigated. Rats or mice are treated with a 3 mg/kg bolus dose of SNALP-DlinDMA formulated AD-10792. At day 2, total serum cholesterol levels and TTR mRNA levels are determined. This is followed by once every 2 weeks dosing with AD-18328 at the appropriate siRNA dose, e.g., 1.5 mg/kg for three weeks. Rats are bled and/or biopsied one day prior to repeated dosing and total serum cholesterol levels and TTR mRNA levels are determined. The negative control is PBS.

After the 3 mg/kg bolus dose, total cholesterol levels decrease. TTR mRNA levels significantly decrease following repeated once every 2 weeks dosing with siRNA where the dose of siRNA required to achieve the significant decrease in mRNA expression is lower than if the siRNA had been administered without first administering the agent. TTR levels come back to pre-dose levels after repeated dosing is stopped.

A third dosing regimen is investigated. Rats or mice are treated with a dose of an agent, e.g., a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. At day 2, total serum cholesterol levels and TTR mRNA levels are determined. This is followed by once every 2 weeks or once a week dosing with AD-18328 at the appropriate siRNA dose, e.g., 0.3 mg/kg, 1.0 mg/kg, or 1.5 mg/kg. Rats are bled and/or biopsied one day prior to repeated dosing and total serum cholesterol levels and TTR mRNA levels are determined. The negative control is PBS.

After the agent dose, total cholesterol levels decrease. TTR mRNA levels significantly decrease following repeated dosing with siRNA where the dose of siRNA required to achieve the significant decrease in mRNA expression is lower than if the siRNA had been administered without first administering the agent. TTR levels come back to pre-dose levels after repeated dosing is stopped. An approximately 5 to 10-fold lower (than EC50) siRNA dose effectively maintains gene silencing with mRNA levels returning to baseline by 15 days post last injection.

The initial dose of agent increases LDLR levels as reflected by the decrease in total serum cholesterol. This increase in LDLR levels increases the efficacy of the TTR targeted siRNA as reflected by the lower dosage of subsequent siRNA administration.

Example 9

Decrease in Target Gene Expression by Lower Dosage of AD-20057 Following Administration of an Agent Different dosing regimens are investigated.

Rats or mice (in some instances engineered to express human GNAQ) are treated with a 3.0 mg/kg bolus dose of SNALP-DlinDMA formulated AD-10792. At day 2, total serum cholesterol levels and GNAQ mRNA levels are determined. This is followed by once a week dosing for four weeks with AD-20057 (GNAQ) at the appropriate siRNA dose, e.g., 0.3 mg/kg or 1.0 mg/kg. Rats are bled and/or biopsied one day prior to repeated dosing and total cholesterol levels and GNAQ mRNA levels are determined. The negative control is PBS.

After the 3 mg/kg bolus dose, total cholesterol levels decrease. GNAQ mRNA levels significantly decrease following repeated once a week dosing with siRNA where the dose of siRNA required to achieve the significant decrease in mRNA expression is lower than if the siRNA had been administered without first administering the agent. GNAQ levels come back to pre-dose levels after repeated dosing is stopped. An approximately 10-fold lower (than EC50), once a week, siRNA dose effectively maintains gene silencing with mRNA levels returning to baseline by 15 days post last injection.

A second dosing regimen is investigated. Rats or mice are treated with a 3 mg/kg bolus dose of SNALP-DlinDMA formulated AD-10792. At day 2, total serum cholesterol levels and GNAQ mRNA levels are determined. This is followed by once every 2 weeks dosing with AD-20057 at the appropriate siRNA dose, e.g., 1.5 mg/kg for three weeks. Rats are bled and/or biopsied one day prior to repeated dosing and total serum cholesterol levels and GNAQ mRNA levels are determined. The negative control is PBS.

After the 3 mg/kg bolus dose, total cholesterol levels decrease. GNAQ mRNA levels significantly decrease following repeated once every 2 weeks dosing with siRNA where the dose of siRNA required to achieve the significant decrease in mRNA expression is lower than if the siRNA had been administered without first administering the agent. GNAQ levels come back to pre-dose levels after repeated dosing is stopped.

A third dosing regimen is investigated. Rats or mice are treated with a dose of an agent, e.g., a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. At day 2, total serum cholesterol levels and GNAQ mRNA levels are determined. This is followed by once every 2 weeks or once a week dosing with AD-20057 at the appropriate siRNA dose, e.g., 0.3 mg/kg, 1.0 mg/kg, or 1.5 mg/kg. Rats are bled and/or biopsied one day prior to repeated dosing and total serum cholesterol levels and GNAQ mRNA levels are determined. The negative control is PBS.

After the agent dose, total cholesterol levels decrease. GNAQ mRNA levels significantly decrease following repeated dosing with siRNA where the dose of siRNA required to achieve the significant decrease in mRNA expression is lower than if the siRNA had been administered without first administering the agent. GNAQ levels come back to pre-dose levels after repeated dosing is stopped. An approximately 5 to 10-fold lower (than EC50) siRNA dose effectively maintains gene silencing with mRNA levels returning to baseline by 15 days post last injection.

The initial dose of agent increases LDLR levels as reflected by the decrease in total serum cholesterol. This increase in LDLR levels increases the efficacy of the GNAQ targeted siRNA as reflected by the lower dosage of subsequent siRNA administration.

Example 10

Decrease in Target Gene Expression by Lower Dosage of AL-DP-5997 Following Administration of an Agent Different dosing regimens are investigated.

Rats or mice (in some instances engineered to express human HTT) are treated with a 3.0 mg/kg bolus dose of SNALP-DlinDMA formulated AD-10792. At day 2, total serum cholesterol levels and HTT mRNA levels are determined. This is followed by once a week dosing for four weeks with AL-DP-5997 (HTT) at the appropriate siRNA dose, e.g., 0.3 mg/kg or 1.0 mg/kg. Rats are bled and/or biopsied one day prior to repeated dosing and total cholesterol levels and HTT mRNA levels are determined. The negative control is PBS.

After the 3 mg/kg bolus dose, total cholesterol levels decrease. HTT mRNA levels significantly decrease following repeated once a week dosing with siRNA where the dose of siRNA required to achieve the significant decrease in mRNA expression is lower than if the siRNA had been administered without first administering the agent. HTT levels come back to pre-dose levels after repeated dosing is stopped. An approximately 10-fold lower (than EC50), once a week, siRNA dose effectively maintains gene silencing with mRNA levels returning to baseline by 15 days post last injection.

A second dosing regimen is investigated. Rats or mice are treated with a 3 mg/kg bolus dose of SNALP-DlinDMA formulated AD-10792. At day 2, total serum cholesterol levels and HTT mRNA levels are determined. This is followed by once every 2 weeks dosing with AL-DP-5997 at the appropriate siRNA dose, e.g., 1.5 mg/kg for three weeks. Rats are bled and/or biopsied one day prior to repeated dosing and total serum cholesterol levels and HTT mRNA levels are determined. The negative control is PBS.

After the 3 mg/kg bolus dose, total cholesterol levels decrease. HTT mRNA levels significantly decrease following repeated once every 2 weeks dosing with siRNA where the dose of siRNA required to achieve the significant decrease in mRNA expression is lower than if the siRNA had been administered without first administering the agent. HTT levels come back to pre-dose levels after repeated dosing is stopped.

A third dosing regimen is investigated. Rats or mice are treated with a dose of an agent, e.g., a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. At day 2, total serum cholesterol levels and HTT mRNA levels are determined. This is followed by once every 2 weeks or once a week dosing with AL-DP-5997 at the appropriate siRNA dose, e.g., 0.3 mg/kg, 1.0 mg/kg, or 1.5 mg/kg. Rats are bled and/or biopsied one day prior to repeated dosing and total serum cholesterol levels and HTT mRNA levels are determined. The negative control is PBS.

After the agent dose, total cholesterol levels decrease. HTT mRNA levels significantly decrease following repeated dosing with siRNA where the dose of siRNA required to achieve the significant decrease in mRNA expression is lower than if the siRNA had been administered without first administering the agent. HTT levels come back to pre-dose levels after repeated dosing is stopped. An approximately 5 to 10-fold lower (than EC50) siRNA dose effectively maintains gene silencing with mRNA levels returning to baseline by 15 days post last injection.

The initial dose of agent increases LDLR levels as reflected by the decrease in total serum cholesterol. This increase in LDLR levels increases the efficacy of the HTT targeted siRNA as reflected by the lower dosage of subsequent siRNA administration.

Example 11

Decrease in Target Gene Expression by Lower Dosage of RNA Agent Number 35 Following Administration of an Agent Different dosing regimens are investigated.

Rats or mice (in some instances engineered to express human APOB) are treated with a 3.0 mg/kg bolus dose of SNALP-DlinDMA formulated AD-10792. At day 2, total serum cholesterol levels and APOB mRNA levels are determined. This is followed by once a week dosing for four weeks with RNA agent number 35 (APOB) at the appropriate siRNA dose, e.g., 0.3 mg/kg or 1.0 mg/kg. Rats are bled and/or biopsied one day prior to repeated dosing and total cholesterol levels and APOB mRNA levels are determined. The negative control is PBS.

After the 3 mg/kg bolus dose, total cholesterol levels decrease. APOB mRNA levels significantly decrease following repeated once a week dosing with siRNA where the dose of siRNA required to achieve the significant decrease in mRNA expression is lower than if the siRNA had been administered without first administering the agent. APOB levels come back to pre-dose levels after repeated dosing is stopped. An approximately 10-fold lower (than EC50), once a week, siRNA dose effectively maintains gene silencing with mRNA levels returning to baseline by 15 days post last injection.

A second dosing regimen is investigated. Rats or mice are treated with a 3 mg/kg bolus dose of SNALP-DlinDMA formulated AD-10792. At day 2, total serum cholesterol levels and APOB mRNA levels are determined. This is followed by once every 2 weeks dosing with RNA agent number 35 at the appropriate siRNA dose, e.g., 1.5 mg/kg for three weeks. Rats are bled and/or biopsied one day prior to repeated dosing and total serum cholesterol levels and APOB mRNA levels are determined. The negative control is PBS.

After the 3 mg/kg bolus dose, total cholesterol levels decrease. APOB mRNA levels significantly decrease following repeated once every 2 weeks dosing with siRNA where the dose of siRNA required to achieve the significant decrease in mRNA expression is lower than if the siRNA had been administered without first administering the agent. APOB levels come back to pre-dose levels after repeated dosing is stopped.

A third dosing regimen is investigated. Rats or mice are treated with a dose of an agent, e.g., a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. At day 2, total serum cholesterol levels and APOB mRNA levels are determined. This is followed by once every 2 weeks or once a week dosing with RNA agent number 35 at the appropriate siRNA dose, e.g., 0.3 mg/kg, 1.0 mg/kg, or 1.5 mg/kg. Rats are bled and/or biopsied one day prior to repeated dosing and total serum cholesterol levels and APOB mRNA levels are determined. The negative control is PBS.

After the agent dose, total cholesterol levels decrease. APOB mRNA levels significantly decrease following repeated dosing with siRNA where the dose of siRNA required to achieve the significant decrease in mRNA expression is lower than if the siRNA had been administered without first administering the agent. APOB levels come back to pre-dose levels after repeated dosing is stopped. An approximately 5 to 10-fold lower (than EC50) siRNA dose effectively maintains gene silencing with mRNA levels returning to baseline by 15 days post last injection.

The initial dose of agent increases LDLR levels as reflected by the decrease in total serum cholesterol. This increase in LDLR levels increases the efficacy of the ApoB targeted siRNA as reflected by the lower dosage of subsequent siRNA administration.

Example 12

Inhibition of PCSK9 Expression in Humans with a Lower Dose of siRNA Following Administration of an Agent A human subject is treated with a siRNA targeted to a PCSK9 gene to inhibit expression of the PCSK9 gene and lower total cholesterol levels for an extended period of time following an agent dose.

A human subject in need of treatment of a condition associated with PCSK9 expression is selected or identified. The subject can be in need of LDL lowering, LDL lowering without lowering of HDL, ApoB lowering, or total cholesterol lowering. The identification of the subject can occur in a clinical setting, or elsewhere, e.g., in the subject's home through the subject's own use of a self-testing kit.

At time zero, a suitable dose of an agent is administered to the human subject. The agent can be, e.g., a PCSK9 siRNA, a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. Following administration of the agent dose to the subject, a suitable first siRNA dose of an anti-PCSK9 siRNA is subcutaneously administered to the subject. The siRNA is formulated as described herein. A series of subsequent siRNA doses can be administered to the subject as needed, e.g., once a week or once every two weeks or once every month. The siRNA dose(s) required to achieve significant PCSK9 gene silencing is less than if the agent had not been administered to the subject prior to the siRNA dose(s). After a period of time following the first siRNA dose or series of siRNA doses, e.g., 1 day, 2 days, 3, days, 4 days, 5 days, 7 days, 14 days, and/or 21 days, the subject's condition is evaluated, e.g., by measuring LDL, ApoB, and/or total cholesterol levels. This measurement can be accompanied by a measurement of PCSK9 expression in the subject, and/or the products of the successful siRNA-targeting of PCSK9 mRNA. Other relevant criteria can also be measured. The number and strength of doses are adjusted according to the subject's needs.

After treatment, the subject's PCSK9 mRNA levels are lowered relative to the levels existing prior to the treatment, or relative to the levels measured in a similarly afflicted but untreated subject. The initial dose of agent increases LDLR levels in the subject as reflected by the decrease in total serum cholesterol. This increase in LDLR levels increases the efficacy of the siRNA as reflected by the lower dosage of subsequent siRNA administration required to significantly inhibit target gene expression.

Example 13

Inhibition of Eg5 Expression in Humans with a Lower Dose of siRNA Following Administration of an Agent A human subject is treated with a siRNA targeted to an Eg5 gene to inhibit expression of the Eg5 gene and lower total cholesterol levels for an extended period of time following an agent dose.

A human subject in need of treatment of a condition associated with Eg5 expression is selected or identified. The identification of the subject can occur in a clinical setting, or elsewhere, e.g., in the subject's home through the subject's own use of a self-testing kit.

At time zero, a suitable dose of an agent is administered to the human subject. The agent can be, e.g., a PCSK9 siRNA, a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. Following administration of the agent dose to the subject, a suitable first siRNA dose of an anti-PCSK9 siRNA is subcutaneously administered to the subject. The siRNA is formulated as described herein. A series of subsequent siRNA doses can be administered to the subject as needed, e.g., once a week or once every two weeks or once every month. The siRNA dose(s) required to achieve significant Eg5 gene silencing is less than if the agent had not been administered to the subject prior to the siRNA dose(s). After a period of time following the first siRNA dose or series of siRNA doses, e.g., 1 day, 2 days, 3, days, 4 days, 5 days, 7 days, 14 days, and/or 21 days, the subject's condition is evaluated, e.g., by measuring Eg5 expression in the subject, and/or the products of the successful siRNA-targeting of Eg5 mRNA. Other relevant criteria can also be measured. The number and strength of doses are adjusted according to the subject's needs.

After treatment, the subject's Eg5 mRNA levels are lowered relative to the levels existing prior to the treatment, or relative to the levels measured in a similarly afflicted but untreated subject. The initial dose of agent increases LDLR levels in the subject as reflected by the decrease in total serum cholesterol. This increase in LDLR levels increases the efficacy of the siRNA as reflected by the lower dosage of subsequent siRNA administration required to significantly inhibit target gene expression.

Example 14

Inhibition of VEGF Expression in Humans with a Lower Dose of siRNA Following Administration of an Agent A human subject is treated with a siRNA targeted to a VEGF gene to inhibit expression of the VEGF gene and lower total cholesterol levels for an extended period of time following an agent dose.

A human subject in need of treatment of a condition associated with VEGF expression is selected or identified. The identification of the subject can occur in a clinical setting, or elsewhere, e.g., in the subject's home through the subject's own use of a self-testing kit.

At time zero, a suitable dose of an agent is administered to the human subject. The agent can be, e.g., a PCSK9 siRNA, a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. Following administration of the agent dose to the subject, a suitable first siRNA dose of an anti-PCSK9 siRNA is subcutaneously administered to the subject. The siRNA is formulated as described herein. A series of subsequent siRNA doses can be administered to the subject as needed, e.g., once a week or once every two weeks or once every month. The siRNA dose(s) required to achieve significant VEGF gene silencing is less than if the agent had not been administered to the subject prior to the siRNA dose(s). After a period of time following the first siRNA dose or series of siRNA doses, e.g., 1 day, 2 days, 3, days, 4 days, 5 days, 7 days, 14 days, and/or 21 days, the subject's condition is evaluated, e.g., by measuring VEGF expression in the subject, and/or the products of the successful siRNA-targeting of VEGF mRNA. Other relevant criteria can also be measured. The number and strength of doses are adjusted according to the subject's needs.

After treatment, the subject's VEGF mRNA levels are lowered relative to the levels existing prior to the treatment, or relative to the levels measured in a similarly afflicted but untreated subject. The initial dose of agent increases LDLR levels in the subject as reflected by the decrease in total serum cholesterol. This increase in LDLR levels increases the efficacy of the siRNA as reflected by the lower dosage of subsequent siRNA administration required to significantly inhibit target gene expression.

Example 15

Inhibition of TTR Expression in Humans with a Lower Dose of siRNA Following Administration of an Agent A human subject is treated with a siRNA targeted to a TTR gene to inhibit expression of the TTR gene and lower total cholesterol levels for an extended period of time following an agent dose.

A human subject in need of treatment of a condition associated with TTR expression is selected or identified. The identification of the subject can occur in a clinical setting, or elsewhere, e.g., in the subject's home through the subject's own use of a self-testing kit.

At time zero, a suitable dose of an agent is administered to the human subject. The agent can be, e.g., a PCSK9 siRNA, a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. Following administration of the agent dose to the subject, a suitable first siRNA dose of an anti-PCSK9 siRNA is subcutaneously administered to the subject. The siRNA is formulated as described herein. A series of subsequent siRNA doses can be administered to the subject as needed, e.g., once a week or once every two weeks or once every month. The siRNA dose(s) required to achieve significant TTR gene silencing is less than if the agent had not been administered to the subject prior to the siRNA dose(s). After a period of time following the first siRNA dose or series of siRNA doses, e.g., 1 day, 2 days, 3, days, 4 days, 5 days, 7 days, 14 days, and/or 21 days, the subject's condition is evaluated, e.g., by measuring TTR expression in the subject, and/or the products of the successful siRNA-targeting of TTR mRNA. Other relevant criteria can also be measured. The number and strength of doses are adjusted according to the subject's needs.

After treatment, the subject's TTR mRNA levels are lowered relative to the levels existing prior to the treatment, or relative to the levels measured in a similarly afflicted but untreated subject. The initial dose of agent increases LDLR levels in the subject as reflected by the decrease in total serum cholesterol. This increase in LDLR levels increases the efficacy of the siRNA as reflected by the lower dosage of subsequent siRNA administration required to significantly inhibit target gene expression.

Those skilled in the art are familiar with methods and compositions in addition to those specifically set out in the present disclosure which will allow them to practice this invention to the full scope of the claims hereinafter appended.

Example 16

Inhibition of GNAQ Expression in Humans with a Lower Dose of siRNA Following Administration of an Agent A human subject is treated with a siRNA targeted to a GNAQ gene to inhibit expression of the GNAQ gene and lower total cholesterol levels for an extended period of time following an agent dose.

A human subject in need of treatment of a condition associated with GNAQ expression is selected or identified. The identification of the subject can occur in a clinical setting, or elsewhere, e.g., in the subject's home through the subject's own use of a self-testing kit.

At time zero, a suitable dose of an agent is administered to the human subject. The agent can be, e.g., a PCSK9 siRNA, a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. Following administration of the agent dose to the subject, a suitable first siRNA dose of an anti-PCSK9 siRNA is subcutaneously administered to the subject. The siRNA is formulated as described herein. A series of subsequent siRNA doses can be administered to the subject as needed, e.g., once a week or once every two weeks or once every month. The siRNA dose(s) required to achieve significant GNAQ gene silencing is less than if the agent had not been administered to the subject prior to the siRNA dose(s). After a period of time following the first siRNA dose or series of siRNA doses, e.g., 1 day, 2 days, 3, days, 4 days, 5 days, 7 days, 14 days, and/or 21 days, the subject's condition is evaluated, e.g., by measuring GNAQ expression in the subject, and/or the products of the successful siRNA-targeting of GNAQ mRNA. Other relevant criteria can also be measured. The number and strength of doses are adjusted according to the subject's needs.

After treatment, the subject's GNAQ mRNA levels are lowered relative to the levels existing prior to the treatment, or relative to the levels measured in a similarly afflicted but untreated subject. The initial dose of agent increases LDLR levels in the subject as reflected by the decrease in total serum cholesterol. This increase in LDLR levels increases the efficacy of the siRNA as reflected by the lower dosage of subsequent siRNA administration required to significantly inhibit target gene expression.

Example 17

Inhibition of HTT Expression in Humans with a Lower Dose of siRNA Following Administration of an Agent A human subject is treated with a siRNA targeted to a HTT gene to inhibit expression of the HTT gene and lower total cholesterol levels for an extended period of time following an agent dose.

A human subject in need of treatment of a condition associated with HTT expression is selected or identified. The identification of the subject can occur in a clinical setting, or elsewhere, e.g., in the subject's home through the subject's own use of a self-testing kit.

At time zero, a suitable dose of an agent is administered to the human subject. The agent can be, e.g., a PCSK9 siRNA, a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. Following administration of the agent dose to the subject, a suitable first siRNA dose of an anti-PCSK9 siRNA is subcutaneously administered to the subject. The siRNA is formulated as described herein. A series of subsequent siRNA doses can be administered to the subject as needed, e.g., once a week or once every two weeks or once every month. The siRNA dose(s) required to achieve significant HTT gene silencing is less than if the agent had not been administered to the subject prior to the siRNA dose(s). After a period of time following the first siRNA dose or series of siRNA doses, e.g., 1 day, 2 days, 3, days, 4 days, 5 days, 7 days, 14 days, and/or 21 days, the subject's condition is evaluated, e.g., by measuring HTT expression in the subject, and/or the products of the successful siRNA-targeting of HTT mRNA. Other relevant criteria can also be measured. The number and strength of doses are adjusted according to the subject's needs.

After treatment, the subject's HTT mRNA levels are lowered relative to the levels existing prior to the treatment, or relative to the levels measured in a similarly afflicted but untreated subject. The initial dose of agent increases LDLR levels in the subject as reflected by the decrease in total serum cholesterol. This increase in LDLR levels increases the efficacy of the siRNA as reflected by the lower dosage of subsequent siRNA administration required to significantly inhibit target gene expression.

Those skilled in the art are familiar with methods and compositions in addition to those specifically set out in the present disclosure which will allow them to practice this invention to the full scope of the claims hereinafter appended.

Example 18

Inhibition of APOB Expression in Humans with a Lower Dose of siRNA Following Administration of an Agent A human subject is treated with a siRNA targeted to an APOB gene to inhibit expression of the APOB gene and lower total cholesterol levels for an extended period of time following an agent dose.

A human subject in need of treatment of a condition associated with APOB expression is selected or identified. The identification of the subject can occur in a clinical setting, or elsewhere, e.g., in the subject's home through the subject's own use of a self-testing kit.

At time zero, a suitable dose of an agent is administered to the human subject. The agent can be, e.g., a PCSK9 siRNA, a statin, an estradiol, berberine, a HMG CoA reductase inhibitor, a squalene synthetase inhibitor, a HMG CoA synthetase inhibitor, a fenofibrate, a LDLR RNAa, an IDOL targeted siRNA, niacin, and/or ezetimibe. Following administration of the agent dose to the subject, a suitable first siRNA dose of an anti-PCSK9 siRNA is subcutaneously administered to the subject. The siRNA is formulated as described herein. A series of subsequent siRNA doses can be administered to the subject as needed, e.g., once a week or once every two weeks or once every month. The siRNA dose(s) required to achieve significant APOB gene silencing is less than if the agent had not been administered to the subject prior to the siRNA dose(s). After a period of time following the first siRNA dose or series of siRNA doses, e.g., 1 day, 2 days, 3, days, 4 days, 5 days, 7 days, 14 days, and/or 21 days, the subject's condition is evaluated, e.g., by measuring APOB expression in the subject, and/or the products of the successful siRNA-targeting of APOB mRNA. Other relevant criteria can also be measured. The number and strength of doses are adjusted according to the subject's needs.

After treatment, the subject's APOB mRNA levels are lowered relative to the levels existing prior to the treatment, or relative to the levels measured in a similarly afflicted but untreated subject. The initial dose of agent increases LDLR levels in the subject as reflected by the decrease in total serum cholesterol. This increase in LDLR levels increases the efficacy of the siRNA as reflected by the lower dosage of subsequent siRNA administration required to significantly inhibit target gene expression.

Those skilled in the art are familiar with methods and compositions in addition to those specifically set out in the present disclosure which will allow them to practice this invention to the full scope of the claims hereinafter appended.

The invention claimed is:

1. A method for administering a neutral liposomal formulated siRNA targeting a PCSK9 gene to a subject comprising administering to the subject an agent that increases LDLR levels, and subsequently administering a first effective dose of the neutral liposomal formulated siRNA targeting the PCSK9 gene, wherein said first effective dose is lower than an effective dose of the neutral liposomal formulated siRNA administered to the subject without the agent, and wherein the agent is a dsRNA.

2. The method of claim 1, wherein the first effective dose is administered within 3 days of administering the agent.

3. The method of claim 1, wherein the agent is an inhibitor of PCSK9 expression.

4. The method of claim 1, wherein the agent is a PCSK9 targeted siRNA.

5. The method of claim 4, wherein the PCSK9 targeted siRNA agent comprises AD-10792 or AD-9680.

6. The method of claim 4, wherein the PCSK9 targeted siRNA agent is administered at a dosage of 0.5 to 10 mg/kg.

7. The method of claim 4, wherein the PCSK9 targeted siRNA agent is administered at a dosage of 3 mg/kg.

8. The method of claim 1, wherein the agent increases LDLR levels by at least 15%.

9. The method of claim 1, wherein the neutral liposomal formulated siRNA comprises 2,2-Dilinoleyl-4-dimethylaminoethyl[1,3]-dioxolane (XTC) or (6Z,9Z,28Z,31Z)-heptatriaconta-6,9,28,31-tetraen-19-yl 4-(dimethylamino)butanoate (MC3).

10. The method of claim 1, wherein the neutral liposomal formulated siRNA comprises (6Z,9Z,28Z,31Z)-heptatiaconta-6,9,28,31-tetraen-19-yl 4-(dimethylamino)butanoate (MC3).

11. The method of claim 1, wherein the neutral liposomal formulated siRNA comprises ApoE.

12. The method of claim 1, wherein the siRNA targeting the PCSK9 gene comprises a sense strand and an antisense strand comprising at least 15 contiguous nucleotides of a nucleotide sequence of an antisense strand of AD-9680 (SEQ ID NO:1).

13. The method of claim 1, wherein the siRNA targeting the PCSK9 gene comprises AD-9680.

14. The method of claim 1, wherein the subject is mouse, rat, monkey or human.

15. The method of claim 1, wherein the subject is human.

16. The method of claim 1, wherein the subject is a human in need of treatment for a disease correlated with expression of the targeted gene.

17. The method of claim 1, wherein the first effective dose of the neutral liposomal formulated siRNA is 2-50 fold lower than the effective dose administered without the agent.

18. The method of claim 1, wherein the first effective dose of the neutral liposomal formulated siRNA is at least 2 fold lower than the effective dose administered without the agent.

19. The method of claim 1, wherein the first effective dose of the neutral liposomal formulated siRNA is at least 10 fold lower than the effective dose administered without the agent.

20. The method of claim 1, wherein administration of the first effective dose of the neutral liposomal formulated siRNA inhibits target gene expression by at least 15%.

21. The method of claim 1, wherein the first effective dose results in maintenance of at least a 40% decrease in total cholesterol levels.

22. The method of claim 4, wherein administration of the agent results in an initial lowering of total serum cholesterol levels in the subject by at least 15%, wherein subsequent administration of said first effective dose of the neutral liposomal formulated siRNA targeting the PCSK9 gene results in maintenance of lowering of total serum cholesterol levels in the subject by at least 15%, and wherein said first effective dose is at least two fold lower than an effective dose of the neutral liposomal formulated siRNA administered to the subject without the agent.

23. The method of claim 13, wherein the agent is a neutral liposomal formulated AD-9680 dsRNA, wherein the agent is administered to the subject at a dosage resulting in a first result of a lowering in total serum cholesterol levels by about 60% 3 days after administration of the agent, and wherein the first effective dose of the neutral liposomal formulated siRNA comprising AD-9680 is administered at a dosages of 1.0 or 0.3 mg/kg.

24. A method for increasing the efficacy of a neutral liposomal formulated siRNA targeting a PCSK9 gene, comprising administering to a subject in need thereof an agent that increases LDLR levels and subsequently administering an effective dose of the neutral liposomal formulated siRNA targeting the PCSK9 gene, wherein said effective dose is a lower dose than the effective dose of the neutral liposomal formulated siRNA administered to the subject without the agent, and wherein the agent is a dsRNA.

25. The method of claim 23, wherein the uptake efficiency of the neutral liposomal formulated siRNA comprising AD-9680 is increased.

\* \* \* \* \*